(12) United States Patent
Pandey et al.

(10) Patent No.: US 7,897,140 B2
(45) Date of Patent: *Mar. 1, 2011

(54) MULTI DTPA CONJUGATED TETRAPYROLLIC COMPOUNDS FOR PHOTOTHERAPEUTIC CONTRAST AGENTS

(75) Inventors: Ravindra K. Pandey, Williamsville, NY (US); Lalit Goswami, Amherst, NY (US); Joseph Spernyak, West Seneca, NY (US); Peter Kanter, East Aurora, NY (US); Richard Mazurchuk, Clarence Center, NY (US)

(73) Assignee: Health Research, Inc., Buffalo, NY (US)

( * ) Notice: Subject to any disclaimer, the term of this patent is extended or adjusted under 35 U.S.C. 154(b) by 1239 days.

This patent is subject to a terminal disclaimer.

(21) Appl. No.: 11/479,524

(22) Filed: Jun. 30, 2006

(65) Prior Publication Data

US 2007/0053840 A1    Mar. 8, 2007

Related U.S. Application Data

(63) Continuation-in-part of application No. 10/390,438, filed on Mar. 17, 2003, now Pat. No. 7,078,014, which is a continuation-in-part of application No. 09/739,155, filed on Dec. 18, 2000, now Pat. No. 6,534,040, application No. 11/479,524, which is a continuation-in-part of application No. 11/452,511, filed on Jun. 14, 2006, now Pat. No. 7,501,509, which is a continuation-in-part of application No. 10/607,922, filed on Jun. 27, 2003, now Pat. No. 7,166,719.

(60) Provisional application No. 60/392,473, filed on Jun. 27, 2002, provisional application No. 60/171,961, filed on Dec. 23, 1999.

(51) Int. Cl.
*A61K 5/055* (2006.01)

(52) U.S. Cl. ............... 424/9.362; 424/9.3; 424/9.36; 424/9.361; 424/9.363; 424/9.364; 424/9.365; 424/1.65; 424/1.11; 424/9.1; 540/121

(58) Field of Classification Search ........... 424/1.11, 424/1.45, 1.49, 1.65, 1.73, 9.1, 9.2, 9.3, 9.36, 424/9.361, 9.362, 9.364, 9.365, 1.69; 534/7, 534/10–16, 550; 540/1, 121, 400, 450
See application file for complete search history.

(56) References Cited

U.S. PATENT DOCUMENTS

| | | | |
|---|---|---|---|
| 3,710,795 A | 1/1973 | Higuchi et al. | 128/260 |
| 3,817,837 A | 6/1974 | Rubenstein et al. | 195/103.5 R |
| 3,927,193 A | 12/1975 | Hansen et al. | 424/1 |
| RE28,819 E | 5/1976 | Thompson | 424/243 |
| 4,044,126 A | 8/1977 | Cook et al. | 424/243 |
| 4,328,245 A | 5/1982 | Yu et al. | 424/305 |
| 4,331,647 A | 5/1982 | Goldenberg | 424/1 |
| 4,348,376 A | 9/1982 | Goldenberg | 424/1 |
| 4,358,603 A | 11/1982 | Yu | 560/2 |
| 4,361,544 A | 11/1982 | Goldenberg | 424/1 |
| 4,364,923 A | 12/1982 | Cook et al. | 424/46 |
| 4,374,925 A | 2/1983 | Litman et al. | 435/7 |
| 4,409,239 A | 10/1983 | Yu | 424/305 |
| 4,410,545 A | 10/1983 | Yu et al. | 424/305 |
| 4,414,209 A | 11/1983 | Cook et al. | 424/243 |
| 4,444,744 A | 4/1984 | Goldenberg | 424/1.1 |
| 4,468,457 A | 8/1984 | Goldenberg et al. | 435/69 |
| 4,474,893 A | 10/1984 | Reading | 436/547 |
| 4,479,895 A | 10/1984 | Auditore-Hargreaves | 260/112 B |
| 4,521,762 A | 6/1985 | Kapral | 340/347 |
| 4,522,811 A | 6/1985 | Eppstein et al. | 514/2 |
| 4,577,636 A | 3/1986 | Spears | 128/654 |
| 4,624,846 A | 11/1986 | Goldenberg | 424/1.1 |
| 4,649,151 A | 3/1987 | Dougherty et al. | 514/410 |
| 4,656,186 A | 4/1987 | Bommer et al. | 514/410 |
| 4,675,338 A | 6/1987 | Bommer et al. | 514/410 |
| 4,693,885 A | 9/1987 | Bommer et al. | 424/9.61 |
| 4,753,958 A | 6/1988 | Weinstein et al. | 514/410 |
| 4,818,709 A | 4/1989 | Primus et al. | 436/518 |
| 4,861,876 A | 8/1989 | Kessel | 540/145 |
| 4,866,168 A | 9/1989 | Dougherty et al. | 540/145 |
| 4,878,891 A | 11/1989 | Judy et al. | 604/5 |
| 4,889,129 A | 12/1989 | Dougherty et al. | 128/664 |
| 4,916,221 A | 4/1990 | Kumadaki et al. | 540/145 |
| 4,925,736 A | 5/1990 | Shikowitz | 424/449 |
| 4,932,934 A | 6/1990 | Dougherty et al. | 604/21 |
| 4,935,498 A | 6/1990 | Sessler et al. | 534/15 |
| 4,946,778 A | 8/1990 | Ladnar et al. | 435/69.6 |

(Continued)

FOREIGN PATENT DOCUMENTS

EP    0120054 B1    3/1984

(Continued)

OTHER PUBLICATIONS

Bellnier et al., "Population pharmacokinetics of the photodynamic therapy agent 2-[1-hexyloxyethyl]-2-devinyl pyropheophorbide-a in cancer patients", *Cancer Res.*, 63(8):1806-1813 (2003).

Bellnier et al., "Design and construction of a light-delivery system for photodynamic therapy", *Med. Phys.*, 26(8):1552-1558 (1999).

Bellnier et al., "The time course of cutaneous porphyrin photosensitization in the murine ear", *Photochemistry and Photobiology*, 49(3):369-372 (1989).

Bellnier et al., "Murine pharmacokinetics and antitumor efficacy of the photodynamic sensitizer 2-[1-hexyloxyethyl]-2-devinyl pyropheophorbide-a", *J Photochem Photobiol B.* 20(1):55-61 (1993).

(Continued)

*Primary Examiner* — D L Jones
(74) *Attorney, Agent, or Firm* — Michael L. Dunn

(57) ABSTRACT

Novel tetrapyrollic water soluble photosensitizing and imaging compounds and the methods of treating and imaging hyperproliferative tissue, e.g. tumors and hypervacularized tissue such as found in macular degeneration. Broadly, the compounds are tetrapyrollic photosensitizer compounds where the tetrapyrollic compound is a chlorin, bacteriochlorin, porphyrin, pyropheophorbide, purpurinimide, or bacteriopurpurinimide having 3 to 6 —$CH_2CONHphenylCH_2CH(N(CH_2COOH)_2))(CH_2N(CH_2COOH)(CH_2CH_2N(CH_2COOH)_2))$ groups or esters thereof or complexes thereof with gadolinium(III).

27 Claims, 2 Drawing Sheets

U.S. PATENT DOCUMENTS

| | | | | |
|---|---|---|---|---|
| 4,957,481 A | 9/1990 | Gatenby | | 604/20 |
| 4,968,715 A | 11/1990 | Dougherty et al. | | 514/410 |
| 4,997,639 A | 3/1991 | Aizawa et al. | | 424/9 |
| 5,002,962 A | 3/1991 | Pandey et al. | | 514/410 |
| 5,004,811 A | 4/1991 | Bommer et al. | | 540/145 |
| 5,015,463 A | 5/1991 | Dougherty et al. | | 424/7.1 |
| 5,028,594 A | 7/1991 | Carson | | 514/23 |
| 5,028,621 A | 7/1991 | Dougherty et al. | | 514/410 |
| 5,033,252 A | 7/1991 | Carter | | 53/425 |
| 5,041,078 A | 8/1991 | Matthes et al. | | 604/4 |
| 5,051,415 A | 9/1991 | Moran et al. | | 514/185 |
| 5,052,558 A | 10/1991 | Carter | | 206/439 |
| 5,053,006 A | 10/1991 | Watson | | 604/52 |
| 5,059,415 A | 10/1991 | Neuwelt | | 424/9 |
| 5,062,431 A | 11/1991 | Potter | | 128/665 |
| 5,066,274 A | 11/1991 | Bommer et al. | | 604/20 |
| 5,066,291 A | 11/1991 | Stewart | | 606/3 |
| 5,074,632 A | 12/1991 | Potter | | 385/31 |
| 5,093,349 A | 3/1992 | Pandey et al. | | 514/410 |
| 5,095,030 A | 3/1992 | Levy et al. | | 514/410 |
| 5,111,821 A | 5/1992 | Potter | | 128/654 |
| 5,145,863 A | 9/1992 | Dougherty et al. | | 514/410 |
| 5,171,741 A | 12/1992 | Dougherty | | 514/185 |
| 5,173,504 A | 12/1992 | Dougherty | | 514/410 |
| 5,190,536 A | 3/1993 | Wood et al. | | 606/16 |
| 5,190,966 A | 3/1993 | Dougherty et al. | | 514/410 |
| 5,198,460 A | 3/1993 | Pandey et al. | | 514/410 |
| 5,205,291 A | 4/1993 | Potter | | 128/854 |
| 5,216,012 A | 6/1993 | Morgan et al. | | 514/410 |
| 5,219,345 A | 6/1993 | Potter | | 606/15 |
| 5,222,795 A | 6/1993 | Hed | | 362/32 |
| 5,225,433 A | 7/1993 | Dougherty et al. | | 514/410 |
| 5,257,970 A | 11/1993 | Dougherty | | 604/20 |
| 5,263,925 A | 11/1993 | Gilmore, Jr. et al. | | 604/4 |
| 5,298,018 A | 3/1994 | Narciso, Jr. | | 604/21 |
| 5,308,861 A | 5/1994 | Aizawa et al. | | 514/410 |
| 5,314,905 A | 5/1994 | Pandey et al. | | 514/410 |
| 5,323,907 A | 6/1994 | Kalvelage | | 206/531 |
| 5,330,741 A | 7/1994 | Smith et al. | | 424/9 |
| 5,344,928 A | 9/1994 | Masuya et al. | | 544/37 |
| 5,368,841 A | 11/1994 | Trauner et al. | | 424/9 |
| 5,403,308 A | 4/1995 | Wood et al. | | 606/17 |
| 5,418,130 A | 5/1995 | Platz et al. | | 435/2 |
| 5,430,051 A | 7/1995 | Aizawa et al. | | 514/410 |
| 5,441,531 A | 8/1995 | Zarate et al. | | 607/90 |
| 5,459,159 A | 10/1995 | Pandey et al. | | 614/410 |
| 5,482,698 A | 1/1996 | Griffiths | | 424/141 |
| 5,484,803 A | 1/1996 | Richter | | 514/410 |
| 5,496,308 A | 3/1996 | Brown et al. | | 606/15 |
| 5,498,710 A | 3/1996 | Pandey et al. | | 540/145 |
| 5,500,009 A | 3/1996 | Mendes et al. | | 607/88 |
| 5,503,637 A | 4/1996 | Kyricos et al. | | 607/88 |
| 5,506,255 A | 4/1996 | Smith et al. | | 514/410 |
| 5,514,669 A | 5/1996 | Selman | | 514/63 |
| 5,525,338 A | 6/1996 | Goldenberg | | 424/178.1 |
| 5,532,171 A | 7/1996 | Motsenbocker | | 436/533 |
| 5,534,506 A | 7/1996 | Morgan et al. | | 514/185 |
| 5,549,660 A | 8/1996 | Mendes et al. | | 607/88 |
| 5,556,612 A | 9/1996 | Anderson et al. | | 424/59 |
| 5,567,409 A | 10/1996 | Aizawa et al. | | 424/9.363 |
| 5,571,152 A | 11/1996 | Chen et al. | | 607/92 |
| 5,580,896 A | 12/1996 | Horwell et al. | | 514/419 |
| 5,591,847 A | 1/1997 | Pandey et al. | | 540/472 |
| 5,594,136 A | 1/1997 | Sessler et al. | | 540/472 |
| 5,599,923 A | 2/1997 | Sessler et al. | | 540/145 |
| 5,622,983 A | 4/1997 | Horwell et al. | | 514/419 |
| 5,624,798 A | 4/1997 | Yamamoto et al. | | 435/6 |
| 5,631,281 A | 5/1997 | Horwell et al. | | 514/419 |
| 5,648,485 A | 7/1997 | Dolphin et al. | | 540/474 |
| 5,665,328 A | 9/1997 | Horan et al. | | 424/1.17 |
| 5,667,998 A | 9/1997 | Dougherty et al. | | |
| 5,671,317 A | 9/1997 | Weishaupt et al. | | 385/137 |
| 5,686,280 A | 11/1997 | Dougherty et al. | | |
| 5,688,486 A | 11/1997 | Watson et al. | | 424/1.65 |
| 5,697,902 A | 12/1997 | Goldenberg | | 604/49 |
| 5,698,405 A | 12/1997 | Goldenberg | | 435/7.5 |
| 5,702,432 A | 12/1997 | Chen et al. | | 607/88 |
| 5,703,230 A | 12/1997 | Boyle et al. | | 540/145 |
| 5,705,518 A | 1/1998 | Richter et al. | | 514/410 |
| 5,709,874 A | 1/1998 | Hanson et al. | | 424/423 |
| 5,715,837 A | 2/1998 | Chen | | 128/899 |
| 5,716,595 A | 2/1998 | Goldenberg | | 414/1.49 |
| 5,736,563 A | 4/1998 | Richter | | 514/410 |
| 5,741,316 A | 4/1998 | Chen et al. | | 607/61 |
| 5,756,541 A | 5/1998 | Strong et al. | | |
| 5,759,542 A | 6/1998 | Gurewich | | 424/94.64 |
| 5,766,234 A | 6/1998 | Chen et al. | | 607/92 |
| 5,770,619 A | 6/1998 | Richter et al. | | 514/410 |
| 5,770,730 A | 6/1998 | Pandey et al. | | 540/472 |
| 5,773,977 A | 6/1998 | Dougherty | | 324/429 |
| 5,776,093 A | 7/1998 | Goldenberg | | 604/20 |
| 5,776,094 A | 7/1998 | Goldenberg | | 604/20 |
| 5,776,095 A | 7/1998 | Goldenberg | | 604/20 |
| 5,782,896 A | 7/1998 | Chen et al. | | 607/88 |
| 5,800,478 A | 9/1998 | Chen et al. | | 607/88 |
| 5,814,008 A | 9/1998 | Chen et al. | | 604/21 |
| 5,824,080 A | 10/1998 | Lamuraglia | | 623/11 |
| 5,827,186 A | 10/1998 | Chen et al. | | 600/407 |
| 5,829,448 A | 11/1998 | Fisher et al. | | 128/898 |
| 5,831,088 A | 11/1998 | Dolphin et al. | | 540/474 |
| 5,832,931 A | 11/1998 | Wachter et al. | | 128/898 |
| 5,840,674 A | 11/1998 | Yatvin et al. | | 514/2 |
| 5,851,225 A | 12/1998 | Lawandy | | 607/88 |
| 5,860,957 A | 1/1999 | Jacobsen et al. | | 604/156 |
| 5,864,035 A | 1/1999 | Pandey et al. | | 540/472 |
| 5,865,840 A | 2/1999 | Chen | | 607/92 |
| 5,876,427 A | 3/1999 | Chen et al. | | 607/88 |
| 5,885,557 A | 3/1999 | Lentini | | 424/59 |
| 5,886,173 A | 3/1999 | Hemmi et al. | | 540/472 |
| 5,900,252 A | 5/1999 | Calanchi et al. | | 424/459 |
| 5,906,928 A | 5/1999 | Dougherty et al. | | |
| 5,913,884 A | 6/1999 | Trauner et al. | | 607/88 |
| 5,921,244 A | 7/1999 | Chen et al. | | 128/897 |
| 5,942,534 A | 8/1999 | Trauner et al. | | 514/410 |
| 5,944,748 A | 8/1999 | Mager et al. | | 607/88 |
| 5,945,762 A | 8/1999 | Chen et al. | | 310/171 |
| 5,948,433 A | 9/1999 | Burton et al. | | 424/448 |
| 5,952,366 A | 9/1999 | Pandey et al. | | 514/410 |
| 5,957,960 A | 9/1999 | Chen et al. | | 607/92 |
| 5,972,366 A | 10/1999 | Haynes et al. | | 424/422 |
| 5,976,535 A | 11/1999 | Fritzberg et al. | | 424/182.1 |
| 5,983,134 A | 11/1999 | Ostrow | | 604/20 |
| 5,985,307 A | 11/1999 | Hanson et al. | | 424/423 |
| 5,985,317 A | 11/1999 | Venkateshwaran et al. | | 424/449 |
| 5,997,569 A | 12/1999 | Chen et al. | | 607/88 |
| 5,997,842 A | 12/1999 | Chen | | 424/1.29 |
| 5,998,597 A | 12/1999 | Fisher et al. | | 536/23.1 |
| 6,004,534 A | 12/1999 | Langer et al. | | 424/9.321 |
| 6,010,715 A | 1/2000 | Wick et al. | | 424/448 |
| 6,015,897 A | 1/2000 | Theodore et al. | | 540/474 |
| 6,022,961 A | 2/2000 | Yamamoto et al. | | 536/24.3 |
| 6,024,975 A | 2/2000 | D'Angelo et al. | | 424/449 |
| 6,028,099 A | 2/2000 | de Juan, Jr. | | 514/434 |
| 6,036,941 A | 3/2000 | Bottiroli et al. | | 424/9.6 |
| 6,039,975 A | 3/2000 | Shah et al. | | 424/473 |
| 6,048,359 A | 4/2000 | Biel | | 607/92 |
| 6,048,736 A | 4/2000 | Kosak | | 436/536 |
| 6,051,207 A | 4/2000 | Klaveness et al. | | 424/9.1 |
| 6,051,702 A | 4/2000 | Bird et al. | | 540/122 |
| 6,060,082 A | 5/2000 | Chen et al. | | 424/450 |
| 6,063,108 A | 5/2000 | Salansky et al. | | 607/89 |
| 6,063,777 A | 5/2000 | Hikida et al. | | 514/183 |
| 6,071,495 A | 6/2000 | Unger et al. | | 424/9.51 |
| 6,080,160 A | 6/2000 | Chen et al. | | 606/72 |
| 6,084,717 A | 7/2000 | Wood et al. | | 359/629 |
| 6,090,788 A | 7/2000 | Lurie | | 514/23 |
| 6,092,531 A | 7/2000 | Chen et al. | | 128/899 |
| 6,096,066 A | 8/2000 | Chen et al. | | 607/88 |
| 6,096,289 A | 8/2000 | Goldenberg | | 424/1.49 |
| 6,100,893 A | 8/2000 | Ensz et al. | | 345/420 |
| 6,103,751 A | 8/2000 | Pandey et al. | | 514/410 |
| 6,107,466 A | 8/2000 | Hasan et al. | | 530/351 |
| 6,117,862 A | 9/2000 | Margaron et al. | | 514/185 |
| 6,120,751 A | 9/2000 | Unger | | 424/9.51 |
| 6,123,923 A | 9/2000 | Unger et al. | | 424/9.52 |
| 6,124,342 A | 9/2000 | Okamoto et al. | | 514/432 |
| 6,131,570 A | 10/2000 | Schuster et al. | | 128/203.26 |

| | | | |
|---|---|---|---|
| 6,138,681 A | 10/2000 | Chen et al. | 128/899 |
| 6,139,865 A | 10/2000 | Friend et al. | 424/441 |
| 6,152,951 A | 11/2000 | Hashimoto et al. | 607/92 |
| 6,156,506 A | 12/2000 | Yamamoto et al. | 435/6 |
| 6,162,213 A | 12/2000 | Stewart | 606/10 |
| 6,162,242 A | 12/2000 | Peyman | 607/88 |
| 6,167,301 A | 12/2000 | Flower et al. | 604/20 |
| 6,176,842 B1 | 1/2001 | Tachibana et al. | 604/22 |
| 6,187,030 B1 | 2/2001 | Gart et al. | 607/93 |
| 6,210,425 B1 | 4/2001 | Chen | 607/88 |
| 6,217,869 B1 | 4/2001 | Meyer et al. | 424/178.1 |
| RE37,180 E | 5/2001 | Mori et al. | 514/410 |
| 6,232,295 B1 | 5/2001 | Kayyem et al. | 514/44 |
| 6,238,426 B1 | 5/2001 | Chen | 607/88 |
| 6,242,477 B1 | 6/2001 | Okamoto et al. | 514/432 |
| 6,253,872 B1 | 7/2001 | Neumann | 181/210 |
| 6,256,533 B1 | 7/2001 | Yuzhakov et al. | 604/21 |
| 6,261,595 B1 | 7/2001 | Stanley et al. | 424/449 |
| 6,264,914 B1 | 7/2001 | Klaveness et al. | 424/1.65 |
| 6,267,983 B1 | 7/2001 | Fujii et al. | 424/448 |
| 6,268,120 B1 | 7/2001 | Platz et al. | 435/2 |
| 6,271,359 B1 | 8/2001 | Norris et al. | 536/23.1 |
| 6,273,904 B1 | 8/2001 | Chen et al. | 607/88 |
| 6,274,552 B1 | 8/2001 | Tamarkin et al. | 514/12 |
| 6,281,611 B1 | 8/2001 | Chen et al. | 310/171 |
| 6,307,147 B1 | 10/2001 | Bird et al. | 136/263 |
| 6,316,652 B1 | 11/2001 | Steliou | 556/42 |
| 6,319,273 B1 | 11/2001 | Chen et al. | 607/88 |
| 6,319,488 B1 | 11/2001 | Licha et al. | 424/9.6 |
| 6,331,175 B1 | 12/2001 | Goldenberg | 604/522 |
| 6,331,744 B1 | 12/2001 | Chen et al. | 310/171 |
| 6,344,050 B1 | 2/2002 | Chen | 607/88 |
| 6,350,431 B1 | 2/2002 | Snow et al. | 424/9.6 |
| 6,387,350 B2 | 5/2002 | Goldenberg | 424/1.57 |
| 6,406,297 B1 | 6/2002 | Raymond et al. | 434/15 |
| 6,416,531 B2 | 7/2002 | Chen | 607/89 |
| 6,454,789 B1 | 9/2002 | Chen et al. | 607/88 |
| 6,482,517 B1 | 11/2002 | Anderson | 428/402.24 |
| 6,489,314 B1 | 12/2002 | Ashley et al. | 514/183 |
| 6,495,585 B2 | 12/2002 | Bellnier et al. | 514/410 |
| 6,498,945 B1 | 12/2002 | Alfheim et al. | 600/407 |
| 6,500,816 B1 | 12/2002 | Ekimoto et al. | 514/186 |
| 6,511,971 B1 | 1/2003 | Gorun | 514/183 |
| 6,514,995 B1 | 2/2003 | Zaleski et al. | 514/332 |
| 6,515,113 B2 | 2/2003 | Raymond et al. | 534/15 |
| 6,520,669 B1 | 2/2003 | Chen et al. | 362/545 |
| 6,524,552 B2 | 2/2003 | Klaveness et al. | 424/1.85 |
| 6,525,088 B1 | 2/2003 | Nagano et al. | 514/452 |
| 6,527,759 B1 | 3/2003 | Tachibana et al. | 604/500 |
| 6,534,040 B2 * | 3/2003 | Pandey et al. | 424/9.362 |
| 6,540,980 B1 | 4/2003 | Blumenthal et al. | 424/9.34 |
| 6,554,853 B2 | 4/2003 | Chen | 607/88 |
| 6,559,374 B2 | 5/2003 | Lindsey et al. | 136/263 |
| 6,566,517 B2 | 5/2003 | Miura et al. | 540/145 |
| 6,569,846 B1 | 5/2003 | Scherz et al. | 514/185 |
| 6,572,839 B2 | 6/2003 | Sugita et al. | 424/9.5 |
| 6,580,228 B1 | 6/2003 | Chen et al. | 315/185 R |
| 6,602,274 B1 | 8/2003 | Chen | 607/88 |
| 6,624,187 B1 * | 9/2003 | Pandey et al. | 514/410 |
| 6,657,351 B2 | 12/2003 | Chen et al. | 310/171 |
| 6,849,607 B2 * | 2/2005 | Pandey et al. | 514/25 |
| 6,899,723 B2 | 5/2005 | Chen | |
| 6,986,782 B2 | 1/2006 | Chen et al. | |
| RE38,994 E * | 2/2006 | Pandey et al. | 514/410 |
| 7,018,395 B2 | 3/2006 | Chen | |
| RE39,094 E * | 5/2006 | Pandey et al. | 514/410 |
| 7,053,210 B2 | 5/2006 | Pandey et al. | |
| 7,078,014 B2 * | 7/2006 | Pandey et al. | 424/9.3 |
| 7,097,826 B2 * | 8/2006 | Pandey et al. | 424/9.362 |
| 7,147,840 B2 * | 12/2006 | Pandey et al. | 424/9.362 |
| 7,166,719 B2 * | 1/2007 | Pandey et al. | 540/140 |
| 7,501,509 B2 * | 3/2009 | Pandey et al. | 540/145 |
| 2001/0022970 A1 | 9/2001 | Dees et al. | 424/178.1 |
| 2002/0033192 A1 | 3/2002 | Lindsey et al. | 136/263 |
| 2002/0049247 A1 | 4/2002 | Chen | 514/410 |
| 2002/0087205 A1 | 7/2002 | Chen | 607/88 |
| 2002/0127224 A1 | 9/2002 | Chen | 424/130.1 |
| 2002/0127230 A1 | 9/2002 | Chen | 424/178.1 |
| 2002/0128303 A1 | 9/2002 | Bellnier et al. | 514/410 |
| 2002/0198576 A1 | 12/2002 | Chen et al. | 607/88 |
| 2003/0018371 A1 | 1/2003 | Chen | 607/88 |
| 2003/0030342 A1 | 2/2003 | Chen et al. | 310/102 |
| 2003/0109813 A1 | 6/2003 | Chen | 601/2 |
| 2003/0114434 A1 | 6/2003 | Chen et al. | 514/185 |
| 2003/0167033 A1 | 9/2003 | Chen et al. | 604/20 |
| 2003/0208249 A1 | 11/2003 | Chen | 607/88 |
| 2004/0044197 A1 | 3/2004 | Pandey et al. | 540/140 |
| 2004/0044198 A1 | 3/2004 | Pandey et al. | 540/145 |

FOREIGN PATENT DOCUMENTS

| | | |
|---|---|---|
| EP | 0161606 B1 | 11/1985 |
| EP | 0243929 B1 | 11/1987 |
| EP | 0423195 B1 | 4/1991 |
| EP | 0425566 B1 | 5/1991 |
| EP | 0450149 B1 | 10/1991 |
| EP | 0468997 B1 | 2/1992 |
| EP | 0510007 B1 | 10/1992 |
| EP | 0682956 B1 | 11/1995 |
| EP | 1110963 A2 | 6/2001 |
| EP | 1131100 B1 | 9/2001 |
| EP | 1146046 A2 | 10/2001 |
| EP | 1164136 A1 | 12/2001 |
| EP | 1238666 A2 | 9/2002 |
| EP | 1256586 A1 | 11/2002 |
| EP | 1334748 A1 | 8/2003 |
| JP | 4218002 | 7/1992 |
| JP | 6105921 | 4/1994 |
| JP | 2001335578 | 4/2001 |
| JP | 2002020389 | 1/2002 |
| JP | 2002325853 | 11/2002 |
| JP | 2003146989 | 5/2003 |
| WO | 8401382 A1 | 4/1984 |
| WO | 9000392 A1 | 1/1990 |
| WO | 9000895 A1 | 2/1990 |
| WO | 9012573 A1 | 11/1990 |
| WO | 9110474 A1 | 7/1991 |
| WO | 9313769 A1 | 7/1993 |
| WO | 9409851 A1 | 5/1994 |
| WO | 9505214 A1 | 2/1995 |
| WO | 9532206 A1 | 11/1995 |
| WO | 9637255 A1 | 11/1996 |
| WO | 9732520 A1 | 9/1997 |
| WO | 9732885 A1 | 9/1997 |
| WO | 9804317 A1 | 2/1998 |
| WO | 9806456 A1 | 2/1998 |
| WO | 9808565 A1 | 3/1998 |
| WO | 9814243 A1 | 4/1998 |
| WO | 9824371 A1 | 6/1998 |
| WO | 9824510 A1 | 6/1998 |
| WO | 9832491 A1 | 7/1998 |
| WO | 9832492 A1 | 7/1998 |
| WO | 9832493 A1 | 7/1998 |
| WO | 9846130 A1 | 10/1998 |
| WO | 9850034 A1 | 11/1998 |
| WO | 9856302 A1 | 12/1998 |
| WO | 9918879 A1 | 4/1999 |
| WO | 9920346 A1 | 4/1999 |
| WO | 9939769 A1 | 8/1999 |
| WO | 9952565 A1 | 10/1999 |
| WO | 9968149 A1 | 11/1999 |
| WO | 9966988 A1 | 12/1999 |
| WO | 9967248 A1 | 12/1999 |
| WO | 9967249 A1 | 12/1999 |
| WO | WO99/67248 | 12/1999 |
| WO | WO99/67249 | 12/1999 |
| WO | 0015296 A1 | 3/2000 |
| WO | 0036983 A1 | 6/2000 |
| WO | 0041725 A2 | 7/2000 |
| WO | 0041726 A3 | 7/2000 |
| WO | 0041727 A1 | 7/2000 |
| WO | 0041768 A1 | 7/2000 |
| WO | 00/61584 A1 | 10/2000 |
| WO | 0103770 A1 | 1/2001 |
| WO | 0105316 A1 | 1/2001 |
| WO | 0115694 A1 | 3/2001 |
| WO | 0143825 A1 | 6/2001 |
| WO | 0151087 A2 | 7/2001 |
| WO | 01/74398 A1 | 10/2001 |

| | | | |
|---|---|---|---|
| WO | 0176216 A1 | 10/2001 | |
| WO | 0178458 A1 | 10/2001 | |
| WO | 0198708 A1 | 12/2001 | |
| WO | 0217690 A1 | 2/2002 | |
| WO | 02/098882 A1 | 12/2002 | |
| WO | 03029494 A1 | 4/2003 | |
| WO | 03/050082 A2 | 6/2003 | |
| WO | 03052793 A2 | 6/2003 | |
| WO | WO03/052793 | 6/2003 | |
| WO | 03056407 A2 | 7/2003 | |
| WO | 03061695 A2 | 7/2003 | |
| WO | WO03/061696 | 7/2003 | |
| WO | 2004/002476 A2 | 1/2004 | |
| WO | 2004/005289 A2 | 1/2004 | |
| WO | WO2004/002476 | 1/2004 | |
| WO | WO2004/002486 | 1/2004 | |
| WO | WO2004/005289 | 1/2004 | |

OTHER PUBLICATIONS

Bellnier et al., "The validation of a new vascular damage assay for photodynamic therapy agents", *Photochem Photobiol.*, 62(5):896-905 (1995).
Bellnier et al. "Protection of murine foot tissue and transplantable tumor against Photofrin-II-mediated photodynamic sensitization with WR-2721", *Journal of Photochemistry and Photobiology B. Biology* 4:219-225 (1989).
Bellnier et al. "An assay for the quantitation of Photofrin in tissues and fluids", *Photochem Photobiol.* 66(2):237-244 (1997).
Bellnier et al., "Distribution and elimination of Photofrin II in mice", *Photochemistry and Photobiology* 50(2):221-228 (1989).
Bellnier et al., "Membrane lysis in Chinese hamster ovary cells treated with hemtoporphyrin derivative plus light", *Photochem Photobiol.* 36(1):43-47 (1982).
Bellnier et al., "A preliminary pharmacokinetic study of intravenous Photofrin in patients", *J Clin Laser Med Surg.*, 14(5):311-4 (1996).
Bellnier et al., "Haematoporphyrin derivative photosensitization and gamma-radiation damage interaction in Chinese hamster ovary fibroblasts", *Int J Radiat Biol Relat Stud Phys Chem Med.* 50(4):659-664 (1986).
Bernstein et al., "Photofrin photodynamic therapy for treatment of AIDS-related cutaneous Kaposi's sarcoma", *AIDS*, 13(13):1697-1704 (1999).
Box et al., "Radical ion saturation in some sulfur compounds x-irradiated at 4.2 degrees" *K. Radiat Res.* 51(1):10-14 (1972).
Boyle et al., "Photobleaching of photofrin II as a means of eliminating skin photosensitivity", *Photochemistry and Photobiology*, 46(6):997-1001 (1987).
Brasseur et al., "Photodynamic activities and skin photosensitivity of the bis(dimethylthexylsiloxy)silicon 2,3-naphthalocyanine in mice", *Photochemistry and Photobiology* 62(6):1058-1065 (1995).
Brennan et al.,"Preparation of Bispecific Antibodies by Chemical Recombination of Monoclonal Immunoglobulin $G_1$ Fragments-",*Science*, 229: 81-83 (1985).
Bugelski et al., "Autoradiographic distribution of hematoporphyrin derivative in normal and tumor tissue of the mouse", *Cancer Res:*, 41(11 Pt 1):4606-4612 (1981).
Chen et al., "Effect of meso-substituents on the osmium tetraoxide reaction and pinacol-pinacolone rearrangement of the corresponding vic-dihydroxyporphyrins", *J Org Chem*. 66(11):3930-3939 (2001).
Chen et al., "Bacteriopurpurinimides: highly stable and potent photosensitizers for photodynamic therapy", *J. Med. Chem.* 45:255-258 (2002).
Derwent Abstract Accession No. 9432597, for Japanese Patent Application JP 2003146989 published May 21, 2003, entitled "Pyropheophorbides and their use in photodynamic therapy".
Dimitroff et al., "Anti-angiogenic activity of selected receptor tyrosine kinase inhibitors, PD166285 and PD173074: implications for combination treatment with photodynamic therapy", *Investigational New Drugs*, 17:121-135 (1999).
Dissous et al. ,*Schistosome mansoni* Surface Antigen Defined by a Rat Monoclonal IgG2a,*J. Immunol.* 129: 2232-2234 (1982).
Doiron et al., "Fluorescence bronchoscopy for detection of lung cancer", *Chest*, 76(1):27-32 (1979).

Dougherty TJ, "Transannular peroxides as radiation sensitizers", *Radiat Res.*, 55(1):101-108 (1973).
Dougherty TJ, "A brief history of clinical photodynamic therapy development at Roswell Park Cancer Institute", *J Clin Laser Med Surg.* 14(5):219-221 (1996).
Dougherty TJ, "Use of hematoporphyrin in photodynamic therapy", *J Photochem Photobiol B.* 8(4):439 (1991).
Dougherty TJ, "Photosensitizers: therapy and detection of malignant tumors", *Photochemistry and Photobiology* 45(6):879-889 (1987).
Dougherty TJ, "Activated dyes as antitumor agents", *J Natl Cancer Inst.* 52(4):1333-1336 (1974).
Dougherty TJ, "Photodynamic therapy", *Photochem Photobiol.*, 58(6):895-900 (1993).
Dougherty TJ, "Photodynamic Therapy: Part II", *Seminars in Surgical Oncology*, 11:333-334 (1995).
Dougherty TJ, "Photodynamic therapy: status and potential", *Oncology (Huntingt)*. 3(7):67-73; Discussion 74, 77-78 (1989).
Dougherty TJ, "Photoradiation therapy for cutaneous and subcutaneous malignancies", *J Invest Dermatol.* 77(1):122-124 (1981).
Dougherty TJ, "Photodynamic therapy (PDT) of malignant tumors", *CRC Critical Reviews in Oncology/Hematology* 2(2):83-116 (1984).
Dougherty TJ, "Photoradiation therapy", *Urology*, 23(3 Suppl):61-64 (1984).
Dougherty TJ, "Photosensitization of malignant tumors", *Seminars in Surgical Oncology* 2:24-37 (1986).
Dougherty TJ, "Variability in hematoporphyrin derivative preparations", *Cancer Res.* 42(3):1188 (1982).
Dougherty TJ, "Photoradiation therapy for bronchogenic cancer", *Chest*, 81(3):265-266 (1982).
Dougherty TJ, "Photodynamic therapy—new approaches", *Seminars in Surgical Oncology* 5:6-16 (1989).
Dougherty TJ, "Hematoporphyrin as a photosensitizer of tumors", *Photochem Photobiol.* 38(3):377-379 (1983).
Dougherty TJ, "Photodynamic therapy", *Adv Exp Med Biol.*, 193:313-328 (1985).
Dougherty TJ, "Photodynamic therapy", *Clinics in Chest Medicine*, 6(2):219-236 (1985).
Dougherty TJ, "An update on photodynamic therapy applications", *J Clin Laser Med Surg*. 20(1):3-7 (2002).
Dougherty TJ, "Studies on the structure of porphyrins contained in Photofrin II" *Photochem Photobiol.*, 46(5):569-573 (1987).
Dougherty et al., "Energetics and efficiency of photoinactivation of murine tumor cells containing hematoporphyrin", *Cancer Research* 36:2330-2333 (1976).
Dougherty et al., "Photoradiation therapy. II. Cure of animal tumors with hematoporphyrin and light", *Journal of the National Cancer Institute*, 55(1):115-121 (1975).
Dougherty et al., "Photoradiation therapy for the treatment of malignant tumors", *Cancer Res.* 38(8):2628-2635 (1978).
Dougherty et al., "Photodynamic Therapy," *Journal of the National Cancer Institute*, 90(12):889-905 (1998).
Dougherty TJ, "Hematoporphyrin derivative for detection and treatment of cancer", *J Surg Oncol.* 15(3):209-210 (1980).
Dougherty et al., "Photoradiation therapy—clinical and drug advances", *Adv Exp Med Biol.* 160:3-13 (1983).
Dougherty et al., "Photoradiation in the treatment of recurrent breast carcinoma", *J Natl Cancer Inst.*, 62(2):231-237 (1979).
Dougherty et al., "Cutaneous phototoxic occurrences in patients receiving Photofrin", *Lasers Surg Med.* 10(5):485-488 (1990).
Dougherty et al., "Interstitial photoradiation therapy for primary solid tumors in pet cats and dogs", *Cancer Res.* 41(2):401-404 (1981).
Dougherty, "Photodynamic therapy in gastrointestinal cancer", *Lasers in Surgery and Medicine* 12:114 (1992).
Dougherty et al., "Characterization of intra-tumoral porphyrin following injection of hematoporphyrin derivative or its purified component", *Photochemistry and Photobiology*, 46(1):67-70 (1987).
Dougherty et al., "The role of the peripheral benzodiazepine receptor in photodynamic activity of certain pyropheophorbide ether photosensitizers: albumin site II as a surrogate marker for activity", *Photochem Photobiol.*, 76(1):91-97 (2002).
Dougherty TJ, "An overview of the status of photoradiation therapy", *Prog Clin Biol Res.* 170:75-87 (1984).

Dougherty et al., "Photodynamic therapy", *Eur J Cancer.* 28A(10):1734-1742 (1992).

Dougherty et al., "The structure of the active component of hematoporphyrin derivative", *Prog Clin Biol Res.*, 170:301-314 (1984).

Dougherty et al., "Of what value is a highly absorbing photosensitizer in PDT?" *J Photochem Photobiol B.*, 8(2):223-225 (1991).

Douglass et al., "Intra-abdominal applications of hematoporphyrin photoradiation therapy", *Adv Exp Med Biol.*, 160:15-21 (1983).

Farrell et al., "A diffusion theory model of spatially resolved, steady-state diffuse reflectance for the noninvasive determination of tissue optical properties in vivo", *Med. Phys.*, 19(4):879-888 (1992).

Fingar et al., "Drug and light dose dependence of photodynamic therapy: a study of tumor cell clonogenicity and histologic changes", *Photochem Photobiol.*, 45(5):643-650 (1987).

Flock et al., "Monte Carlo Modeling of Light Propagation in Highly Scattering Tissues—I:Model Predictions and Comparison with Diffusion Theory," *IEEE Transactions on Biomedical Engineering*, 36(12):1162-1168 (1989).

Flock et al., "Monte Carlo Modeling of Light Propagation in Highly Scattering Tissues—II: Comparison with Measurements in Phantoms," *IEEE Transactions on Biomedical Engineering*, 36(12):1169-1173 (1989).

Fukuzumi et al., "Photochemical and electrochemical properties of zinc chlorin-C60 dyad as compared to corresponding free-base chlorin-C60, free-base porphyrin-C60, and zinc porphyrin-C60 dyads", *J Am Chem Soc.*, 123(43):10676-10683 (2001).

Glennie et al., "Preparation and Performance of Bispecific F(ab'$\gamma$)$_2$ Antibody Containing Thioether-Linked Fab'$\gamma$ Fragments",*J. Immunol.*, 139:2367-2375 (1987).

Gomer CJ et al., "Determination of [3H]- and [4C]hematoporphyrin derivative distribution in malignant and normal tissue", *Cancer Res.* 39(1):146-151 (1979).

Graham et al., "Structure-activity relationship of new octaethylporphyrin-based benzochlorins as photosensitizers for photodynamic therapy", *Photochem Photobiol.* 77(5):561-566 (2003).

Gryshuk et al., "A first comparative study of purpurinimide-based fluorinated vs. nonfluorinated photosensitizers for photodynamic therapy", *Photochem Photobiol.*, 76(5):555-559 (2002).

Gryzch et al., "In Vitro and In Vivo Effector Function of Rat IgG2a Monoclonal Anti-*S. masoni* Antibodies",*J. Immunol.* 129: 2739-2743 (1982).

Henderson et al., "Tumor destruction and kinetics of tumor cell death in two experimental mouse tumors following photodynamic therapy", *Cancer Res.*, 45(2):572-576 (1985).

Henderson et al., "Interaction of photodynamic therapy and hyperthermia: tumor response and cell survival studies after treatment of mice in vivo", *Cancer Res.*, 45(12 Pt 1):6071-6077 (1985).

Henderson et al., "Bacteriochlorophyll-*a* as photosensitizer for photodynamic treatment of transplantable murine tumors", *J. Photochem. Photobiol. B: Biol.* 10:303-313 (1991).

Henderson et al., "An in vivo quantitative structure-activity relationship for a congeneric series of pyropheophorbide derivatives as photosensitizers for photodynamic therapy", *Cancer Res.* 57(18):4000-4007 (1997).

Henderson et al., "How does photodynamic therapy work?" *Photochem Photobiol.* 55(1):145-157 (1992).

Henderson et al., "Aspects of the cellular uptake and retention of hematoporphyrin derivative and their correlation with the biological response to PRT in vitro", *Adv Exp Med Biol.*, 160:129-38 (1983).

Henderson et al., "Studies on the mechanism of tumor destruction by photoradiation therapy", *Prog Clin Biol Res.* 170:601-612 (1984).

Herrera-Ornelas et al., "Photodynamic therapy in patients with colorectal cancer", *Cancer*, 57(3):677-684 (1986).

Ho et al., "Some components of the tumor-localizing fraction of hematoporphyrin derivative", *Photochemistry and Photobiology*, 52(6):1085-1088 (1990).

Ho et al., "Carbon-14 labeling and biological activity of the tumor-localizing derivative of hematoporphyrin", *Photochem Photobiol.* 48(4):445-449 (1988).

Ho et al., "Activity and physicochemical properties of Photofrin", *Photochem Photobiol.* 54(1):83-87 (1991).

IUPAC-IUB Commission on Biochemical Nomenclature (see, Biochem. 11: 942-944 (1972).

Karpovsky et al., "Production of Target-Specific Effector Cells Using Hetero-Cross-Linked Aggregates Containing Anti-Target Cell and Anti-Fc$\gamma$", *J. Exp. Med.* 160:1686 (1984).

Kasper et al., "Isolation and Characterization of a Monoclonal Antibody-Resistant Antigenic Mutant of *Toxoplasma gondii*", *J. Immunol.* 129: 1694-1699 (1982).

Kessel et al., "Photosensitization with bacteriochlorins", *Photochem Photobiol.*, 58(2):200-203 (1993).

Kessel et al., "Photosensitization by diporphyrins joined via methylene bridges", *Photochemistry and Photobiology* 48(6):741-744 (1988).

Kessel et al., "Photosensitization by synthetic diporphyrins and dichlorins in vivo and in vitro", *Photochemistry and Photobiology* 53(4):475-479 (1991).

Khan et al., "An evaluation of photodynamic therapy in the management of cutaneous metastases of breast cancer", *Eur. J Cancer.* 29A(12):1686-1690 (1993).

Kher et al., "Mechano and thermoluminescence of gamma-irradiated CaSO4:Dy phosphor.", *Radiat Prot Dosimetry.* 100(1-4):281-284 (2002).

Kozyrev et al., "Thermolysis of vic-dihydroxybacteriochlorins: a new approach for the synthesis of chlorin-chlorin and chlorin-porphyrin dimers", *Org Lett.* 1(8):1193-1196 (1999).

Lele et al., "Photodynamic therapy in gynecologic malignancies", *Gynecol Oncol.* 34(3):350-352 (1989).

Li et al., "A novel synthetic route to fused propenochlorin and benzochlorin photodynamic therapy probes", *Chem Commun (Camb).* (11):1172-1173 (2002).

Li et al., "Thermolysis of vic-dihydroxybacteriochlorins: effect of the nature of substrates in directing the formation of chlorin-chlorin dimers with fixed and flexible orientations and their preliminary in vitro photosensitizing efficacy", *J Org Chem.* 68(10):3762-3772 (2003).

Li et al., "A simple and efficient approach for the synthesis of fluorinated and nonfluorinated octaethylporphyrin-based benzochlorins with variable lipophilicity, their in vivo tumor uptake, and the preliminary in vitro photosensitizing efficacy", *J Org Chem.* 66(4):1316-1325 (2001).

Liu, Ma et al., "Heteroantibody duplexes target cells for lysis by cytotoxic T lymphocytes",*Proc. Natl. Acad. Sci. USA* 82:8648-8652 (1985).

Lobel et al., "2-[1-hexyloxyethyl]-2-devinyl pyropheophorbide-a (HPPH) in a nude rat glioma model: implications for photodynamic therapy", *Lasers Surg Med.* 29(5):397-405 (2001).

MacDonald et al., "Subcellular localization patterns and their relationship to photodynamic activity of pyropheophorbide-a derivatives", *Photochem Photobiol.* 70(5):789-797 (1999).

Mang et al., "Photobleaching of porphyrins used in photodynamic therapy and implications for therapy", *Photochemistry and Photobiology*, 45(4):501-506 (1987).

Mang et al., "Time and sequence dependent influence of in vitro photodynamic therapy (PDT) survival by hyperthermia", *Photochem Photobiol.*, 42(5):533-540 (1985).

Mang et al., "Fluorescence detection of tumors. Early diagnosis of microscopic lesions in preclinical studies", *Cancer* 71(1):269-276 (1993).

Merrifield et al., "Design and synthesis of antimicrobial peptides", *Ciba Foundation Symposium*, 186:5-20 (1994).

Mettath et al., "DNA interaction and photocleavage properties of porphyrins containing cationic substituents at the peripheral position" *Bioconjugate Chem.*, 10:94-102 (1999).

Mettath et al., "Effect of substituents in directing the formation of benzochlorins and isobacteriochlorins in porphyrin and chlorin systems", *Organic Letters* 1(12):1961-1964 (1999).

Milstein et al., "Hybrid hybridomas and the production of bi-specific monoclonal antibodies",*Immunol. Today* 5:299-305 (1984).

Moesta et al., "Protoporphyrin IX occurs naturally in colorectal cancers and their metastases" *Cancer Research*, 61:991-999 (2001).

Morgan et al., "Comparison of photodynamic targets in a carcinoma cell line and its mitochondrial DNA-deficient derivative", *Photochemistry and Photobiology*, 71(6):747-757 (2000).

Morrison and Boyd, *Organic Chemistry*, (5th Ed., 1987), Chapter 13, entitled "Aromaticity," pp. 477-497.
Moskal et al., "Operation and photodynamic therapy for pleural mesothelioma: 6-year follow-up", *Ann Thorac Surg.*, 66:1128-1133 (1998).
Nambisan et al., "Intraoperative photodynamic therapy for retroperitoneal sarcomas", *Cancer*, 61(6):1248-1252 (1988).
Niedre et al., "Direct Near-infrared Luminescence Detection of Singlet Oxygen Generated by Photodynamic Therapy in Cell in Vitro and Tissues in Vivo", *Photochemistry and Photobiology*, 75(4):382-391 (2002).
Nogrady, Medicinal Chemistry A Biochemical Approach, Oxford University Press, New York, pp. 388-392 (1985).
North et al. "Viral Inactivation in Blood and Red Cell Concentrates with Benzoporphyrin Derivative", *Blood Cells* 18:129-40 (1992).
Nseyo et al., "Study of factors mediating effect of photodynamic therapy on bladder in canine bladder model", *Urology*, 32(1):41-45 (1988).
Nseyo et al., "Whole bladder photodynamic therapy for transitional cell carcinoma of bladder", *Urology*, 26(3):274-280 (1985).
Nseyo et al., "Photodynamic therapy in the management of resistant lower urinary tract carcinoma", *Cancer* 60:3113-3119 (1987).
Nseyo et al., "Photodynamic therapy (PDT) in the treatment of patients with resistant superficial bladder cancer: a long-term experience", *Journal of Clinical Laser Medicine Surgery*, 16(1):61-68 (1998).
Nseyo et al., "Dihematoporphyrin ether clearance in primate bladders", *The Journal of Urology*, 136:1363-1366 (1986).
Nseyo et al., "Experimental photodynamic treatment of canine bladder", *J Urol.*, 133(2):311-315 (1985).
Paajanen et al., "Proton Relaxation Enhancement of Albumin, Immunoglobulin G, and Fibrinogen Labeled with Gd-DTPA",*Magn. Reson. Med* 13: 38-43 (1990).
Pandey et al., "Synthesis and photosensitizing activity of a di-porphyrin ether", *Chemical Abstracts*, 109:320 (1988).
Pandey et al., "Synthesis, photophysical properties, in vivo photosensitizing efficacy, and human serum albumin binding properties of some novel bacteriochlorins", *J. Med. Chem.* 40(17):2770-2779 (1997).
Pandey et al., "Chlorin and porphyrin derivatives as potential photosensitizers in photodynamic therapy", *Photochemistry and Photobiology* 53(1):65-72 (1991).
Pandey et al. (1999).
Pandey et al., "Syntheses and photosensitizing activity of porphyrins joined with ester linkages", *Cancer Research* 49:2042-2047 (1989).
Pandey et al., "Evaluation of new benzoporphyrin derivatives with enhanced PDT efficacy", *Photochemistry and Photobiology* 62(4):764-768 (1995).
Pandey et al., "Alkyl ether analogs of chlorophyll-a derivatives: Part 1. Synthesis, photophysical properties and photodynamic efficacy", *Photochemistry and Photobiology* 64(1):194-204 (1996).
Pandey et al., "Porphyrin dimers as photosensitizers in photodynamic therapy", *J. Med. Chem.* 33:2032-2038 (1990).
Pandey et al., "Fast atom bombardment mass spectral analyses of Photofrin II and its synthetic analogs", *Biomedical and Environmental Mass Spectrometry* 19:405-414 (1990).
Pandey et al., "Comparative in vivo sensitizing efficacy of porphyrin and chlorin dimers joined with ester, ether, carbon-carbon or amide bonds" *Journal of Molecular Recognition* 9:118-122 (1996).
Pierce Chemical Co. catalog, pp. O-90 to O-110 (1995, Pierce Chemical Co., 3747 N. Meridian Rd., Rockford Ill., 61105, U.S.A.).
Polin, R.A. "Monoclonal Antibodies Against Microorganisms", *Eur. J. Clin. Microbiol.*, 3(5): 387-398 (1984).
Potter et al., "The theory of photodynamic therapy dosimetry: consequences of photo-destruction of sensitizer", *Photochemistry and Photobiology* 46(1):97-101 (1987).
Potter et al., "Photofrin II levels by in vivo fluorescence photometry", *Prog Clin Biol Res.* 170:177-186 (1984).
Potter et al., "Parabolic quantitative structure-activity relationships and photodynamic therapy: application of a three-compartment model with clearance to the in vivo quantitative structure-activity relationships of a congeneric series of pyropheophorbide derivatives used as photosensitizers for photodynamic therapy", *Photochemistry and Photobiology* 70(5):781-788 (1999).
Prakash, G.K.S. and A.K. Yudin, "Perfluoralkylation with Organosilicon Reagents", *Chem Rev.*, 97:757-786 (1997).
Pykett, "NMR Imaging in Medicine", *Scientific American* 246: 78 (1982).
Rakestraw, et al. ,"Antibody-targeted photolysis: In vitro studies with Sn(IV) chlorin e6 covalently bound to monoclonal antibodies using a modified dextran carrier", *Proc. Nad. Acad. Sci. USA* 87: 4217-4221 (1990).
Ris et al., "Absence of rhodamine 123-photochemotoxicity in human tumor xenografts", *Lasers Surg Med.* 13(1):40-44 (1993).
Roy et al., "Ceramic-Based Nanoparticles Entrapping Water-Insoluble Photosensitizing Anticancer Drugs: A Novel Drug-Carrier System for Photodynamic Therapy", *J Am Chem Soc.* 125(26):7860-7865 (2003).
Runfola et al., "Photodynamic therapy for residual neoplasms of the perianal skin", *Dis Colon Rectum.* 43(4):499-502 (2000).
Runge et al., "Paramagnetic Agents for Contrast-Enhanced NMR Imaging: A Review", *Am. J. Radiol.* 141: 1209 (1983).
Rungta et al., "Purpurinimides as photosensitizers: effect of the presence and position of the substituents in the in vivo photodynamic efficacy", *Bioorg Med Chem Lett.* 10(13):1463-1466 (2000).
Schuh et al., "Photodynamic therapy for palliation of locally recurrent breast carcinoma", *Journal of Clinical Oncology* 5(11):1766-1770 (1987).
Senge et al., "Comparative Analysis of the Conformations of Symmetrically and Asymmetrically Deca- and Undecasubstituted Porphyrins Bearing Meso-Alkyl or -Aryl Groups", *Inorg. Chem.*, 36:1149-1163 (1997).
Sery et al., "Photoradiation of rabbit ocular malignant melanoma sensitized with hematoporphyrin derivative", *Curr Eye Res.* 3(4):519-528 (1984).
Sharman et al., "Photodynamic therapeutics: basic principles and clinical applications", *Curr. Trends Drug Discovery Today* 4, 507 (1999).
Siegel et al., "Comparative mass spectrometric analyses of Photofrin oligomers by fast atom bombardment mass spectrometry, UV and IR matrix-assisted laser desorption/ionization mass spectrometry, electrospray ionization mass spectrometry and laser desorption/jet-cooling photoionization mass spectrometry", *J Mass Spectrom.* 34(6):661-669 (1999).
Simpson et al., Isolation and partial characterization of the tegumental outer membrane of adult *Schistosoma mansoni*,*Parasitology* 83: 163-177 (1981).
Singh et al., "Thiocarbamate linkage as internucleoside bond", *Indian J Biochem Biophys.* 33(5):425-427 (1996).
Smith et al.,"Passive immunization of mice against *Schistosoma mansoni* with an IgM monoclonal antibody",*Parasitology* 84: 83-91 (1982).
Smith, et al., "*Meso* Substitution of Chlorophyll Derivatives: Direct Route for Transformation of Bacteriopheophorbides *d* into Bacteriopheophorbides *c*", *J. Am. Chem. Soc.* 107: 4946-4954 (1985).
Svaasand et al., "Temperature rise during photoradiation therapy of malignant tumors", *Med Phys.* 10(1):10-17 (1983).
Takita et al., "Intracavitary photodynamic therapy for malignant pleural mesothelioma", *Semin Surg Oncol.* 11:368-371 (1995).
Takita et al., "Operation and intracavitary photodynamic therapy for malignant pleural mesothelioma: a phase II study", *Ann Thorac Surg.* 58(4):995-998 (1994).
Tsuchida et al., "Correlation between site II-specific human serum albumin (HSA) binding affinity and murine in vivo photosensitizing efficacy of some Photofrin components", *Photochemistry and Photobiology* 66(2):224-228 (1997).
Umemura et al., *Ultrasonics Sonochemistry* 3: S187-S191 (1996).
Valenzo et al. eds. (1991).
Van Lier, J.E. "Photosensitization: Reaction Pathways", *Photobiological Techniques* 216:85-98 (1991).
Vincent et al., "Photoradiation therapy in advanced carcinoma of the trachea and bronchus", *Chest*, 85(1):29-33 (1984).
Vincent et al., "Hematoporphyrin derivative in the diagnosis and treatment of lung cancer", *Adv Exp Med Biol.* 160:41-46 (1983).

Waldow et al., "Interaction of hyperthermia and photoradiation therapy" *Radiat Res.* 97(2):380-385 (1984).

Waldow et al., "Potentiation of photodynamic therapy by heat: effect of sequence and time interval between treatments in vivo", *Lasers Surg Med.* 5(2):83-94 (1985).

Waldow et al., "Enhanced tumor control following sequential treatments of photodynamic therapy(PDT) and localized microwave hyperthermia in vivo", *Lasers Surg Med.* 4(1):79-85 (1984).

Waldow et al., "Hyperthermic potentiation of photodynamic therapy employing Photofrin I and II: comparison of results using three animal tumor models", *Lasers Surg Med.* 7(1):12-22 (1987).

Weishaupt et al., "Identification of singlet oxygen as the cytotoxic agent in photoinactivation of a murine tumor", *Cancer Res.*, 36(7 PT 1):2326-2329 (1976).

Wilson et al., "The physics of photodynamic therapy," *Phys. Med. Biol.*, 31(4):327-360 (1986).

Wilson et al., "Photodynamic therapy for the treatment of basal cell carcinoma", *Arch Dermatol.* 128:1597-1601 (1992).

Wood et al., "A beam-splitting device for use with fiber-coupled laser light sources for photodynamic therapy", *Photochem Photobiol.*, 76(6):683-685 (2002).

Yoshida et al., "Hybridoma Produces Protective Antibodies Directed Against the Sporozoite Stage of Malaria Parasite", *Science*, 207:71-73 (1980).

Yumita et al., Sonodynamically induced antitumor effect of gallium-porphyrin complex by focused ultrsound on experimental kidney tumor *Cancer Letters* 1,2: 79-86 (1997).

Yumita et al., "The Comination Treatment of Ultrasound and Antitumor Drugs on Yoshida Sarcoma", *Japan J. Hyperthermic Oncology* 3(2):175-182 (1987).

Zheng et al., "A Simple and Short Synthesis of Divinyl Chlorophyll Derivatives", *J Org Chem.* 64:3751-3754 (1999).

Zheng et al., "Synthesis of beta-galactose-conjugated chlorins derived by enyne metathesis as galectin-specific photosensitizers for photodynamic therapy", *J Org Chem.* 66(26):8709-8716 (2001).

Zheng et al, "Synthesis, photophysical properties, tumor uptake, and preliminary in vivo photosensitizing efficacy of a homologous series of 3-(1'-alkyloxy)ethyl-3-devinylpurpurin-1B-$N$-alkylimides with variable lipophilicity", *J Med Chem.* 44:1540-1559 (2001).

Zheng et al., "Photosensitizers related to purpurin-18-$N$-alkylimides: a comparative in vivo tumoricidal ability of ester versus amide functionalities", *Bioorganic & Medicinal Chemistry Letters*, 10:123-127 (2000).

Zheng et al., "Wittig reactions on photoprotoporphyrin IX: new synthetic models for the special pair of the photosynthetic reaction center", *J Org Chem.* 65(2):543-557 (2000).

Zodda et al.,Monoclonal Antibody-Mediated Protection against *Schistosoma mansoni* Infection in Mice, *J. Immunol.* 129: 2326-2328 (1982).

Anderson et al. "Photodynamic therapy for sarcoma pulmonary metastases: a preclinical toxicity study," *Anticancer Res.* 23:3713-3718 (2003).

Certified English Translation of: Fischer, H. et al., "[On the Bromination of the Esters of Mesoisochlorin e4 and Mesochlorin e6]," *Berischte der Deutschen Chemischen* 75:1778-1795 (1942).

Chen et al., "New directions in photodynamic therapy," *ICCP-2. 2nd International Conference on Porphyrins and Phthalocyanines*, Jun. 30, 2002-Jul. 5; Kyoto, Japan: 78 [abstract S-26].

Chen et al., "New technology for deep light distribution in tissue for phototherapy," *Cancer J* 8(2):154-163. (2002).

Chen et al., "Next-generation light delivery system for multitreatment extended-duration photodynamic therapy (MED-PDT)," *Proc SPIE* 2972:161-166 (1997).

Database Crossfire Beilstein, Database Acession No. 4286587 (Reaction ID), for Levinson, E.G. et al., Russ. J. Bioorg. Chem (Engl. Transl.) 21(3):199-203 (1995) in Russian in the :Bioorg. Khim. 21(3):230-234 (1995).

Derwent English Abstract, Accession No. 1996-475153, citing Russian Patent RU 2054944 C, published Feb. 27, 1996, "Production of purpurin-18 for treatment of tumours—comprises extracting vegetable waste with ethanol, oxidative splitting, degreasing and purifying".

Fischer, H. et al., "[On the Bromination of the Esters of Mesoisochlorin $e_4$ and Mesochlorin $e_6$]," *Berischte der Deutschen Chemischen* 75:1778-1795 (1942).

Haslam et al., "Recent Developments In Methods for the Esterification and Protection of the Carboxyl Group," *Tetrahedron* 36: 2409-2433 (1980).

Jones et al, "Photodynamic therapy for patients with advanced non-small-cell carcinoma of the lung," *Clin Lung Cancer*, 3(1):37-41(2001).

Li et al., "Application of Ruppert's reagent in preparing novel perfluorinated porphyrins, chlorins and bacteriochlorins", *J. Chem. Soc. Perkin Trans* 1, 1785-1787 (1999).

Li et al., "Synthesis, comparative photosensitizing efficacy, human serum albumin (site II) binding ability, and intracellular localization characteristics of novel benzobacteriochlorins derived from vic-dihydroxybacteriochlorins,", *J Med Chem.* 46(25):5349-5359 (2003).

Lustig et al., "A multicenter Phase I safety study of intratumoral photoactivation of talaporfin sodium in patients with refractory solid tumors," *Cancer* 98(8):1767-71 (2003).

Patent Abstract of Japan citing Japanese Patent Application JP 09124652, published May 13, 1997, "Porphyrin Derivative and Use Thereof".

Schmidt-Erfurth et al., "Photodynamic therapy of subfoveal choroidal neovascularization: clinical and angiographic examples," *Graefe's Arch Clin Exp Opthalmol.* 236:365-374 (1998).

Schmidt-Erfurth et al., "Vascular Targeting in Photodyamic Occlusion of Subretinal Vessels," *Opthalmology* 101:1953-1961 (1994).

Smith et al., "Bacteriochlorophylls c from *Chloropseudomonas ethylicum*. Composition and NMR Studies of the Pheophorbides and Derivatives", Am. Chem. Soc., 102(7):2437-2448 (1980).

Zheng et al., "Chlorin-based symmetrical and unsymmetrical dimers with amide linkages: effect of the substituents on photodynamic and photophysical properties," *J. Chem. Soc. Perkins 1*, pp. 3113-3121 (2000).

Zheng et al., "PDT using a novel LED light source and LS11 in a rat liver model," *30th Annual Meeting of the American Society for Photobiology*; Jul. 13-17, 2002; Quebec City, Canada. American Society for Photobiology: 33 [abstract 95].

US 6,159,469, 12/2000, Choi et al. (withdrawn)

* cited by examiner

MR image of Conjugate 3 injected at 10mmol/kg in rats bearing Word colon tumors.

MR image of Conjugate 7 injected at 10mmol/kg in rats bearing Word colon tumors.

MULTI DTPA CONJUGATED TETRAPYROLLIC COMPOUNDS FOR PHOTOTHERAPEUTIC CONTRAST AGENTS

CROSS REFERENCE TO RELATED APPLICATIONS

This is a continuation-in-part of U.S. patent application Ser. No. 10/390,438 filed Mar. 17, 2003 now U.S. Pat. No. 7,078,014 entitled METHOD FOR USING CHLORIN AND BACTERIOCHLORIN-BASED AMINOPHENYL DTPA AND N2S2 CONJUGATES FOR MR CONTRAST MEDIA AND RADIOPHARMACEUTICALS which in turn is a continuation-in-part of U.S. patent application Ser. No. 09/739,155 filed Dec. 18, 2000 now U.S. Pat. No. 6,534,040 entitled CHLORIN AND BACTERIOCHLORIN-BASED AMINOPHENYL DTPA AND N2S2 CONJUGATES FOR MR CONTRAST MEDIA AND RADIOPHARMACEUTICALS which in turn claims priority from U.S. Provisional Patent Application 60/171,961 filed Dec. 23, 1999 entitled CHLORIN AND BACTERIOCHLORINE-BASED AMINOPHENYL DTPA AND N2S2 CONJUGATES FOR MR CONTRAST MEDIA AND RADIOPHARMACEUTICALS;

And, this is a continuation-in-part of U.S. patent application Ser. No. 11/452,511 to Pandey et al. filed Jun. 14, 2006 now U.S. Pat. No. 7,501,509 entitled WATER SOLUBLE TETRAPYROLLICPHOTOSENSITIZERS FOR PHOTODYNAMIC THERAPY, which is a continuation-in-part of U.S. application Ser. No. 10/607,922 to Pandey et al. filed Jun. 27, 2003 now U.S. Pat. No. 7,166,719 entitled FLUORINATED PHOTOSENSITIZERS RELATED TO CHLORINS AND BACTERIOCHLORINS FOR PHOTODYNAMIC THERAPY which in turn claims priority from Provisional Application Ser. No. 60/392,473 to Pandey et al. filed Jun. 27, 2002 entitled FLUORINATED PHOTOSENSITIZERS RELATED TO CHLORINS AND BACTERIOCHLORINS FOR PHOTODYNAMIC THERAPY.

The above applications are incorporated herein by reference in their entirety.

STATEMENT REGARDING FEDERALLY SPONSORED RESEARCH

This invention was made with government support under Grant Numbers NIH CA 55792 and NIH R21 CA109914 awarded by the National Institute of Health. The government has certain rights in this invention.

BACKGROUND OF THE INVENTION

As described in above priority patent application Ser. No. 10/390,438, an effective tetrapyrollic photosensitizer, e.g. HPPH (a chlorophyll-a derivative) was conjugated with Gd(III)-aminophenyl-DTPA, an imaging agent. In vivo reflection spectroscopy confirmed that tumor uptake of the HPPH-aminophenylDTPA Gd (III) conjugate was higher than that of HPPH alone in the radiation-induced fibrosarcoma (RIF) tumor of $C_3H$ mice. The subcutaneously-implanted Ward colon carcinoma in rats showed markedly increased MRI signal at twenty-four hours after intravenous injection of the conjugate. Both in vitro (RIF tumor cells) and in vivo (mice bearing RIF tumors) the conjugate produced significant efficacy. We have synthesized a molecule [two Gd (III) atoms per HPPH molecule] that also remained tumor-avid, PDT-active, and with improved MRI enhancing ability than the related mono-Gd(III) analog. Unfortunately, at the MRI dose (10 μmole/kg), these conjugates produced severe skin phototoxicity. However, replacing the hexyl-group of the pyropheophorbide-a with a PEG group, produced remarkable tumor enhancing at 8 hour postinjection, significant tumoricidal activity. The poor water-solubility problem of these conjugates was resolved by liposomal formulation.

For many years, in vivo imaging of human organs was largely dependent upon the intravenous administration of radioactive molecules for nuclear scanning or non-radioactive iodinated chemicals for radiography. However, over the last decade magnetic resonance imaging (MRI) has assumed a critical role in imaging. Unlike nuclear scanning, conventional radiography, or even computed tomography, MRI uses contrast enhancers ("contrast media") that contain paramagnetic ions, particularly gadolinium [Gd(III)]. They are not themselves "seen" by the MRI scanner. Rather, they affect the water in body tissue so as to increase its "signal" when placed in a magnetic field. At present, three similar gadolinium(III)-derived MRI contrast agents have been approved for human clinical use in the United States, the bis-N-methylglucamine salt of Gd(III)diethylenetriaminepentaacetic acid (DTPA) (Magnavist), the bis-N-methylamide of Gd(III) DTPA (Omniscan), and the Gd(III) chelate of 20-(2-hydroxypropyl) derivative of 1,4,7,10-tetraazacyclododecane-N,N',N'',N'''-1,4,7-tetraacetic acid (Prohance). All three of these agents are carboxylate containing, water-soluble complexes. After intravenous injection they result in a transient signal increase in the vascular space and penetrate the "leaky" capillary bed of many tumors, but are rapidly excreted through the kidneys by glomerular filtration. Although several liver-specific contrast media have also been created, other organs have not been successfully targeted, and no specific tumor-avid MRI contrast agent is available to date.

Signal Intensity in MRI:

Signal intensity in MRI stems largely from the local value of the longitudinal and transverse relaxation rates of water protons, $1/T_1$, and the transverse rate, $1/T_2$. Signal tends to increase with increasing $1/T_1$ and decrease with increasing $1/T_2$. Pulse sequences that emphasize changes in $1/T_1$ are referred to as "$T_1$-weighted," and the opposite is true for $T_2$-weighted scans. Contrast agents increase both $1/T_1$ and $1/T_2$ to varying degrees, depending on their nature as well as the applied magnetic field. Agents like gadolinium (III) that increase $1/T_1$ and $1/T_2$ by roughly similar amounts are best visualized using $T_1$-weighted images, because the percentage change in $1/T_1$ in tissue is much greater than that in $1/T_2$. The longitudinal and transverse relaxivity values, $r_1$, and $r_2$, refer to the amount of increase in $1/T_1$ and $1/T_2$, respectively, per milimole of agent (often given as per mM of Gd). $T_1$ agents usually have $r_2/r_1$ ratios of 1-2.

Advances in MRI have strongly favored $T_1$ agents and thus gadolinium(III). Faster scans with higher resolution require more rapid radio-frequency pulsing and are thus generally $T_1$-weighted, because MR signal in each voxel becomes saturated. $T_1$ agents relieve this saturation by restoring a good part of the longitudinal magnetization between pulses. At the same time, a good $T_1$ agent would not significantly affect the bulk magnetic susceptibility of the tissue compartment in which it is localized, thus minimizing any inhomogeneities that can lead to image artifacts and/or decreased signal intensity.

The effect of these agents is to increase signal on $T_1$-weighted images that are negatively affected by proton density. The effect on $T_2$-weighed images is to decrease signal, but this effect is minimal, because most of the $T_2$ signal comes from the influence of proton density. Signal Intensity for the Spin Echo Imaging is expressed as:

$$S_{(TE,TR)} = N_{(H)}[1 - 2e^{-(TR - TE/2)/T_1} = e^{-TE/T_1}]e^{-TE/T_2}$$

Conventional clinical MRI units produce static, cross sectional images. Newer "interventional MRI" units allow the operator to continuously image an organ while performing surgery or other manipulations.

Gd(III) is a logical choice for MRI contrast media because of its superior performance compared with other lanthanide ions. Dysprosium(III) and holmium(III) have larger magnetic moments than that of Gd(III), but the asymmetry of their electronic states leads to very rapid electron spin relaxation. The symmetric S-state of Gd(III) is a more hospitable environment for electron spins, leading to a much slower electronic relaxation rate. In the process that gives rise to relaxivity, water protons hardly feel the effects of ions like Dy(III), much like a leaf near the rapid wings of hummingbird; Gd(III) electrons, on the other hand, are more closely in tune with the proton's frequency.

A key biological factor that influences the selection of gadolinium compounds for human use is that its ligands like DTPA circulate and are excreted intact. The metal ion is "buried" in the chelation cage and will not bind to donor groups of proteins and enzymes. This in vivo stability markedly reduces the potential for toxicity from free gadolinium.
Tetrapyrrole-Based Compounds as MRI Agents:

The porphyrins and related tetrapyrrolic systems are among the most widely studied of all macrocyclic compounds. In fact, in one capacity or another these versatile molecules have influenced nearly all disciplines in chemistry. The concentration of certain porphyrins and related tetrapyrrolic or expanded porphyrin-type compounds is much higher in malignant tumors than in most normal tissues. A few years ago Sessler and coworkers discovered a new class of expanded porphyrins that is based on the Schiff base condensation between a diformyl-tripyrrane and an aromatic 1,2-diamine. This new class of expanded porphyrins has come to be known as the "texaphyrins". Compared to the natural porphyrin system, the texaphyrins possess a larger core size and thus have the capability to form complexes with certain lanthanides, including gadolinium(III). Gd(III) texaphyrin is currently under phase I/II human clinical trials as a tumor-avid MRI contrast agent.

Some tetrapyrrole-based compounds are effective photosensitizers for cancer treatment by photodynamic therapy [PDT]. Although PDT is sometimes considered a novel, idiosyncratic therapy, it has in fact been effective in a wide variety of malignancies, including skin, lung, bladder, head and neck, breast, and esophagus. The precise mechanism(s) of PDT are unknown; however, in vitro studies suggest that singlet oxygen production is phototoxic when the photosensitizing agent encounters light. In vivo animal data suggest that tumor vasonecrosis may be the direct cause of tumor kill.

Effective PDT requires delivery of light to tumor that has absorbed a photosensitizer previously delivered by the systemic circulation after peripheral intravenous injection. Superficial visible lesions, or those that are endoscopically accessible—e.g., endobronchial or esophageal—are easily treated, but the vast majority of malignant lesions are too deep to be reached by light of the wavelength required to trigger singlet oxygen production in the current generation of photosensitizers. Although the technology to deliver therapeutic light to deep lesions via thin transmission fibers "capped" by a terminal diffuser is well-developed, a deep lesion is by definition not visible from the skin surface, and its uptake of a peripherally-injected photosensitizer is unknown; therefore, PDT of deep tumors thus far been impractical.

A relatively long-wavelength absorbing photosensitizer, the 3-(1-hexyloxy)ethyl derivative of pyropheophorbide-a 1 [HPPH], developed in our laboratory, is tumor-avid and currently in Phase VIII clinical trials at The Roswell Park Cancer Institute. We investigated this compound as a "vehicle" for delivering gadolinium complexes to tumor, with the goal of creating the first single compound that would function both as an MRI tumor-avid contrast medium and a photosensitizer for cancer therapy. [Gd(III) texaphrin is not a photosensitizer, because it does not produce singlet oxygen when exposed to light].

BRIEF DESCRIPTION OF THE INVENTION

Figure 1A:
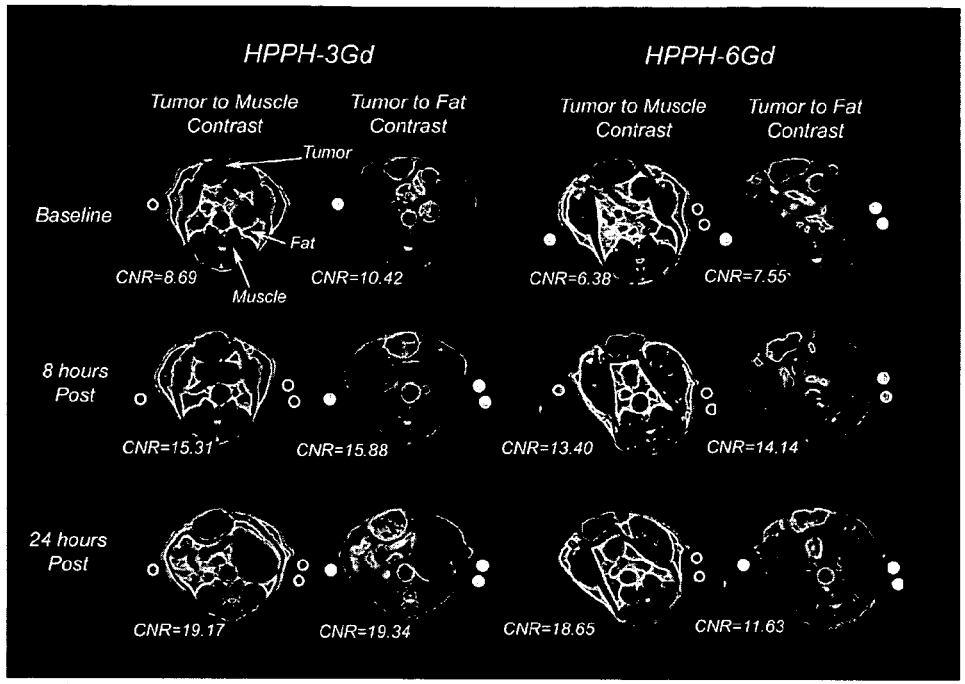
FIG. 1A shows MRI images of tumors as compared to muscle using conjugate 3.

The present invention deals with the synthesis of "higher pay-load' contrast agents in which the photosensitizers are conjugated with three- and six Gd(III)DTP molecules. In contrast to conjugates with mono- and di-DTPA conjugates which were formulated in Tween 80/water and liposomal formulation, the conjugates with three- and six DTPA molecules can be formulated in phosphate buffer at 7.4 pH and show the potential for tumor imaging ability and phototoxicity. The development of a tumor-avid contrast medium for MRI would by itself represent an important step in the diagnosis of cancer, but a dual function agent presents the potential for a diagnostic body scan followed by targeted photodynamic therapy, combining two modalities into a single cost-effective "see and treat" approach.

The invention includes both the novel tetrapyrollic water soluble photosensitizing and imaging compounds and the methods of treating and imaging hyperproliferative tissue, e.g. tumors and hypervacularized tissue such as found in macular degeneration. Broadly, the compounds are tetrapyrollic photosensitizer compounds where the tetrapyrollic compound is a chlorin, bacteriochlorin, porphyrin, pyropheophorbide, purpurinimide, or bacteriopurpurinimide having 3 to 6 —$CH_2CONHphenylCH_2CH(N(CH_2COOH)_2))(CH_2N(CH_2COOH)(CH_2CH_2N(CH_2COOH)_2))$ groups or esters thereof or complexes thereof with gadolinium(III).

Preferably, the compound has at least one pendant —$CH_2CH_2CONHC(CH_2CH_2CONHphenylCH_2CH(N(CH_2COOH)_2))(CH_2N(CH_2COOH)(CH_2CH_2N(CH_2COOH)_2)))_3$ group or esters thereof or complexes thereof with gadolinium (III).

Preferred compounds of the invention have the formula:

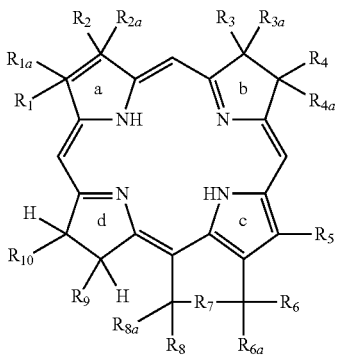

or a pharmaceutically acceptable derivative thereof, wherein:

$R_1$ and $R_2$ are each independently substituted or unsubstituted alkyl, substituted or unsubstituted alkenyl, —C(O)$R_a$ or —COOR$_a$ or —CH(CH$_3$)(OR) or —CH(CH$_3$)(O(CH$_2$)$_n$XR) where $R_a$ is hydrogen, substituted or unsubstituted alkyl, substituted or unsubstituted alkenyl, substituted or unsubstituted alkynyl, or substituted or unsubstituted cycloalkyl where $R_2$ may be CH=CH$_2$, CH(OR$_{20}$)CH$_3$, C(O)Me, C(=NR$_{21}$)CH$_3$ or CH(NHR$_{21}$)CH$_3$;

where X is an aryl or heteroaryl group;

n is an integer of 0 to 6;

R and R' are independently H or lower alkyl of 1 through 8 carbon atoms;

where $R_{20}$ is methyl, butyl, heptyl, docecyl or 3,5-bis(trifluoromethyl)-benzyl; and $R_{21}$, is 3,5,-bis(trifluoromethyl)benzyl;

$R_{1a}$ and $R_{2a}$ are each independently hydrogen or substituted or unsubstituted alkyl, or together form a covalent bond;

$R_3$ and $R_4$ are each independently hydrogen or substituted or unsubstituted alkyl;

$R_{3a}$ and $R_{4a}$ are each independently hydrogen or substituted or unsubstituted alkyl, or together form a covalent bond;

$R_5$ is hydrogen or substituted or unsubstituted alkyl;

$R_6$ and $R_{6a}$ are each independently hydrogen or substituted or unsubstituted alkyl, or together form =O;

$R_7$ is a covalent bond, alkylene, azaalkyl, or azaaraalkyl or =NR$_{20}$ where $R_{20}$ is hydrogen or lower alkyl of 1 through 8 carbon atoms or —CH$_2$-3,5-bis(tri-fluoromethyl)benzyl or —CH$_2$X—R$^1$ or —YR$^1$ where Y is an aryl or heteroaryl group;

$R_8$ and $R_{8a}$ are each independently hydrogen or substituted or unsubstituted alkyl or together form =O;

$R_9$ is a pendant group containing 3 through 6 —CH$_2$CONHphenylCH$_2$CH(N(CH$_2$COOH)$_2$))—(CH$_2$N(CH$_2$COOH)(CH$_2$CH$_2$N(CH$_2$COOH)$_2$)) groups or esters thereof or complexes thereof with gadolinium(III).

$R_{10}$ is hydrogen, or substituted or unsubstituted alkyl and;

each of $R_1$-$R_{10}$, when substituted, is substituted with one or more substituents each independently selected from Q, where Q is alkyl, haloalkyl, halo, pseudohalo, or —COOR$_b$ where $R_b$ is hydrogen, alkyl, alkenyl, alkynyl, cycloalkyl, aryl, heteroaryl, araalkyl, or OR$_c$ where $R_c$ is hydrogen, alkyl, alkenyl, alkynyl, cycloalkyl, or aryl or CONR$_d$R$_e$ where $R_d$ and $R_e$ are each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or =NR$_h$ where $R_h$ is hydrogen, alkyl, alkenyl, alkynyl, cycloalkyl, or aryl, or is an amino acid residue;

each Q is independently unsubstituted or is substituted with one or more substituents each independently selected from $Q_1$, where $Q_1$ is alkyl, haloalkyl, halo, pseudohalo, or —COOR$_b$ where $R_b$ is hydrogen, alkyl, alkenyl, alkynyl, cycloalkyl, aryl, heteroaryl, araalkyl, or OR$_c$ where $R_c$ is hydrogen, alkyl, alkenyl, alkynyl, cycloalkyl, or aryl or CONR$_d$R$_e$ where $R_d$ and $R_e$ are each independently hydrogen, alkyl, alkenyl, alkynyl, cycloalkyl, or aryl, or NR$_f$R$_g$ where $R_f$ and $R_g$ are each independently hydrogen, alkyl, alkenyl, alkynyl, cycloalkyl, or aryl, or =NR$_h$ where $R_h$ is hydrogen, alkyl, alkenyl, alkynyl, cycloalkyl, or aryl, or is an amino acid residue.

$R_9$ is preferably a —CH$_2$CH$_2$CONHC(CH$_2$CH$_2$CONHphenylCH$_2$CH(N(CH$_2$COOH)$_2$))—(CH$_2$N(CH$_2$COOH)(CH$_2$CH$_2$N(CH$_2$COOH)$_2$)))$_3$ group or esters thereof or complexes thereof with gadolinium(III).

DETAILED DESCRIPTION OF THE INVENTION

A compound in accordance with the present invention that effectively functions both as an MRI contrast medium and a photosensitizer creates an entirely new paradigm for tumor diagnosis and therapy. After peripheral intravenous injection of this compound, a patient could be scanned with interventional MRI. The tumor site(s) could thus be defined, and, while the patient remains in the scanner, an interventional radiologist could transcutaneously insert ultra-slim needles acting as introducers for light-transmission fibers into the lesion(s). Because such fiber diameters can be small, e.g. only 400 microns, the introducer needles would produce negligible tissue damage. A light source can be coupled to the fibers, and PDT of the lesion(s) can commence, without any significant injury to other organs. Because the same molecule represents the contrast medium and the therapeutic medium, the lesion(s) can be continuously imaged during needle/fiber placement, without any ambiguity in location or "misregistration" of separate diagnostic/therapeutic images. This paradigm makes the low-toxicity and high efficacy of PDT available to virtually any location from the skull base to the floor of the pelvis.

Examples of compounds for use in accordance with the present invention were prepared and tested. Synthetic intermediates and the final products were characterized by NMR (400 MHz), mass spectrometry (EIMS & HRMS) and elemental analyses. $^1$H NMR spectra were recorded on a Bruker AM-400 spectrometer. Chemical shifts are expressed in ppm. All photo physical experiments were carried out using spectroscopic grade solvents. The reactions were monitored by TLC and/or spectrophotometrically. Column chromatography was performed either over Silica Gel 60 (70-230 mesh) or neutral Alumina (Brockmann grade III, 50 mesh). UV-visible spectrums were recorded on Varian Cary 50 Bio UV-visible spectrophotometer using dichloromethane as solvent unless other wise specified.

Compound No. 1:

HPPH (100.0 mg, 0.157 mmol), amine A (97.8 mg, 0.235 mmol), EDCI (60.2 mg, 0.314 mmol) and DMAP (38.36 mg, 0.314 mmol) were taken in a dry RBF (100 ml). Dry dichloromethane (30 ml) was added to it and reaction mixture was stirred at RT for 16 hr under N$_2$ atm. Reaction mixture was diluted with dichloromethane (100 ml), washed with brine solution, organic layer separated, dried over sodium sulfate and concentrated. Crude mixture was chromatographed over silica gel using 1-3% Methanol/Dichloromethane mixture as eluent to give product 1. Yield: 130.0 mg (80.0%). UV-vis ($\lambda$max cm$^{-1}$, dichloromethane): 318, 412, 506, 537, 604 & 660. $^1$HNMR (400 MHz, CDCl$_3$): $\delta$ 9.78 (s, 1H, H-5), 9.41 (s, 1H, H-10), 8.54 (s, 1H, H-20), 5.96-5.91 (m, 2H, CH$_3$CHOhexyl, NH), 5.33 (d, 1H, CH-15$^1$, J=19.6 Hz), 5.14 (d, 1H, CH-15$^1$, J=19.6 Hz), 4.53 (q, 1H, H-17, J=7.2 Hz), 4.32 (m, 1H, H-18), 3.71-3.67 (m, 2H, —OCH$_2$-hexyl), 3.63-3.60 (m, 2H, 8-CH$_2$CH$_3$), 3.52 (s, 3H, 7-CH$_3$), 3.39 (s, 3H, 2-CH$_3$), 3.27 (s, 3H, 12-CH$_3$), 2.67 (m, 1H, CH-17$^2$), 2.37 (m, 1H, H-17$^2$), 2.26 (m, 1H, H-17$^1$), 2.15-2.13 (m, 9H, 3CH$_2$-chain & CH$_3$CHOhexyl), 1.97 (m, 1H, H-17$^1$), 1.92 (t, 6H, 3CH$_2$-chain, J=7.6 Hz), 1.80 (d, 3H, 18-CH$_3$, J=7.2 Hz), 1.73 (m, 2H, CH$_2$hexyl), 1.66 (t, 3H, 8-CH$_2$CH$_3$, J=7.6 Hz), 1.44 (m, 2H, CH$_2$hexyl), 1.30 (s, 27H, 3CO$_2^t$Bu), 1.24 (m, 4H, 2CH$_2$hexyl), 0.78 (t, 3H, CH$_3$hexyl, J=6.8 Hz), 0.04 (brs, 1H, NH), −1.68 (brs, 1H, NH).

EIMS: 1035 (MH$^+$).

Compound No. 2:

Compound 1 (73.0 mg, 0.07 mmol) was stirred with 70% TFA/DCM (5.0 ml) at RT for 3 hr. Resultant mixture was concentrated and dried under high vacuum to remove trace of TFA. To this crude were added, amino-benzyl-DTPA-penta-tert-butyl ester (219.0 mg, 0.282 mmol), EDCI (67.0 mg, 0.352 mmol) and DMAP (43.0 mg, 0.352 mmol). Dry dichloromethane (30 ml) was added to it and reaction mixture was stirred at RT for 16 hr under N$_2$ atm. Reaction mixture was diluted with dichloromethane (100 ml), washed with brine solution, organic layer separated, dried over sodium sulfate and concentrated. Crude mixture was chromatographed over alumina G (III) using 1-3% Methanol/Dichloromethane mixture as eluent to give product 2. Yield: 130.0 mg (58.47%). UV-vis ($\lambda$max cm$^{-1}$, dichloromethane): 319, 411, 506, 537, 604, 661. $^1$HNMR (400 MHz, CDCl$_3$): $\delta$ 9.74 (splitted s, 1H, H-5), 9.36 (splitted s, 1H, H-10), 8.54 (splitted s, 1H, H-20), 8.17 (brs, 1H, NH), 7.74 (m, 1H, Ph-DTPA), 7.61-7.56 (m, 2H, Ph-DTPA), 7.43 (m, 4H, Ph-DTPA), 7.12 (m, 5H, Ph-DTPA), 6.96 (brs, 1H, NH), 5.96 (m, 1H, CH$_3$CHOhexyl), 5.29 (d, 1H, CH-15$^1$, J=19.2 Hz), 5.11 (d, 1H, CH-15$^1$, J=19.2 Hz), 4.47 (m, 1H, H-17), 4.26 (m, 1H, H-18), 3.64 (m, 2H, & OCH$_2$hexyl), 3.54 (m, 2H, 8-CH$_2$CH$_3$), 3.45-3.38 (m, 30H, 15CH$_2$-DTPA), 3.36 (s, 3H, 7-CH$_3$), 3.32 (s, 3H, 2-CH$_3$), 3.22 (s, 3H, 12-CH$_3$), 3.12 (m, 3H, CH-DTPA), 2.84-2.70 (m, 19H, 9CH$_2$-DTPA & CH-17$^2$), 2.59 (m, 6H, 6CH$_2$-benzyl), 2.47-2.41 (m, 8H, 3CH$_2$-chain, CH-17$^2$ & CH-17$^1$), 2.19-2.15 (m, 9H, 3CH$_2$-chain, CH$_3$CH-Ohexyl), 2.06 (d, 3H, 18-CH$_3$, J=7.6 Hz) 2.00 (m, 1H, CH-17$^1$), 1.74 (m, 4H, 2CH$_2$-hexyl), 1.66 (t, 3H, 8-CH$_2$CH$_3$, J=7.2 Hz), 1.60 (m, 135H for 15 CO$_2^t$Bu), 1.26 (m, 4H, 2CH$_2$-hexyl), 0.77 (m, 3H, CH$_3$-Ohexyl), 0.55 (brs, 1H, NH), −0.24 (brs, 1H, NH). HRMS: Calculated for C$_{172}$H$_{267}$N$_{17}$O$_{36}$: 3149.053, found: 3150.10 (MH$^+$).

Compound No. 3:

Compound 2 (110.0 mg, 0.034 mmol) was stirred with 70% TFA/DCM (5.0 ml) at RT for 3 hr. Resultant mixture was concentrated and dried under high vacuum to remove trace of TFA. The crude thus obtained was dissolved in pyridine (10 ml) and put under stirring, to this stirring solution GdCl$_3$.6H$_2$O (77.9 mg, 0.21 mmol) in 1 ml of water was added slowly and resultant mixture was stirred for 16 hr. Reaction mixture was concentrated to dryness under high vacuum. Residue was washed with water (10 ml×3), acetone (10 ml×3) and finally dried under high vacuum using P$_2$O$_5$ as drying agent. Yield: 75.0 mg (77.55%). UV-vis ($\lambda$max cm$^{-1}$, MeOH): 620, 408, 504, 537, 604 & 660. Elemental analysis: Calculated for C$_{113}$H$_{151}$Gd$_3$N$_{17}$O$_{36}$: C, 48.55; H, 5.44; Gd, 16.88; N, 8.52; O, 20.61. found: C, 48.68; H, 5.49; N, 8.57.

Compound No. 5:

Acid 4 (100.0 mg, 0.143 mmol), amine A (89.1 mg, 0.214 mmol), EDCI (54.9 mg, 0.28 mmol) and DMAP (34.9 mg, 0.28 mmol) were taken in a dry RBF (100 ml). Dry dichloromethane (30 ml) was added to it and reaction mixture was stirred at RT for 16 hr under N$_2$ atm. Reaction mixture was diluted with dichloromethane (100 ml), washed with brine solution, organic layer separated, dried over sodium sulfate and concentrated. Crude mixture was chromatographed over silica gel using 1-2% Methanol/Dichloromethane mixture as eluent to give product 5. Yield: 134.0 mg (85.3%). UV-vis ($\lambda$max cm$^{-1}$, dichloromethane): 318, 411, 506, 536, 604 & 661. $^1$HNMR (400 MHz, CDCl$_3$): $\delta$ 9.76 (splitted s, 1H, H-5), 9.38 (splitted s, 1H, H-10), 8.55 (s, 1H, H-20), 6.02 (d, 1H, CH$_3$CHOOTEG, J=6.4 Hz), 5.99 (brs, 1H, NH), 5.34 (d, 1H, CH-15$^1$, J=20.0 Hz), 5.15 (d, 1H, CH-15$^1$, J=20.0 Hz), 4.58 (q, 1H, H-17, J=6.8 Hz), 4.33 (m, 1H, H-18), 3.88-3.75 (m, 4H, 2CH$_2$—O-TEG), 3.70-3.62 (m, 6H, 3CH$_2$—O-TEG), 3.55 (m, 2H, 8-CH$_2$CH$_3$), 3.47-3.44 (m, 2H, CH$_2$—O-TEG), 3.40 (s, 3H, 7-CH$_3$), 3.39 (s, 3H, 2-CH$_3$), 3.29 (s, 3H, 12-CH$_3$), 3.27 (s, 3H, CH$_3$—O-TEG), 2.69 (m, 1H, CH-17$^2$), 2.39 (m, 1H, CH-17$^2$), 2.31 (m, 1H, CH-17$^1$), 2.14 (m, 8H, 4CH$_2$-chain), 2.00 (m, 1H, CH-17$^1$), 1.92 (m, 7H, 2CH$_2$-chain, CH$_3$CHOTEG), 1.82 (d, 3H, 18-CH$_3$, J=7.2 Hz), 1.68 (t, 3H, 8-CH$_2$CH$_3$, J=7.6 Hz), 1.31 (s, 27H, 3CO$_2^t$Bu), 0.42 (brs, 1H, NH), −1.69 (brs, 1H, NH). EIMS: 1097 (MH$^+$)

Compound No. 6:

Compound 5 (100.0 mg, 0.091 mmol) was stirred with 80% TFA/DCM (5.0 ml) at RT for 3 hr. Resultant mixture was concentrated and dried under high vacuum to remove trace of TFA. To this crude were added, amino-benzyl-DTPA-penta-tert-butyl ester (285.0 mg, 0.365 mmol), EDCI (105.0 mg, 0.54 mmol) and DMAP (66.8 mg, 0.54 mmol). Dry dichloromethane (30 ml) was added to it and reaction mixture was stirred at RT for 16 hr under N$_2$ atm. Reaction mixture was diluted with dichloromethane (100 ml), washed with brine solution, organic layer separated, dried over sodium sulfate and concentrated. Crude mixture was chromatographed over alumina G (III) using 1-3% Methanol/Dichloromethane mixture as eluent to give product 6. Yield: 250.0 mg (85.3%). UV-vis ($\lambda$max cm$^{-1}$, dichloromethane): 319, 411, 506, 537, 606, 661. $^1$HNMR (400 MHz, CDCl$_3$): $\delta$ 9.70 (splitted s, 1H, H-5), 9.44 (splitted s, 1H, H-10), 9.37 (brs, 1H, NH), 9.20 (brs, 1H, NH), 8.56 (m, 1H, NH), 8.47 (s, 1H, H-20), 7.77 (m, 1H, Ph-DTPA), 7.59 (m, 2H, Ph-DTPA), 7.44 (m, 2H, Ph-DTPA), 7.10 (m, 6H, Ph-DTPA), 6.81 (m, 1H, Ph-DTPA), 5.97 (m, 1H, CH$_3$CHOTEG), 5.20 (m, 2H, CH$_2$-15$^1$), 4.60 (m, 1H, H-17), 4.22 (m, 1H, H-18), 3.81-3.64 (m, 4H, 2CH$_2$—OTEG), 3.57-3.50 (m, 4H, 8-CH$_2$CH$_3$, CH$_2$—OTEG), 3.60 (m, 6H, 3CH$_2$OTEG), 3.38 (s, 30H, 15CH$_2$-DTPA), 3.35 (s, 3H, 7-CH$_3$), 3.23 (m, 6H, 12-CH$_3$, OCH$_3$-TEG), 3.04 (m, 3H, 3CH-DTPA), 2.70 (m, 19H, 9CH$_2$-DTPA, CH-17$^2$), 2.55 (m, 7H, 3CH$_2$-benzyl & CH-17$^2$), 2.32 (t, 6H, 3CH$_2$-chain, J=6.8 Hz), 2.23 (m, 1H, CH-17$^1$), 2.10 (d, 3H, CH$_3$CH-OTEG, J=6.4 Hz), 2.01 (m, 1H, CH-17$^1$), 1.77 (d, 3H, 18-CH$_3$, J=7.2 Hz), 1.68 (t, 3H, 8-CH$_2$CH$_3$, J=7.6 Hz), 1.59 (t, 3H, 6CH$_2$-chain, J=6.4 Hz), 1.44 (m, 135H, 15CO$_2^t$Bu), −1.75 (brs, 1H, NH).

HRMS: Calculated for $C_{173}H_{269}N_{17}O_{39}$: 3211.077, found: 3212.20 ($MH^+$).

Compound No. 7:

Compound 6 (226.0 mg, 0.07 mmol) was stirred with 80% TFA/DCM (5.0 ml) at RT for 3 hr. Resultant mixture was concentrated and dried under high vacuum to remove trace of TFA. The crude thus obtained was dissolved in pyridine (10 ml) and put under stirring, to this stirring solution $GdCl_3.6H_2O$ (156.9 mg, 0.422 mmol) in 1 ml of water was added slowly and resultant mixture was stirred for 16 hr. Reaction mixture was concentrated to dryness under high vacuum. Residue was washed with water (10 ml×3), acetone (10 ml×3) and finally dried under high vacuum using $P_2O_5$ as drying agent. Yield: 165.0 mg (82.5%). UV-vis ($\lambda$max $cm^{-1}$, MeOH): 320, 408, 505, 537, 605 & 660. Elemental analysis: Calculated for $C_{113}H_{149}Gd_3N_{17}O_{39}$: C, 47.77; H, 5.29; Gd, 16.60; N, 8.38; O, 21.96. found: C, 47.85; H, 5.30; N, 8.43.

Compound No. 9:

Acid 8 (82.0 mg, 0.118 mmol), amine A (73.6 mg, 0.177 mmol), EDCI (45.3 mg, 0.236 mmol) and DMAP (28.8 mg, 0.236 mmol) were taken in a dry RBF (100 ml). Dry dichloromethane (30 ml) was added to it and reaction mixture was stirred at RT for 16 hr under $N_2$ atm. Reaction mixture was diluted with dichloromethane (100 ml), washed with brine solution, organic layer separated, dried over sodium sulfate and concentrated. Crude mixture was chromatographed over silica gel using 1-2% Methanol/Dichloromethane mixture as eluent to give product 9. Yield: 90.0 mg (69.8%). UV-vis ($\lambda$max $cm^{-1}$, dichloromethane): 365, 418, 509, 545 & 699. $^1$HNMR (400 MHz, $CDCl_3$): δ 9.75 (splitted s, 1H, meso-H), 9.64 (s, 1H, meso-H), 8.55 (s, 1H, meso-H), 6.25 (m, 1H, CONH), 5.79 (q, 1H, $CH_3\underline{CH}$Obutyl, J=6.4 Hz), 5.34 (m, 1H, H-17), 4.52 (t, 2H, —$N\underline{CH_2}$butyl, J=7.2 Hz), 4.42 (m, 1H, H-18), 3.84 (s, 3H, ring-$\underline{CH_3}$), 3.70-3.59 (m, 4H, —$O\underline{CH_2}$-butyl, 8-$\underline{CH_2}CH_3$), 3.32 (s, 3H, ring-$CH_3$), 3.17 (s, 3H, ring-$CH_3$), 2.61 (m, 1H, CH-$17^2$), 2.43 (m, 1H, H-$17^2$), 2.27 (m, 1H, H-$17^1$), 2.20 (t, 6H, $3CH_2$-chain, J=7.2 Hz), 2.06 (m, 3H, $\underline{CH_3}$CHObutyl), 2.01 (t, 6H, $3\underline{CH_2}$-chain, J=7.6 Hz), 1.82 (m, 1H, H-$17^1$), 1.75 (d, 3H, 18-$CH_3$, J=6.0 Hz), 1.68 (t, 3H, 8-$CH_2\underline{CH_3}$, J=7.6 Hz), 1.62 (m, 8H, $4\underline{CH_2}$butyl), 1.34 (s, 27H, $3CO_2{}^t$Bu), 1.10 (t, 3H, $\underline{CH_3}$-obutyl, J=7.2 Hz), 0.87 (t, 3H, $\underline{CH_3}$-Nbutyl, J=7.2 Hz), 0.40 (brs, 1H, NH), −0.06 (brs, 1H, NH). EIMS: 1092 ($MH^+$).

Compound No. 10:

Compound 9 (80.0 mg, 0.073 mmol) was stirred with 70% TFA/DCM (5.0 ml) at RT for 3 hr. Resultant mixture was concentrated and dried under high vacuum to remove trace of TFA. To this crude were added, amino-benzyl-DTPA-penta-tert-butyl ester (286.0 mg, 0.366 mmol), EDCI (84.4 mg, 0.44 mmol) and DMAP (53.7 mg, 0.44 mmol). Dry dichloromethane (30 ml) was added to it and reaction mixture was stirred at RT for 16 hr under $N_2$ atm. Reaction mixture was diluted with dichloromethane (100 ml), washed with brine solution, organic layer separated, dried over sodium sulfate and concentrated. Crude mixture was chromatographed over alumina G (III) using 1-3% Methanol/Dichloromethane mixture as eluent to give product 10. Yield: 140.0 mg (59.57%). UV-vis ($\lambda$max $cm^{-1}$, dichloromethane): 365, 418, 509, 546, 699. $^1$HNMR (400 MHz, $CDCl_3$): δ 9.75 (splitted s, 1H, meso-H), 9.63 (splitted s, 1H, meso-H), 9.33 (brs, 1H, NH), 8.60 (splitted s, 1H, meso-H), 7.61 (m, 2H, Ph-DTPA), 7.58 (m, 1H, Ph-DTPA), 7.37 (m, 3H, Ph-DTPA), 7.12 (m, 5H, Ph-DTPA), 6.84 (m, 1H, Ph-DTPA), 5.76 (m, 1H, $CH_3\underline{CH}$Obutyl), 5.39 (m, 1H, H-17), 4.45 (m, 3H, H-18 & $N\underline{CH_2}$butyl), 3.82 (s, 3H, ring-$CH_3$), 3.65 (m, 4H, 8-$\underline{CH_2}CH_3$ & $O\underline{CH_2}$butyl), 3.38 (m, 22H, $11CH_2$-DTPA), 3.31 (m, 11H, $4CH_2$-DTPA & ring-$CH_3$), 3.17 (s, 3H, ring-$CH_3$), 3.03 (m, 3H, CH-DTPA), 2.84-2.61 (m, 19H, $9CH_2$-DTPA & CH-$17^2$), 2.47 (m, 8H, $6CH_2$-benzyl & CH-$17^2$ & CH-$17^1$), 2.20 (m, 6H, $3CH_2$-chain), 2.04 (d, $\underline{CH_3}$CHObutyl, J=6.8 Hz), 1.96 (m, 6H, $3CH_2$-chain), 1.84 (m, 1H, CH-$17^1$), 1.73 (s, 3H, 17-$CH_3$), 1.67 (t, 3H, 8-$CH_2\underline{CH_3}$, J=7.2 Hz), 1.60 (m, 4H, $2CH_2$—Obutyl), 1.41 (m, 135H for 15 $CO_2{}^t$Bu), 1.37 (m, 4H, $2CH_2$—N-butyl), 1.03 (t, 3H, $CH_3$—Obutyl, J=6.8 Hz), 0.86 (t, 3H, $CH_3$—N-butyl, J=6.8 Hz), −0.09 (brs, 1H, NH). HRMS: Calculated for $C_{174}H_{270}N_{18}O_{37}$: 3206.104, found: 3207.250 ($MH^+$).

Compound No. 11:

Compound 10 (130.0 mg, 0.04 mmol) was stirred with 70% TFA/DCM (5.0 ml) at RT for 3 hr. Resultant mixture was concentrated and dried under high vacuum to remove trace of TFA. The crude thus obtained was dissolved in pyridine (10 ml) and put under stirring, to this stirring solution $GdCl_3.6H_2O$ (90.3 mg, 0.243 mmol) in 1 ml of water was added slowly and resultant mixture was stirred for 16 hr. Reaction mixture was concentrated to dryness under high vacuum. Residue was washed with water (10 ml×3), acetone (10 ml×3) and finally dried under high vacuum using $P_2O_5$ as drying agent. Yield: 80.0 mg (69.9%). UV-vis ($\lambda$max $cm^{-1}$, MeOH): 364, 415, 546 & 700. Elemental analysis: Calculated for $C_{114}H_{150}Gd_3N_{18}O_{37}$: C, 48.28; H, 5.33; Gd, 16.63; N, 8.89; O, 20.87. found: C, 48.14; H, 5.40; N, 8.93.

Compound No. 12:

HPPH (100.0 mg, 0.157 mmol), Di-tert-butyl iminodiacetate (77.0 mg, 0.314 mmol), EDCI (60.2 mg, 0.314 mmol) and DMAP (38.36 mg, 0.314 mmol) were taken in a dry RBF (100 ml). Dry dichloromethane (30 ml) was added to it and reaction mixture was stirred at RT for 16 hr under $N_2$ atm. Reaction mixture was diluted with dichloromethane (100 ml), washed with brine solution, organic layer separated, dried over sodium sulfate and concentrated. Crude mixture was chromatographed over silica gel using 1-1.5% Methanol/Dichloromethane mixture as eluent to give product 12. Yield: 120.0 mg (88.3%). UV-vis ($\lambda$max $cm^{-1}$, dichloromethane): 317, 411, 506, 538, 605 & 660. $^1$HNMR (400 MHz, $CDCl_3$): δ 9.80 (s, 1H, H-5), 9.51 (s, 1H, H-10), 8.55 (s, 1H, H-20), 5.94 (q, 1H, $CH_3\underline{CH}$Ohexyl, J=6.4 Hz), 5.33 (d, 1H, CH-$15^1$, J=20.0 Hz), 5.17 (d, 1H, CH-$15^1$, J=20.0 Hz), 4.52 (q, 1H, H-17, J=7.6 Hz), 4.41 (m, 1H, H-18), 4.04 (m, 2H, $CH_2$chain), 3.75 (m, 2H, —$O\underline{CH_2}$-hexyl), 3.67 (s, 3H, 7-$CH_3$), 3.62 (m, 2H, 8-$\underline{CH_2}CH_3$), 3.42 (s, 3H, 2-$CH_3$), 3.37 (m, 2H, $CH_2$chain), 3.29 (s, 3H, 12-$CH_3$), 2.77 (m, 1H, CH-$17^2$), 2.46 (m, 1H, CH-$17^2$), 2.16 (m, 1H, CH-$17^1$), 2.13 (m, 3H, & $\underline{CH_3}$CHOhexyl), 1.97 (m, 1H, CH-$17^1$), 1.84 (d, 3H, 18-$CH_3$, J=7.2 Hz), 1.78 (m, 2H, $CH_2$hexyl), 1.72 (t, 3H, 8-$CH_2\underline{CH_3}$ J=7.6 Hz), 1.49 (s, 9H, $CO_2{}^t$Bu), 1.46 (m, 2H, $CH_2$hexyl), 1.45 (s, 9H, $CO_2{}^t$Bu), 1.25 (m, 4H, $2CH_2$hexyl), 0.8 (t, 3H, $CH_3$hexyl, J=6.8 Hz), 0.42 (brs, 1H, NH), −1.7 (brs, 1H, NH). EIMS: 865 ($MH^+$).

Compound No. 13:

Compound 12 (120.0 mg, 0.139 mmol) was stirred with 70% TFA/DCM (5.0 ml) at RT for 3 hr. Resultant mixture was concentrated and dried under high vacuum to remove trace of TFA. To this crude were added, amine A (144.2 mg, 0.34 mmol), EDCI (106.6 mg, 0.556 mmol) and DMAP (67.8 mg, 0.556 mmol). Dry dichloromethane (30 ml) was added to it and reaction mixture was stirred at RT for 16 hr under $N_2$ atm. Reaction mixture was diluted with dichloromethane (100 ml), washed with brine solution, organic layer separated, dried over sodium sulfate and concentrated. Crude mixture was chromatographed over silica gel using 2-6% Methanol/Dichloromethane mixture as eluent to give product 13. Yield: 190.0 mg (88.3%). UV-vis ($\lambda$max cm$^{-1}$, dichloromethane): 318, 411, 506, 537, 605 and 660. $^1$HNMR (400 MHz, CDCl$_3$): $\delta$ 9.78 (s, 1H, H-5), 9.52 (s, 1H, H-10), 8.3 (s, 1H, H-20), 8.27 (brs, 1H, NH), 8.17 (brs, 1H, NH), 6.59 (brs, 1H, NH), 5.90 (m, 1H, CH$_3$CHOhexyl), 5.34 (d, 1H, CH-15$^1$, J=20.0 Hz), 5.15 (d, 1H, CH-15$^1$, J=20.0 Hz), 4.53 (q, 1H, H-17, J=6.0 Hz), 4.36 (m, 1H, H-18), 3.77 (m, 2H, —OCH$_2$-hexyl), 3.69 (m, 2H, 8-CH$_2$CH$_3$), 3.67 (s, 3H, 7-CH$_3$), 3.61 (m, 4H, 2CH$_2$chain), 3.36 (s, 3H, 2-CH$_3$), 3.26 (s, 3H, 12-CH$_3$), 2.77 (m, 1H, CH-17$^2$), 2.66 (m, 1H, CH-17$^2$), 2.52 (m, 1H, CH-17$^1$), 2.23 (m, 12H, 6CH$_2$-chain), 2.11 (d, 3H, CH$_3$CHOhexyl, J=6.4 Hz), 2.07 (m, 6H, 3CH$_2$-chain), 1.95 (m, 6H, 3CH$_2$-chain), 1.93 (m, 1H, CH-17$^1$), 1.81 (d, 3H, 18-CH$_3$, J=7.2 Hz), 1.75 (m, 2H, CH$_2$hexyl), 1.71 (t, 3H, 8-CH$_2$CH$_3$, J=8.0 Hz), 1.43 (m, 2H, CH$_2$hexyl), 1.41 (s, 27H, 3CO$_2^t$Bu), 1.32 (s, 27H, 3CO$_2^t$Bu), 1.24 (m, 4H, 2CH$_2$hexyl), 0.77 (t, 3H, CH$_3$hexyl, J=6.8 Hz). EIMS: 1548 (MH$^+$).

Compound No. 14:

Compound 13 (100.0 mg, 0.064 mmol) was stirred with 80% TFA/DCM (5.0 ml) at RT for 3 hr. Resultant mixture was concentrated and dried under high vacuum to remove trace of TFA. To this crude were added, amino-benzyl-DTPA-penta-tert-butyl ester (503.5 mg, 0.64 mmol), EDCI (123.9 mg, 0.64 mmol) and DMAP (78.8 mg, 0.64 mmol). Dry N, N-dimethylformamide (15 ml) was added to it and reaction mixture was stirred at RT for 16 hr under $N_2$ atm. Reaction mixture was concentrated under vacuum, added dichloromethane (100 ml), washed with brine solution, organic layer separated, dried over sodium sulfate and concentrated. Crude mixture was chromatographed over alumina G (III) using 1-3% Methanol/Dichloromethane mixture as eluent to give product 14. Yield: 250.0 mg (70.0%). UV-vis ($\lambda$max cm$^{-1}$, Dichloromethane): 318, 413, 507, 539, 606 & 660. Elemental analysis: Calculated for $C_{309}H_{491}N_{31}O_{71}$: C, 64.25; H, 8.57; N, 7.52; O, 19.67. found: C, 64.30; H, 8.59; N, 7.56.

Compound No. 15:

Compound 14 (225.0 mg, 0.038 mmol) was stirred with 70% TFA/DCM (5.0 ml) at RT for 3 hr. Resultant mixture was concentrated and dried under high vacuum to remove trace of TFA. The crude thus obtained was dissolved in pyridine (10 ml) and put under stirring, to this stirring solution GdCl$_3$.6H$_2$O (173.7 mg, 0.46 mmol) in 1 ml of water was added slowly and resultant mixture was stirred for 16 hr. Reaction mixture was concentrated to dryness under high vacuum. Residue was washed with water (10 ml×3), acetone (10 ml×3) and finally dried under high vacuum using P$_2$O$_5$ as drying agent. Yield: 170.0 mg (86.7%). UV-vis ($\lambda$max cm$^{-1}$, MeOH): 320, 411, 507, 539, 606 & 660. Elemental analysis: Calculated for $C_{189}H_{251}$, Gd$_6$N$_{31}$O$_{71}$: C, 45.07; H, 5.02; Gd, 18.73; N, 8.62; O, 22.55. found: C, 45.15; H, 5.10; N, 8.58.

Compound No. 16:

Acid 4 (150.0 mg, 0.214 mmol), Di-tert-butyl iminodiacetate (105.0 mg, 0.429 mmol), EDCI (82.3 mg, 0.429 mmol) and DMAP (52.0 mg, 0.429 mmol) were taken in a dry RBF (100 ml). Dry dichloromethane (30 ml) was added to it and reaction mixture was stirred at RT for 16 hr under $N_2$ atm. Reaction mixture was diluted with dichloromethane (100 ml), washed with brine solution, organic layer separated, dried over sodium sulfate and concentrated. Crude mixture was chromatographed over silica gel using 1-1.5% Methanol/Dichloromethane mixture as eluent to give product 16. Yield: 165.0 mg (82.9%). UV-vis ($\lambda$max cm$^{-1}$, dichloromethane): 318, 411, 506, 536, 605 and 661. $^1$HNMR (400 MHz, CDCl$_3$): $\delta$ 9.75 (splitted s, 1H, H-5), 9.52 (splitted s, 1H, H-10), 8.53 (s, 1H, H-20), 6.01 (m, 1H, CH$_3$CHOTEG), 5.31 (d, 1H, CH-15$^1$, J=20.0 Hz), 5.13 (d, 1H, CH-15$^1$, J=20.0 Hz), 4.50 (q, 1H, H-17, J=7.2 Hz), 4.36 (m, 1H, H-18), 4.02 9m, 2H, CH$_2$chain), 3.85 (m, 2H, CH$_2$—O-TEG), 3.79 (m, 2H, CH$_2$—O-TEG), 3.73 (m, 4H, 3CH$_2$—O-TEG), 3.68 (s, 3H, 7-CH$_3$), 3.66 (m, 2H, 8-CH$_2$CH$_3$), 3.55 (m, 2H, CH$_2$—O-TEG), 3.39 (s, 3H, 2-CH$_3$), 3.27 (s, 6H, 12-CH$_3$ & OCH$_3$-TEG), 2.75 (m, 1H, CH-17$^2$), 2.44 (m, 1H, CH-17$^2$), 2.41 (m, 1H, CH-17$^1$), 2.16 (m, 1H, CH-17$^1$), 2.14 (d, 3H, CH$_3$CHOTEG, J=6.4 Hz), 1.81 (d, 3H, 18-CH$_3$, J=7.6 Hz), 1.71 (t, 3H, 8-CH$_2$CH$_3$, J=7.6 Hz), 1.44 (splitted s, 9H, CO$_2^t$Bu), 1.06 (splitted s, 9H, CO$_2^t$Bu), 0.39 (brs, 1H, NH), −1.80 (brs, 1H, NH). EIMS: 927 (MH$^+$).

Compound No. 17:

Compound 16 (140.0 mg, 0.151 mmol) was stirred with 70% TFA/DCM (5.0 ml) at RT for 3 hr. Resultant mixture was concentrated and dried under high vacuum to remove trace of TFA. To this crude were added, amine A (188.2 mg, 0.453 mmol), EDCI (115.9 mg, 0.604 mmol) and DMAP (73.7 mg, 0.604 mmol). Dry dichloromethane (30 ml) was added to it and reaction mixture was stirred at RT for 16 hr under $N_2$ atm. Reaction mixture was diluted with dichloromethane (100 ml), washed with brine solution, organic layer separated, dried over sodium sulfate and concentrated. Crude mixture was chromatographed over silica gel using 3-7% Methanol/Dichloromethane mixture as eluent to give product 17. Yield: 210.0 mg (86.4%). UV-vis ($\lambda$max cm$^{-1}$, dichloromethane): 318, 411, 506, 536, 604 & 661. $^1$HNMR (400 MHz, CDCl$_3$): $\delta$ 9.76 (splitted s, 1H, H-5), 9.53 (s, 1H, H-10), 8.63 (s, 1H, H-20), 8.31 (splitted s, 1H, CONH), 6.56 (splitted s, 1H, CONH), 6.00 (m, 1H, CH$_3$CHOTEG), 5.35 (d, 1H, CH-15$^1$, J=20.0 Hz), 5.16 (d, 1H, CH-15$^1$, J=20.0 Hz), 4.53 (q, 1H, H-17, J=7.6 Hz), 4.36 (d, 1H, H-18, J=10.4 Hz), 3.85-3.80 (m, 4H, 2CH$_2$—O-TEG), 3.74-3.71 (m, 6H, 2CH$_2$chain, CH$_2$—O-TEG), 3.67 (s, 3H, 7-CH$_3$), 3.66 (m, 4H, 8-CH$_2$CH$_3$, CH$_2$—O-TEG), 3.53 (m, 2H, CH$_2$—O-TEG), 3.42-3.39 (m, 5H, CH$_2$—O-TEG, 2-CH$_3$), 3.27-3.26 (m, 6H, 12-CH$_3$, OCH$_3$TEG), 2.75 (m, 1H, CH-17$^2$), 2.67 (m, 1H, CH-17$^2$), 2.52 (m, 1H, CH-17$^1$), 2.24-2.22 (m, 13H, 6CH$_2$-chain, CH-17$^1$), 2.14 (d, 3H, CH$_3$CHOTEG, J=6.8 Hz), 2.09-2.04 (m, 6H, 3CH$_2$-chain), 1.96 (m, 6H, 3CH$_2$-chain), 1.81 (d, 3H, 18-CH$_3$, J=7.2 Hz), 1.71 (t, 3H, 8-CH$_2$CH$_3$, J=8.0 Hz), 1.41 (s, 27H, 3CO$_2^t$Bu), 1.33 (s, 27H, 3CO$_2^t$Bu), 0.39 (brs, 1H, NH), −1.79 (brs, 1H, NH). EIMS: 1610 (MH$^+$).

Compound No. 18:

Compound 17 (100.0 mg, 0.06 mmol) was stirred with 80% TFA/DCM (5.0 ml) at RT for 3 hr. Resultant mixture was concentrated and dried under high vacuum to remove trace of TFA. To this crude were added, amino-benzyl-DTPA-penta-tert-butyl ester (471.0 mg, 0.60 mmol), EDCI (115.9 mg, 0.60 mmol) and DMAP (73.8 mg, 0.60 mmol). Dry N, N-dimethylformamide (15 ml) was added to it and reaction mixture was stirred at RT for 16 hr under $N_2$ atm. Reaction mixture was concentrated under vacuum, added dichloromethane (100 ml), washed with brine solution, organic layer separated, dried over sodium sulfate and concentrated. Crude mixture was chromatographed over alumina G (III) using 1-3% Methanol/Dichloromethane mixture as eluent to give product 18. Yield: 250.0 mg (69.0%). UV-vis (λmax cm$^{-1}$, Dichloromethane): 319, 412, 508, 538, 606 & 661. Elemental analysis: Calculated for $C_{309}H_{491}N_{31}O_{74}$: C, 63.72; H, 8.50; N, 7.46; O, 20.33. found: C, 63.67; H, 8.57; N, 7.46.

Compound No. 19:

Compound 18 (215.0 mg, 0.0369 mmol) was stirred with 80% TFA/DCM (5.0 ml) at RT for 3 hr. Resultant mixture was concentrated and dried under high vacuum to remove trace of TFA. The crude thus obtained was dissolved in pyridine (10 ml) and put under stirring, to this stirring solution $GdCl_3.6H_2O$ (164.6 mg, 0.44 mmol) in 1 ml of water was added slowly and resultant mixture was stirred for 16 hr. Reaction mixture was concentrated to dryness under high vacuum. Residue was washed with water (10 ml×3), acetone (10 ml×3) and finally dried under high vacuum using $P_2O_5$ as drying agent. Yield: 160.0 mg (85.0%). UV-vis (λmax cm$^{-1}$, MeOH): 320, 410, 507, 539, 606 & 661. Elemental analysis: Calculated for $C_{190}H_{253}Gd_6N_{31}O_{74}$: C, 44.76; H, 5.00; Gd, 18.50; N, 8.52; O, 23.22. found: C, 44.80; H, 5.07; N, 8.51.

Scheme-1

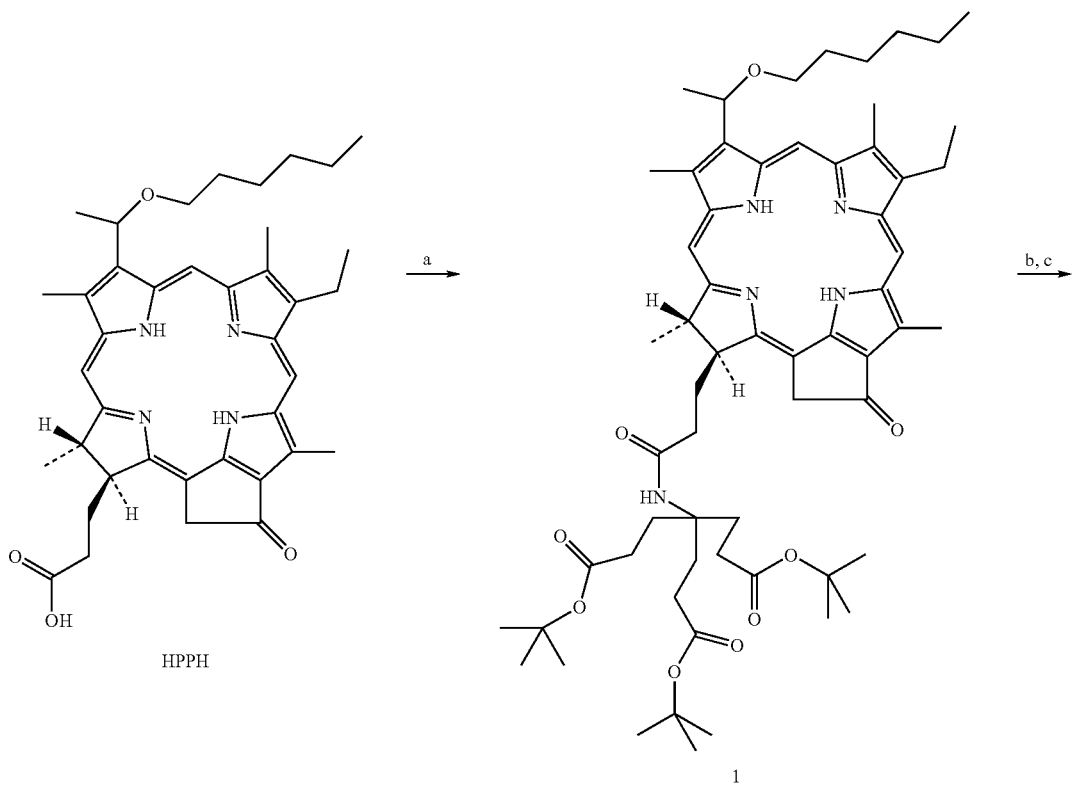

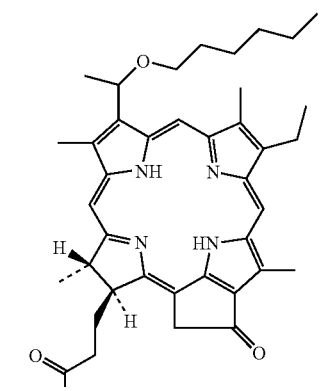

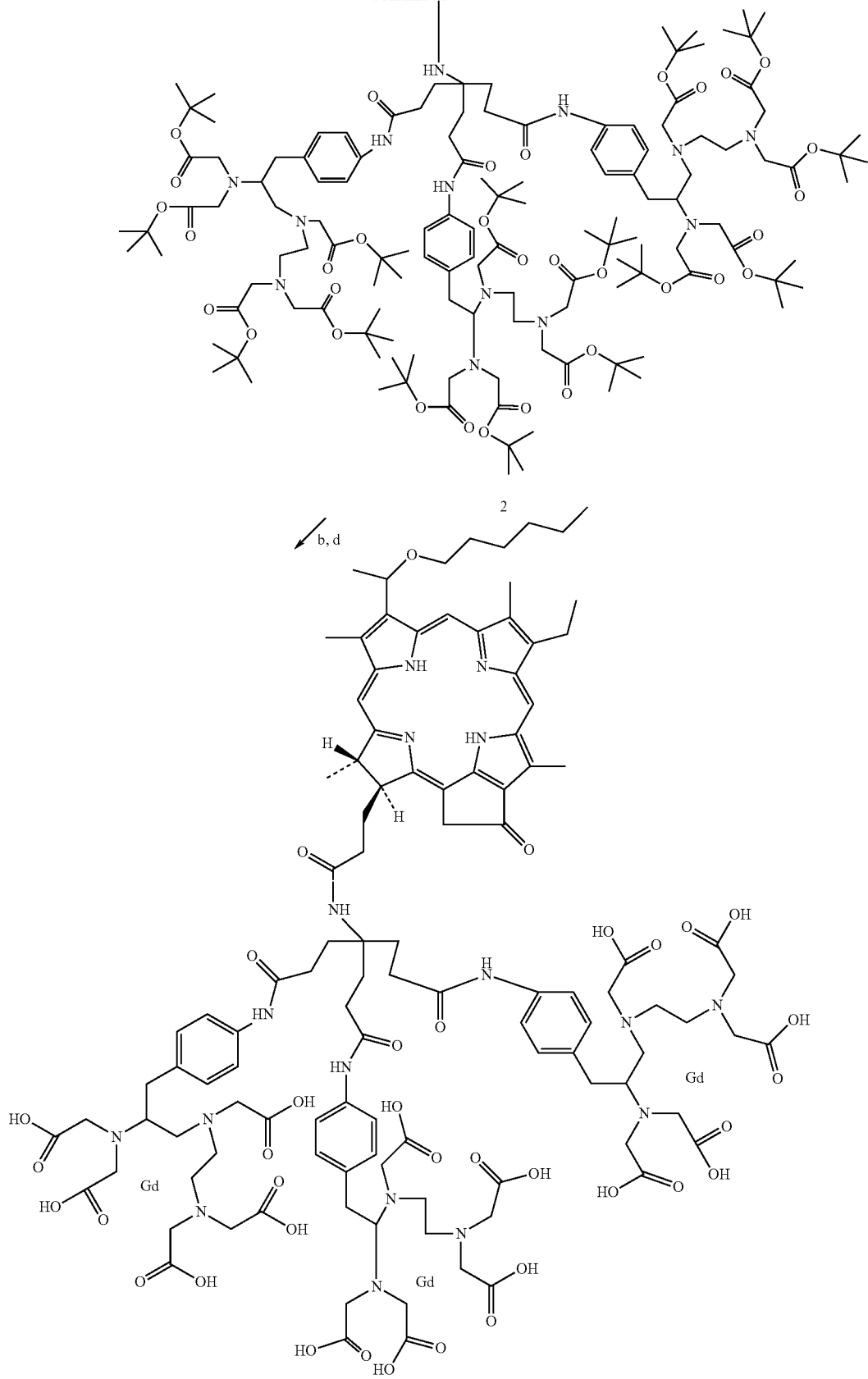

-continued
Reagents and conditions:
a, A, EDCl, DMAP, Dry DCM, RT, 16 hr
b, 70% TFA/DCM, RT, 3 hr
c, amino-benzyl-DTPA-penta-tert-butyl ester,
   EDCl, DMAP, Dry DCM, RT, 16 hr
d, Pyridine-H₂O, GdCl₃, 6H₂O, 16 hr, RT
A =
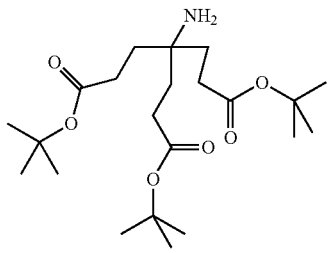
Scheme-2
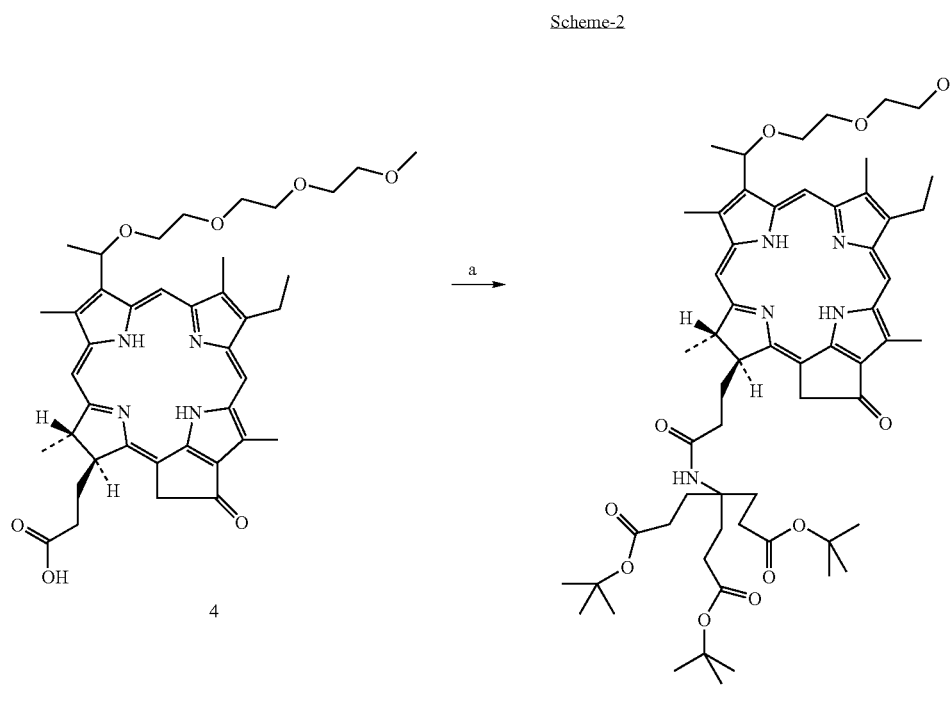
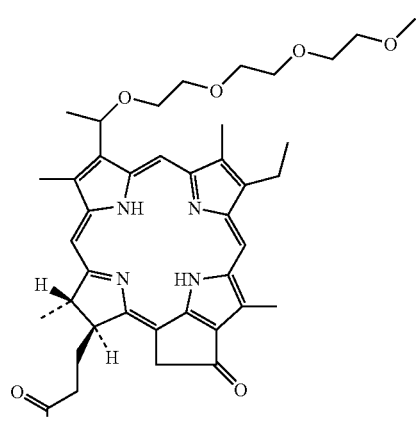

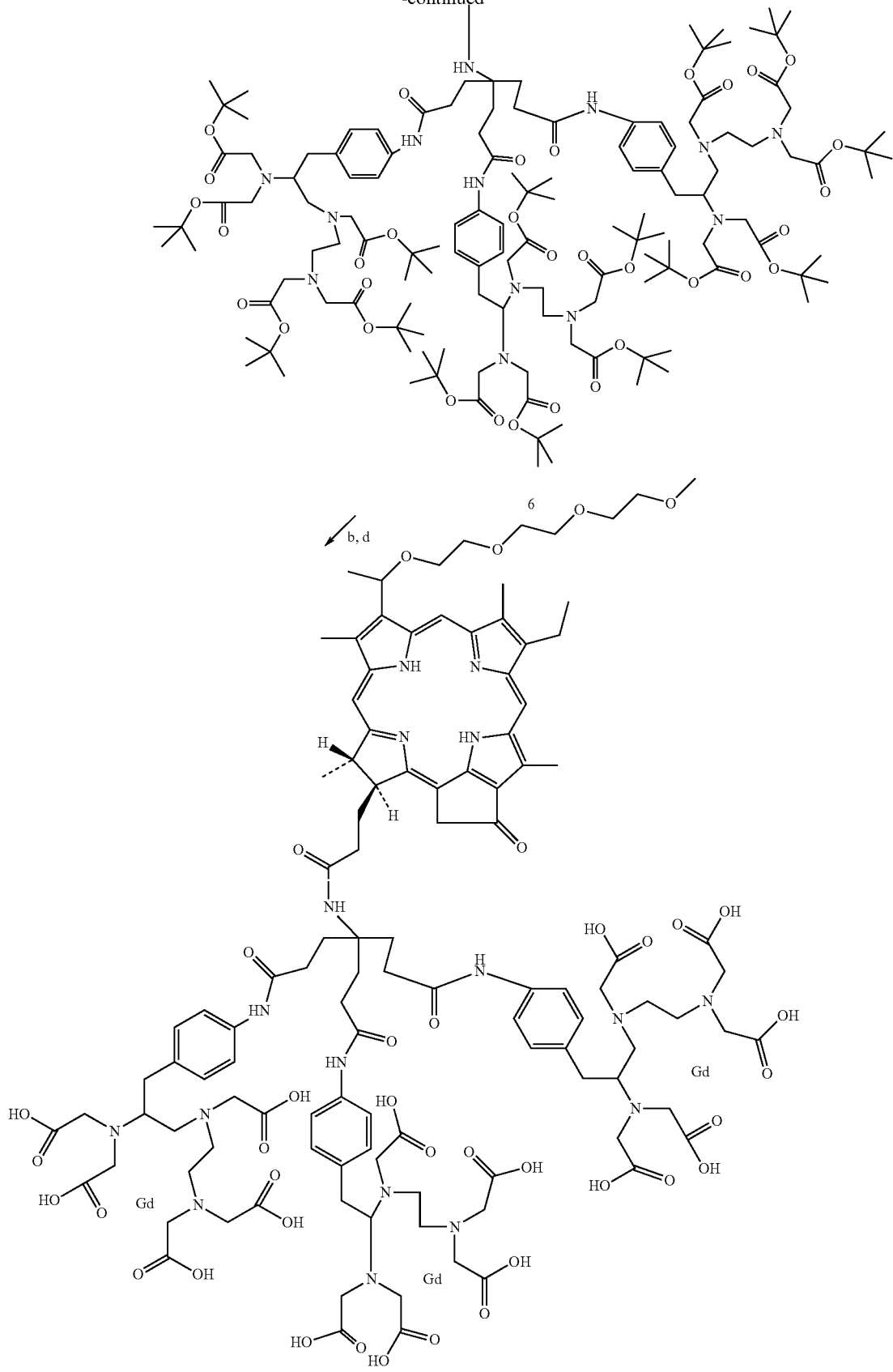

Reagents and conditions:
a, A, EDCl, DMAP, Dry DCM, RT, 16 hr
b, 70% TFA/DCM, RT, 3 hr
c, amino-benzyl-DTPA-penta-tert-butyl ester,
   EDCl, DMAP, Dry DCM, RT, 16 hr
d, Pyridine-H₂O, GdCl₃, 6H₂O, 16 hr, RT
Scheme-3
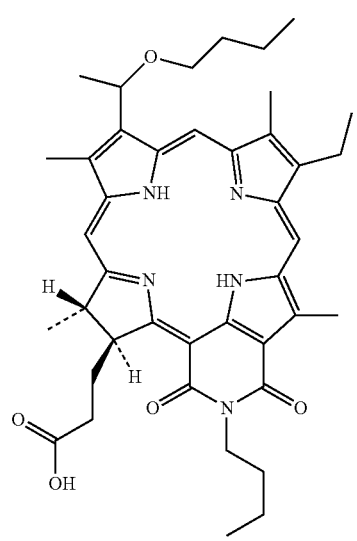
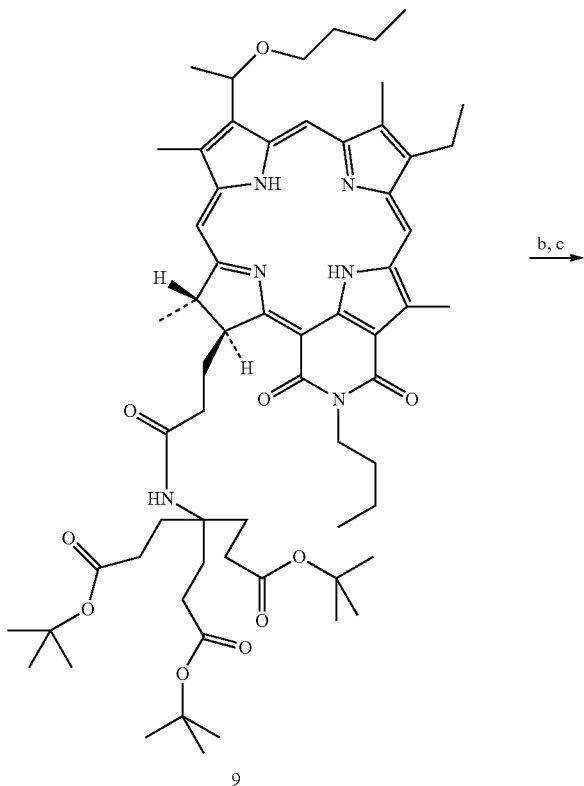
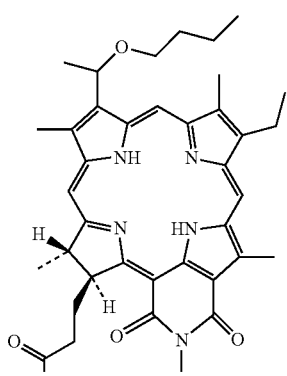

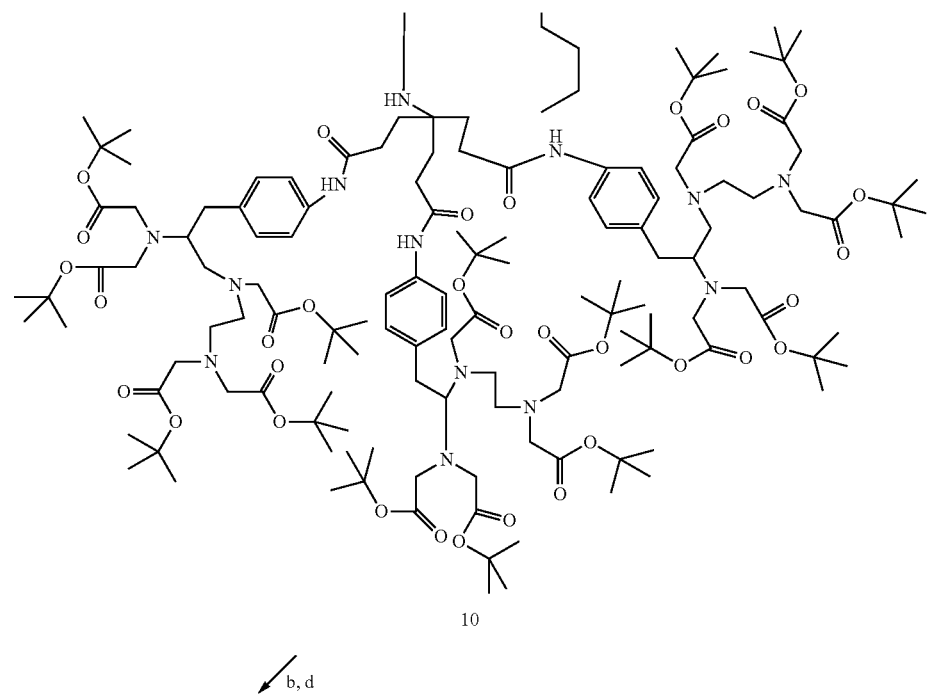
10
↙ b, d
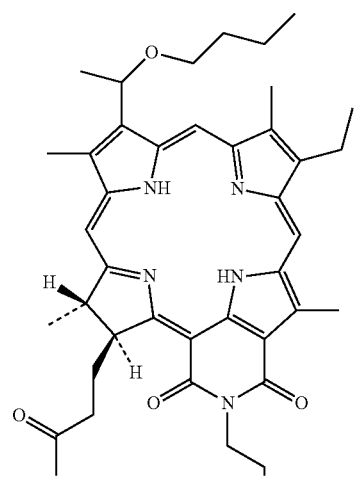

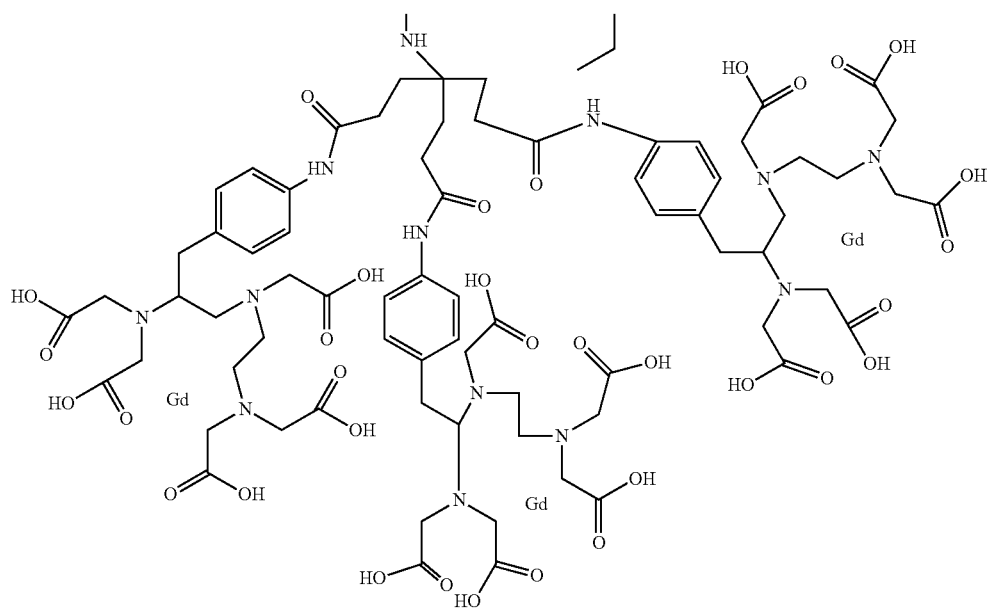
11
Reagents and conditions:
a, A, EDCl, DMAP, Dry DCM, RT, 16 hr
b, 70% TFA/DCM, RT, 3 hr
c, amino-benzyl-DTPA-penta-tert-butyl ester, EDCl, DMAP, Dry DCM, RT, 16 hr
d, Pyridine-H$_2$O, GdCl$_3$, 6H$_2$O, 16 hr, RT
Scheme-4
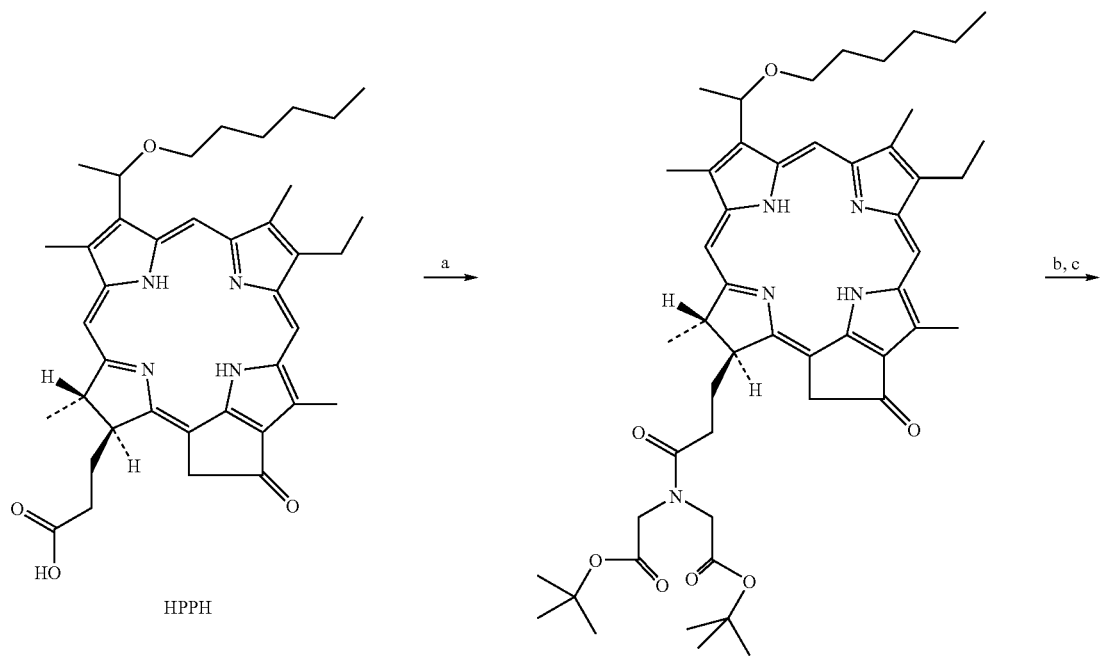
HPPH
12

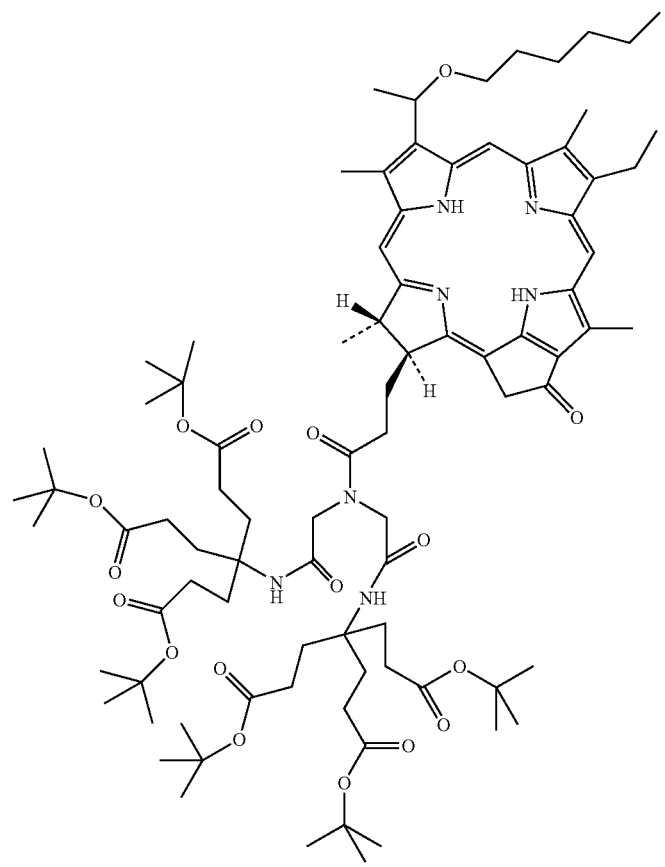
13
b, d, ↓
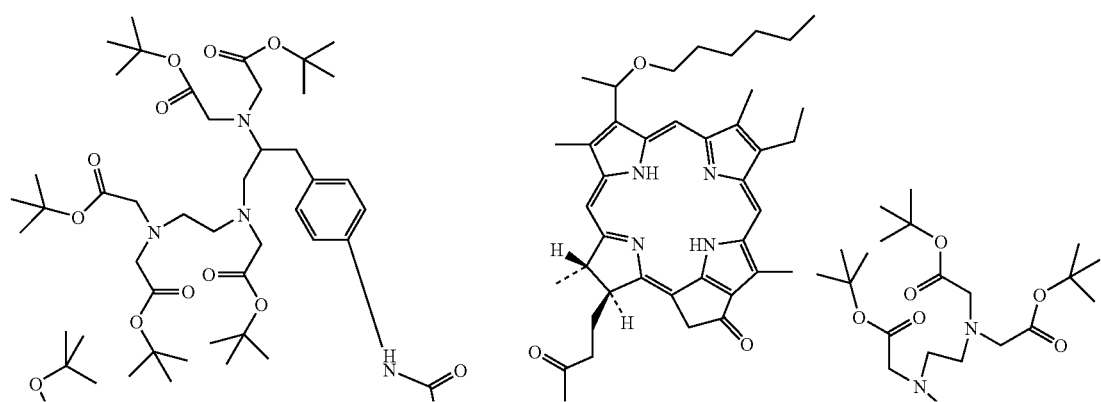

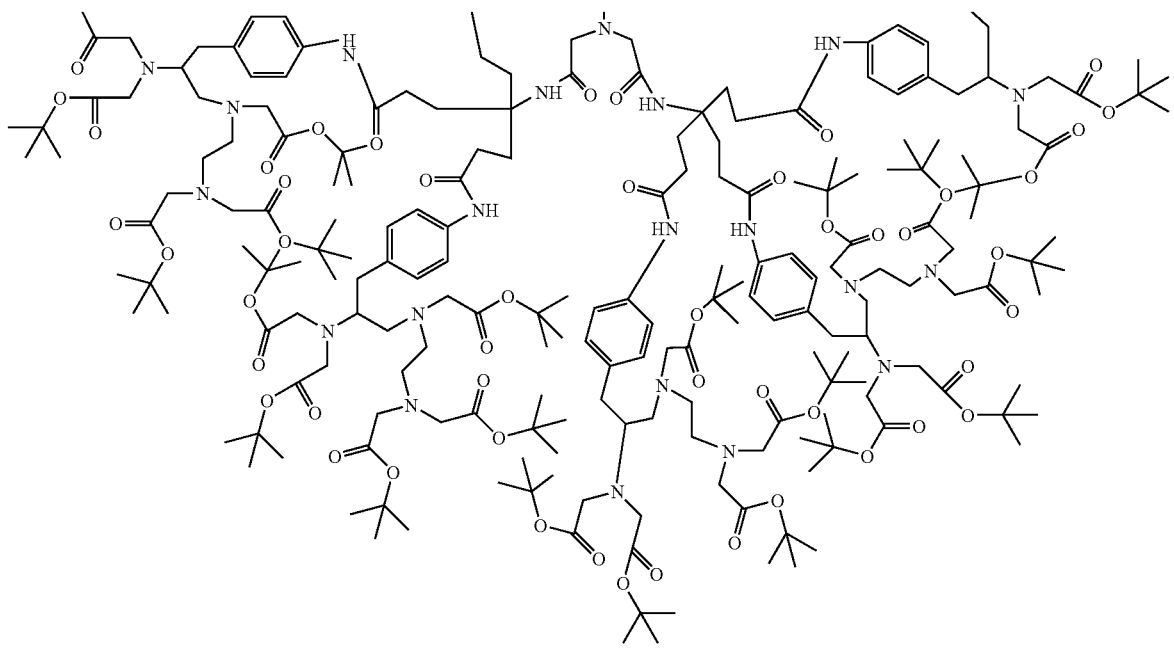
14
↓ b, e
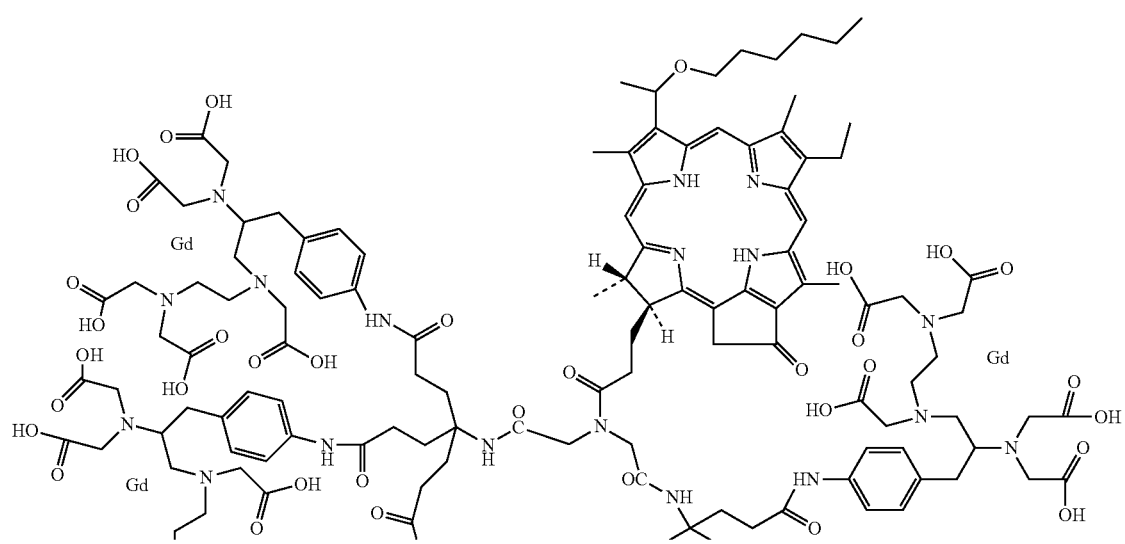

-continued
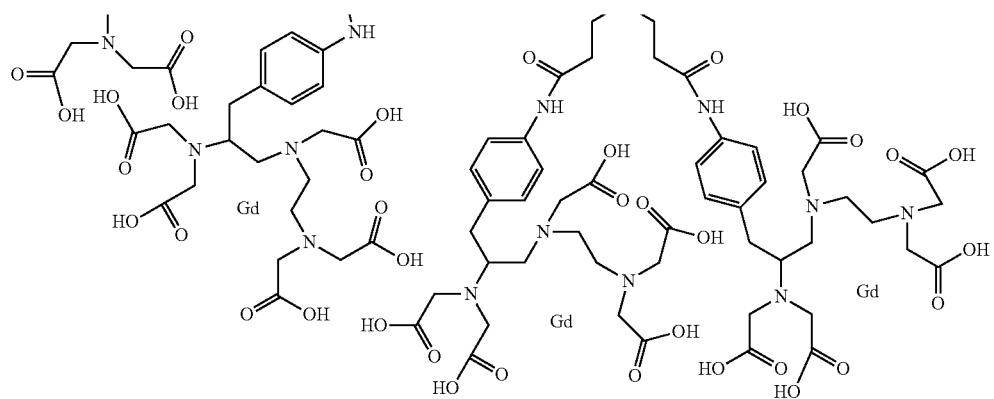
15
Reagents and conditions:
a, Di-tert-butyl iminodiacetate, EDCl, DMAP, Dry DCM, RT, 16 hr
b, 70% TFA/DCM, RT, 3 hr
c, A, EDCl, DMAP, Dry DCM, RT, 16 hr
d, amino-benzyl-DTPA-penta-tert-butyl ester,
    EDCl, DMAP, Dry DCM, RT, 16 hr
e, Pyridine-H$_2$O, GdCl$_3$, 6H$_2$O, 16 hr, RT Scheme-5
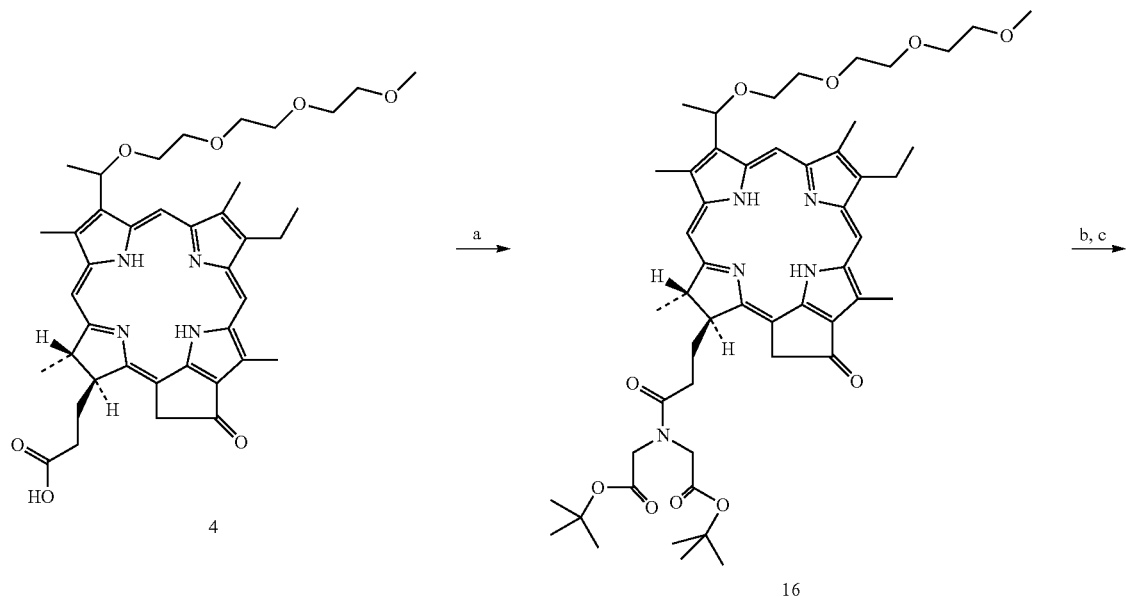
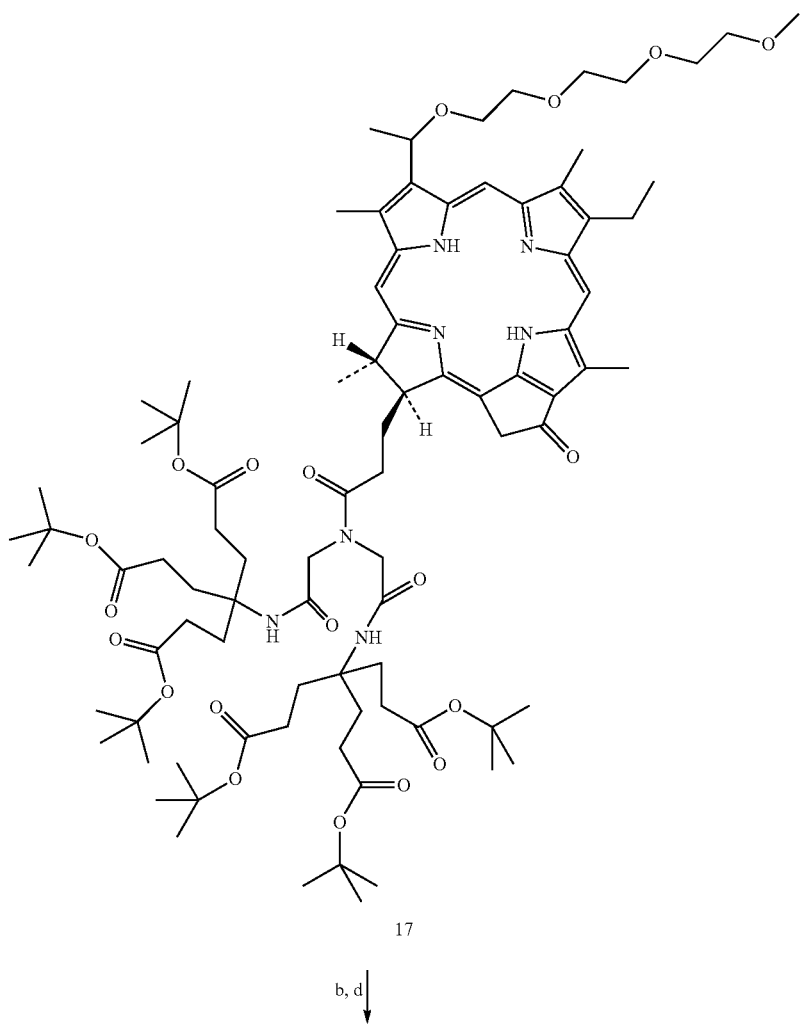

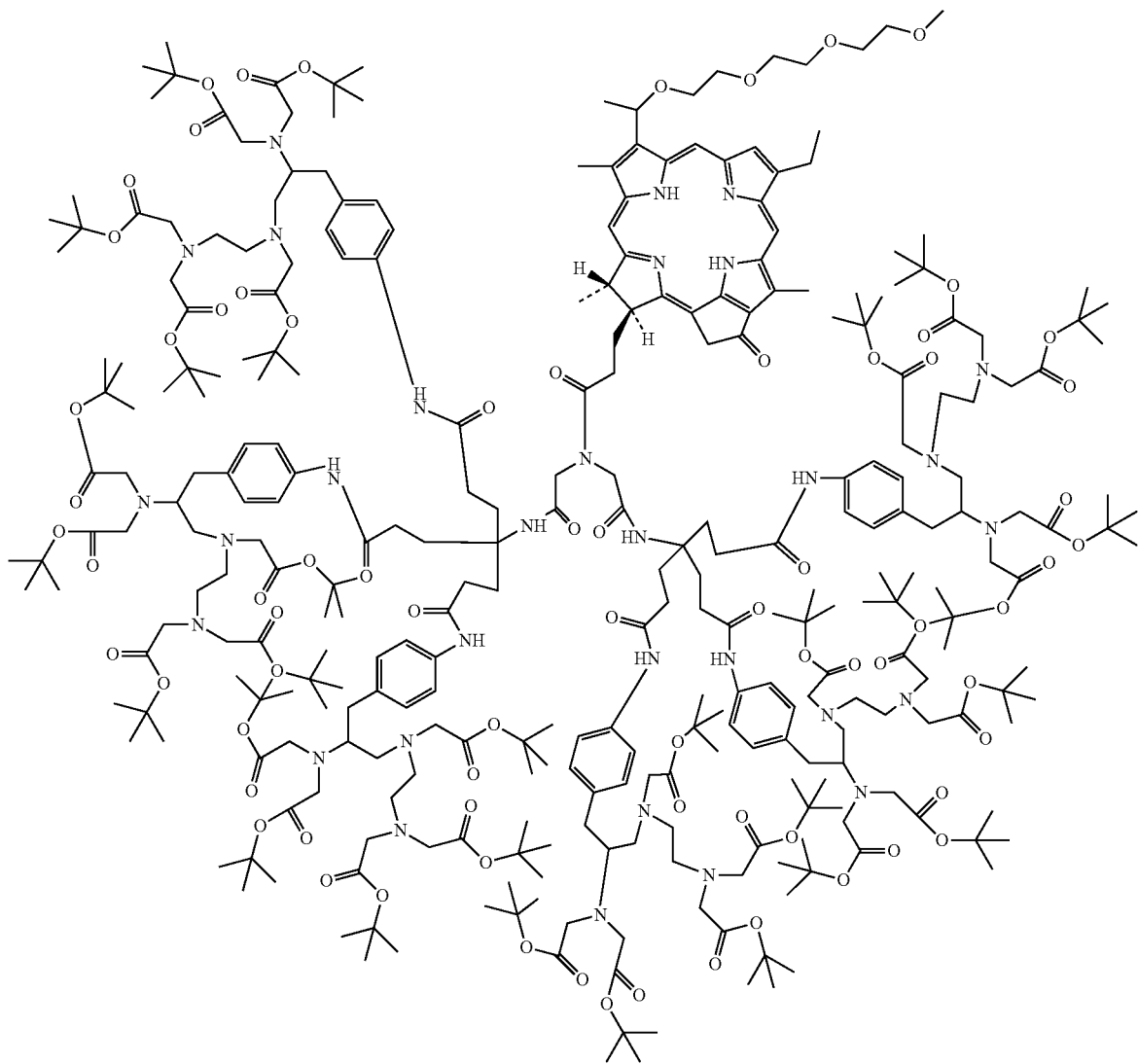
18
↓ b, e

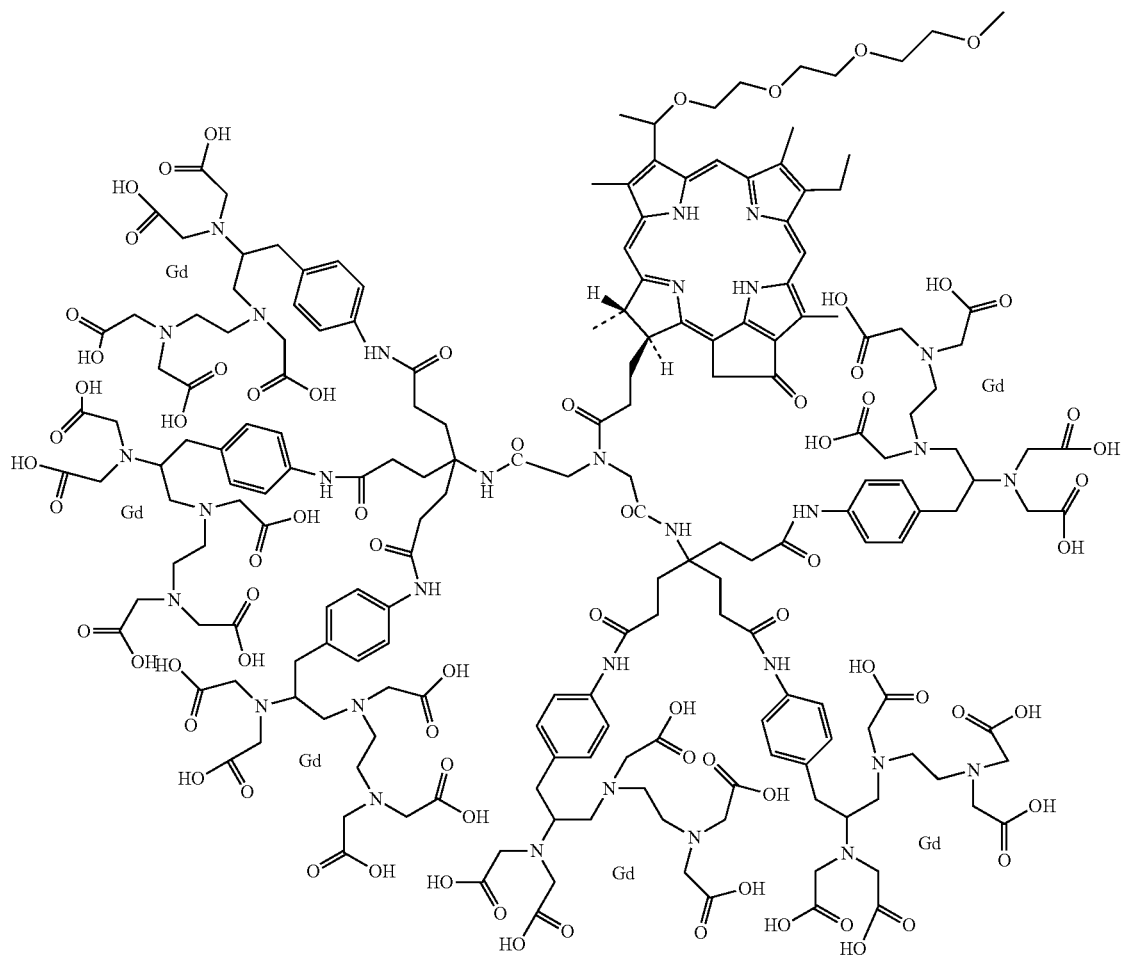
19
Reagents and conditions:
a, Di-tert-butyl iminodiacetate, EDCl, DMAP, Dry DCM, RT, 16 hr
b, 70% TFA/DCM, RT, 3 hr
c, A, EDCl, DMAP, Dry DCM, RT, 16 hr
d, amino-benzyl-DTPA-penta-tert-butyl ester,
   EDCl, DMAP, Dry DCM, RT, 16 hr
e, Pyridine-H$_2$O, GdCl$_3$, 6H$_2$O, 16 hr, RT

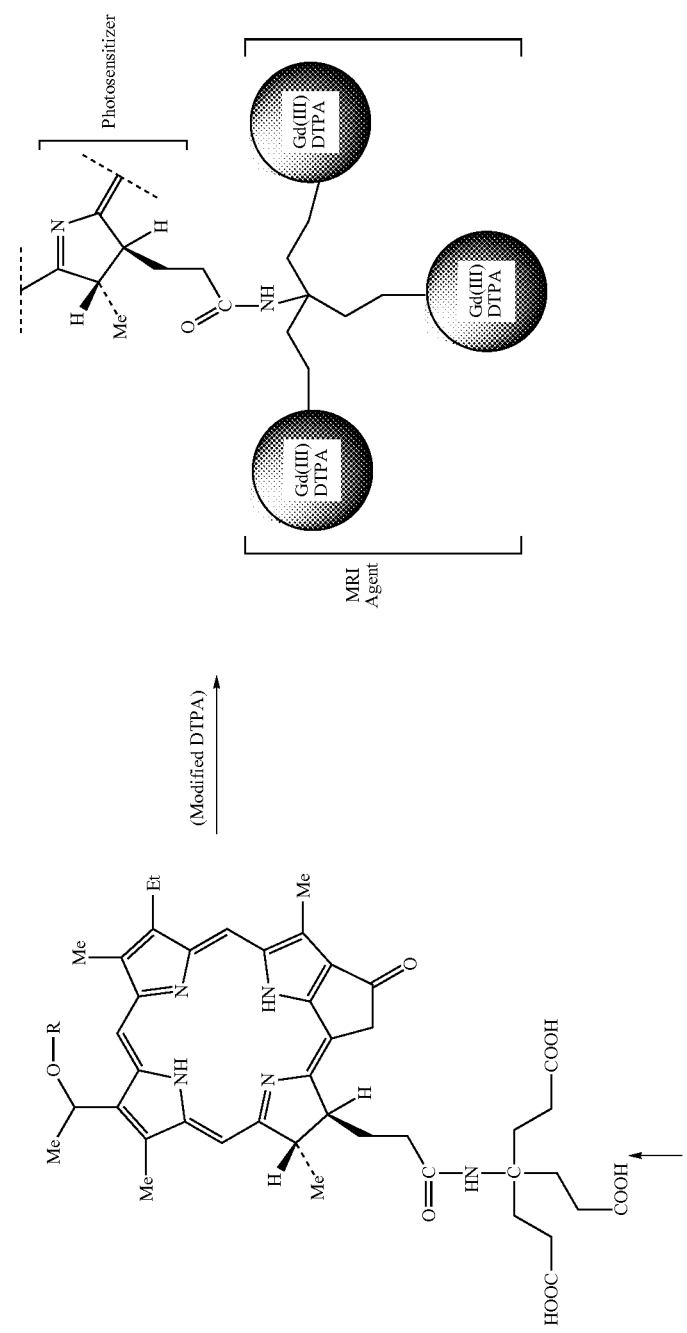

-continued
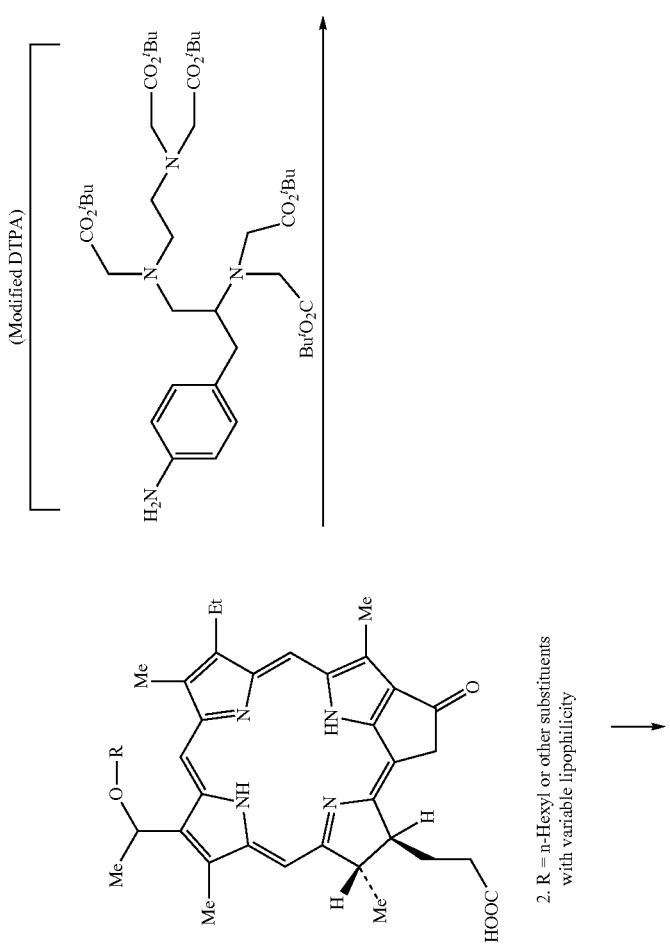

-continued
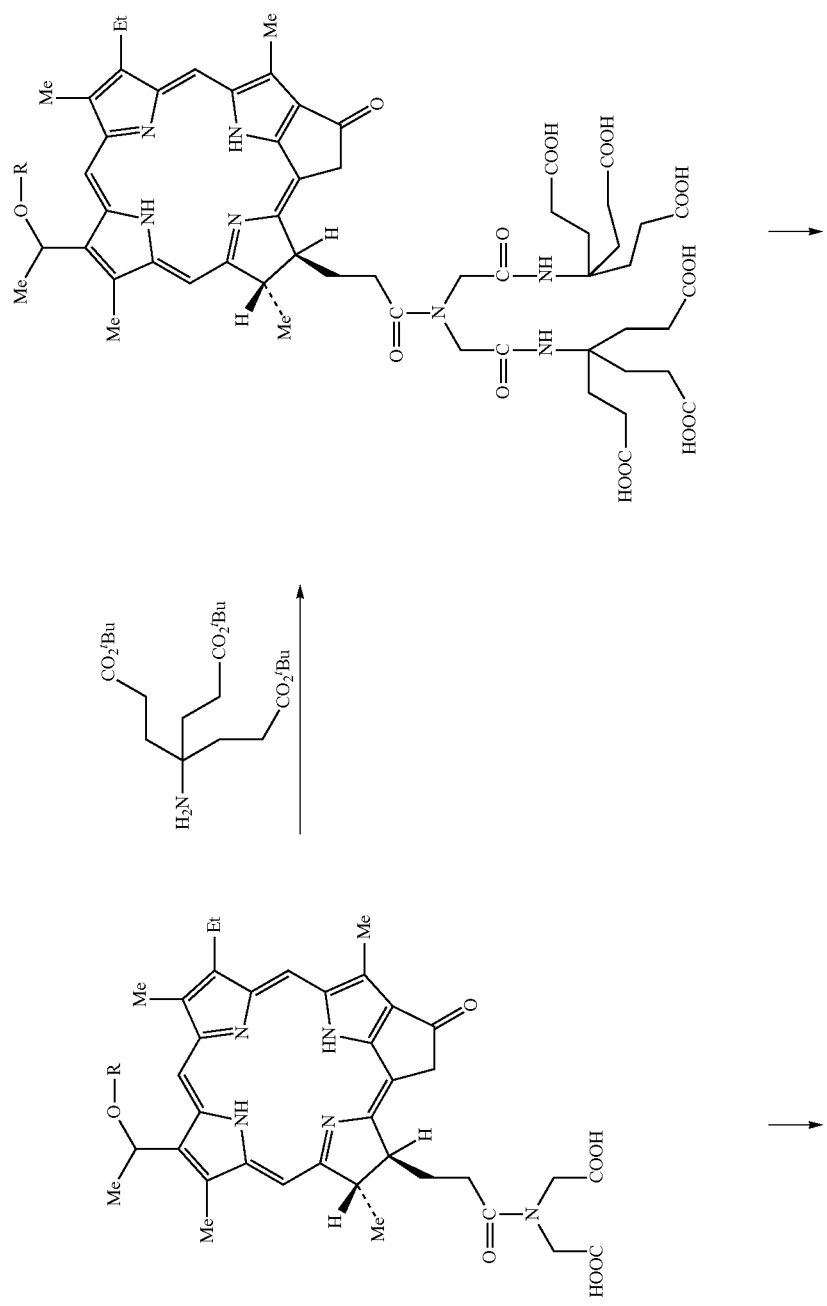

-continued
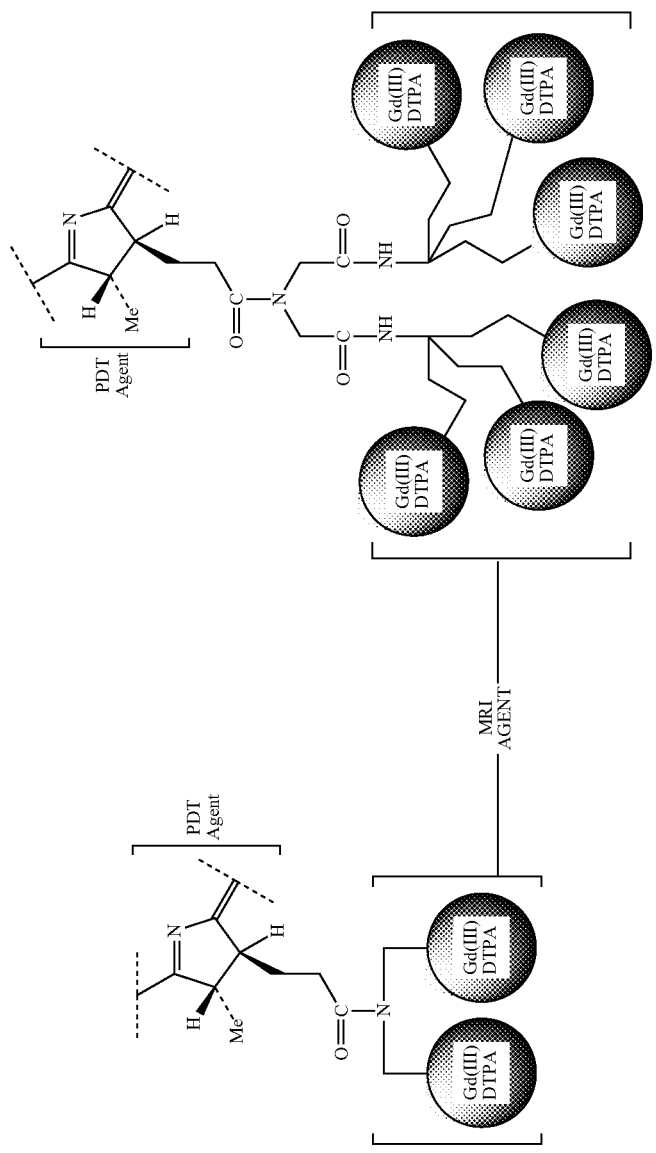

Relaxivity measurements for examples of the compounds as presented herein were acquired on a General Electric 4.7T/33 cm horizontal bore magnet (GE NMR instruments, Fremont, Calif.) incorporating AVANCE digital electronics (Bruker BioSpec platform with ParaVision version 3.0.2 acquisition software, Bruker Medical, Billerica, Mass.).

T1 relaxation rates (R1) were acquired for a range of contrast agent concentrations (0.02 mM to 0.10 mM) with a saturation recovery spin-echo (SE) sequence with a fixed TE=10 ms and TR times ranging from 75 to 8000 ms. Additional MR acquisition parameters are as follows: (FOV) 32×32 mm, slice thickness=1 mm, slices=3, interslice gap=2 mm, matrix=192×192, NEX=1. Signal intensities at each repetition time was obtained by taking the mean intensity within regions of interest (ROI's) using Analyze 5.0 (Biomedical Imaging Resource, Mayo Foundation, Rochester, Minn.), and $R_1$ and $S_{MAX}$ were determined by nonlinear fitting of the equation: $S_{(TR)}=S_{MAX}(1-e^{-(R1*TR)})$+Background Noise using Matlab's Curve Fitting Toolbox (Matlab 7.0, MathWorks Inc., Natick, Mass.). The $T_1$ relaxivity was then determined by obtaining the slope of concentration vs. R1 via linear regression fitting. Similarly, $T_2$ relaxation rates ($R_2$) were acquired with multi-echo, CPMG SE sequence with a fixed TR of 2500 ms and TE times ranging from 15 to 300 ms, and the number of averages=2. $R_2$ and $S_{MAX}$ were determined as described above using the equation: $S_{(TE)}=S_{MAX}(e^{-(R2*TE)})$+Background Noise. As before, the T2 relaxivity was then determined by obtaining the slope of concentration vs. R2 via linear regression fitting.

Results are shown in Table 1

Results:

TABLE 1

T1/T2 relaxivity of photosensitizer-Gd(III)DTPA conjugates

| Compound | | T1 Relaxivity (mM·s)$^{-1}$ | T2 Relaxivity (mM·s)$^{-1}$ |
|---|---|---|---|
| 593 (HPPH-3Gd) | 3 | 23.9 | 62.81 |
| 601 (HPPH-6Gd) | 15 | 24.72 | 66.54 |
| 604 (PP-Dibutyl-3Gd) | 11 | 20.11 | 84.58 |
| 611 (Pyro-OTEG-3Gd) | 7 | 13.58 | 40.11 |
| 612 (Pyro-OTEG-6Gd) | 19 | 25.09 | 69.19 |

On a T1-weighted scan and at low intratumoral concentrations of the agents (<0.1 mM), shortened T1 times will dominate the effect on signal intensity. All five of the compounds exhibit much higher T1 relaxivity values (Table 1) than conventional MR contrast-enhancing agents, which have T1 relaxivities~3 to 4 (mM·s)$^{-1}$. The increased relaxivities of our compounds allow for reduced doses with similar enhancement when compared to conventional compounds. These compounds were tested in vivo (next section) a injection doses of 10 μmoles/kg vs. 100 μmoles/kg prescribed for conventional MR contrast agents.

Examples of compounds of the invention were tested in vivo. Baseline MR images were acquired prior to injection of the compounds to serve as a baseline comparison. Animals were then re-scanned 8 and 24 hours after injection. Two spin-echo imaging protocols were used, all utilizing the same geometry (5-6 axial slices, 1.5 mm slice thickness, 6×6 cm FOV). The first scanning protocol was a moderately T1-weighted scan acquired with a TE/TR of 10/1200 ms. The second protocol was a heavily T1-weighted scan acquired with Chemical Shift Selective (CHESS) fat suppression with a TE/TR of 10/356 ms.

Figure 1B:
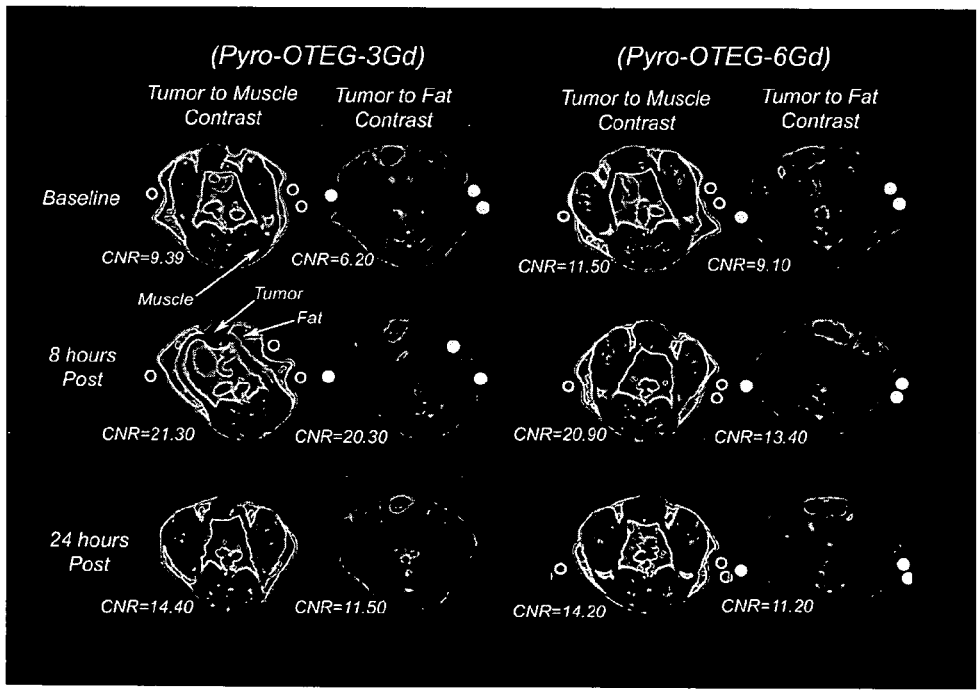
FIG. 1B shows MRI images of tumors as compared to muscle using conjugate 7.

Regions of interest (ROI's) for tumor, muscle, fat, and noise were defined, and the mean intensity and standard deviation for each ROI was sampled. Tumor conspicuity was measured by determining the contrast-to-noise ratios (CNR's), which is defined as the difference in signal between two tissues divided by the standard deviation of the noise. Enhancement of tumor as compared to muscle was determined using the first scanning protocol (TE/TR=10.3/1200 ms). Due to the inherent hyperintensity of fat on T1-weighted MR scans, enhancement of the tumor as compared to fat was determined by analyzing the fat-suppressed images. Results are outlined in Tables 2 & 3, and sample images show in FIGS. 1A and 1B.

TABLE 2

Tumor to fat contrast/noise ratio of the Photosensitizer-Gd(III) conjugates
Tumor to Fat Contrast to Noise Ratio (CNR)

| | CNR | | | | CNR Improvement | | |
|---|---|---|---|---|---|---|---|
| Compound | Baseline | 4 hr | 8 hr | 24 hr | 4 hr | 8 hr | 24 hr |
| 593 (HPPH-3Gd)-3 | 10.42 | xx | 15.88 | 19.34 | xx | 54% | 86% |
| 601 (HPPH-6Gd)-15 | 15.61 | xx | 23.80 | 22.66 | xx | 52% | 45% |
| 604 (PP-Dibutyl-3Gd)-11 | 5.36 | xx | 15.78 | 17.84 | xx | 194% | 233% |
| 611 (Pyro-OTEG-3Gd)-7 | 6.20 | xx | 20.30 | 11.50 | xx | 227% | 85% |
| 612 (Pyro-OTEG-6Gd)-19 | 9.10 | 18.60 | 13.40 | 11.20 | 104% | 47% | 23% |

TABLE 3

Tumor to muscle contrast/noise ratio of the photosensitizer Gd(III) conjugates
Tumor to Muscle Contrast to Noise Ratio (CNR)

| | CNR | | | | CNR Improvement | | |
|---|---|---|---|---|---|---|---|
| Compound | Baseline | 4 hr | 8 hr | 24 hr | 4 hr | 8 hr | 24 hr |
| 593-3 | 8.69 | xx | 15.31 | 19.17 | xx | 66% | 96% |
| 601-15 | 6.36 | xx | 13.40 | 18.65 | xx | 111% | 193% |
| 604-11 | 9.93 | xx | 10.40 | 20.48 | xx | 5% | 106% |
| 611-7 | 9.39 | 20.00 | 21.30 | 14.40 | 113% | 127% | 53% |
| 612-19 | 11.50 | 16.30 | 20.90 | 14.20 | 42% | 82% | 23% |

Figure 2:
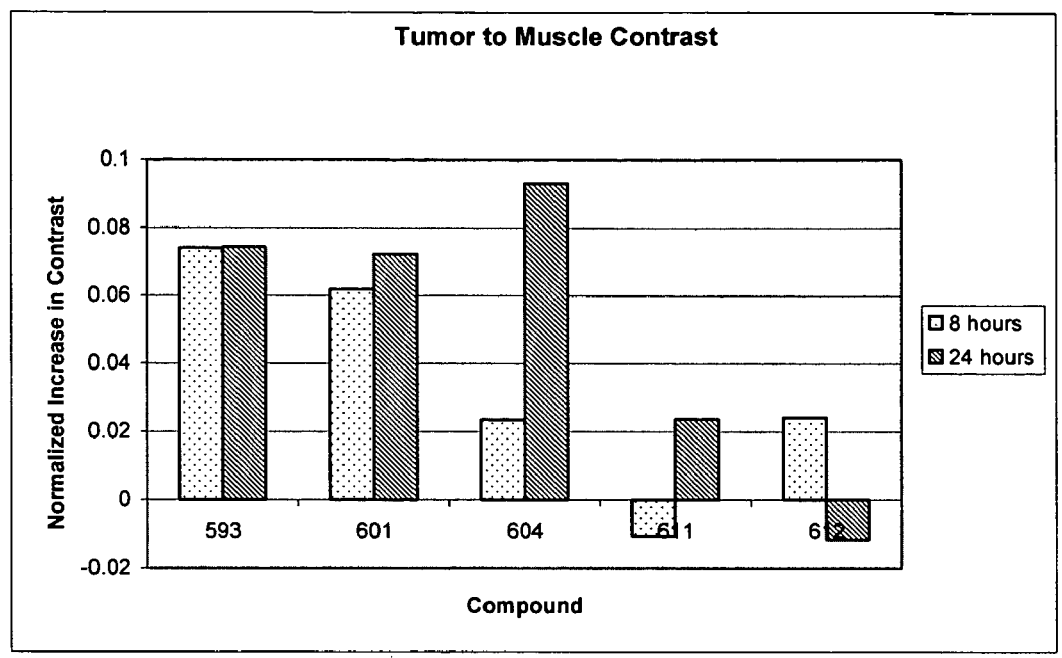
FIG. 2 is a bar graph showing tumor to muscle contrast of the conjugates.
Figure 3:
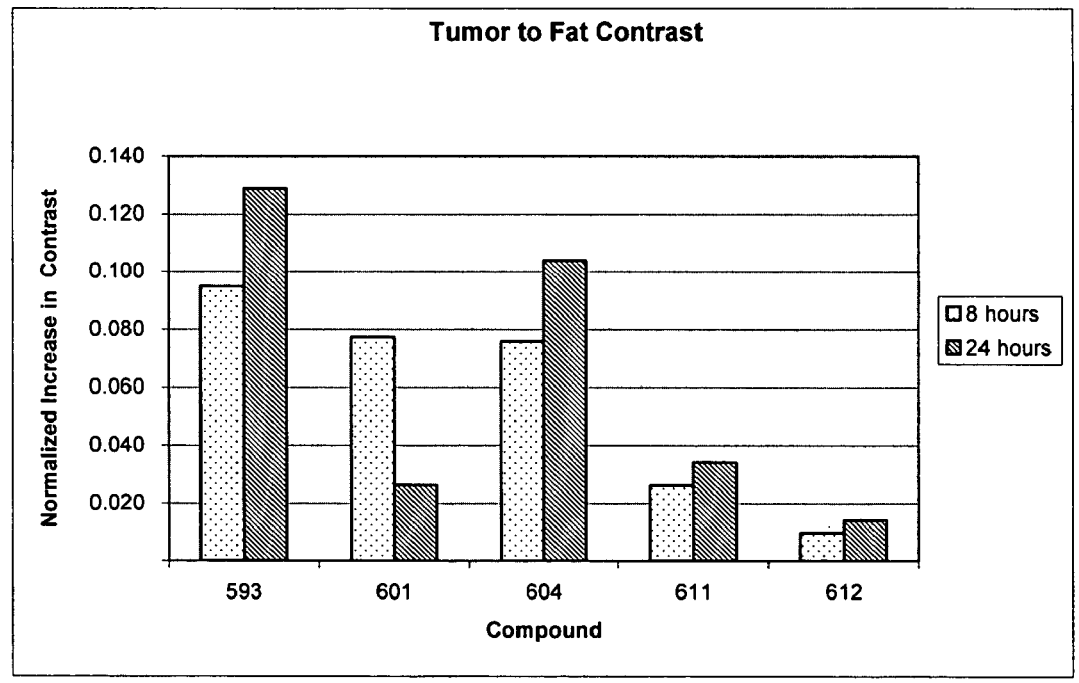
FIG. 3 is a bar graph showing tumor to fat contrast of the conjugates.

Additionally, tumor avidity of each formulation was investigated by comparing the increase in contrast, i.e. difference in normalized signal, between tumor and normal tissues. The HPPH-Gd compounds demonstrated a much higher contrast between tumor and normal tissue than the Pyro-OTEG compounds shown in FIGS. 2 & 3. The PP-Dibutyl compound showed peak contrast at 24 hours. In the Figures, compounds coded as 593=3; 601=15; 604=11, 611=7 and 612=19. FIGS. 2 and 3 show tumor to muscle and tumor to fat contrast of the conjugates.

The relatively low increase in contrast between tumors and normal tissues with the Pyro-OTEG compounds is indicative that the increase in the CNR's is predominately a global increase of signal-to-noise in the images than a preferential accumulation of the compound within the tumor.

HPPH-formulations (593 (3) and 601 (15)) showed a continuation of increasing CNR of tumor to fat and muscle from 8 hours to 24 hours. This is indicative of a longer circulation time of these compounds as compared to the Pyro-OTEG from. Conversely, the Pyro-OTEG formulations (611 (7) & 612 (19)) also showed large increases in CNR at 4 and 8 hours, but then decreased 24 hours later. This is indicative of a much shorter circulation time, which may limit efficacy of PDT treatments if not performed within 8 hours of the administration of the agent. Furthermore, the relative increase in contrast with the Pyro-OTEG compounds [611 (7) & 612 (19)] was much lower than that of the HPPH and PP-Dibutyl compounds (593 (3), 601 (15) & 604 (11)), which is exhibited in FIGS. 2 and 3. The large increases in contrast-to-noise with these compounds is attributed more to a global increase in signal to noise (due to the presence of the agents) than tumor avidity. In "real world" application, an increase in CNR is most effective when the CNR approaches a threshold of detection, which is within the range of CNR=2 to 5 for humans. Due to the bi-functionality of these agents, serving as both PDT agents as well as MR contrast-enhancing agents, the greater tumor avidity of compounds 593 (3), 601 (15), & 604 (11) would be preferred over the Pyro-OTEG compounds so that the effect of the PDT therapy is more specific to the tumor tissue rather than host tissue. However, it is foreseeable that the more rapidly clearing Pyro-OTEG compounds would be seen as beneficial in clinical applications.

What is claimed is:

1. A tetrapyrrollic photosensitizer compound said tetrapyrrollic compound being a chlorin, bacteriochlorin, porphyrin, pyropheophorbide, purpurinimide, or bacteriopurpurinimide having 3 to 6 —CH$_2$CONHphenylCH$_2$CH(N(CH$_2$COOH)$_2$)(CH$_2$N(CH$_2$COOH)(CH$_2$CH$_2$N(CH$_2$COOH)$_2$)) groups or esters thereof or complexes thereof with gadolinium(III).

2. The compound of claim 1 having at least one pendant —CH$_2$CH$_2$CONHC(CH$_2$CH$_2$CONHphenylCH$_2$CH(N(CH$_2$COOH)$_2$(CH$_2$N(CH$_2$COOH)—(CH$_2$CH$_2$N(CH$_2$COOH)$_2$)))$_3$ group or esters thereof or complexes thereof with gadolinium(III).

3. A compound of the formula:

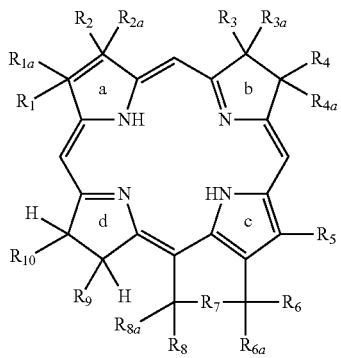

wherein:

R$_1$ is independently substituted or unsubstituted alkyl, substituted or unsubstituted alkenyl, —C(O)R$_a$ or —COOR$_a$ or —CH(CH$_3$)(OR) or —CH(CH$_3$)(O(CH$_2$)$_n$XR) where R$_a$ is hydrogen, substituted or unsubstituted alkyl, substituted or unsubstituted alkenyl, substituted or unsubstituted alkynyl, or substituted or unsubstituted cycloalkyl;

R$_2$ is independently substituted or unsubstituted alkyl, substituted or unsubstituted alkenyl, —C(O)R$_a$ or —COOR$_a$ or —CH(CH$_3$)(OR) or —CH(CH$_3$)(O(CH$_2$)$_n$XR) where R$_a$ is hydrogen, substituted or unsubstituted alkyl, substituted or unsubstituted alkenyl, substituted or unsubstituted alkynyl, or substituted or unsubstituted cycloalkyl, CH=CH$_2$, CH(OR$_{20}$)CH$_3$, C(O)Me, C(=NR$_{21}$)CH$_3$ or CH(NHR$_{21}$)CH$_3$;

where X is an aryl or heteroaryl group;

n is an integer of 0 to 6;

R and R' are independently H or lower alkyl of 1 through 8 carbon atoms;

where R$_{20}$ is methyl, butyl, heptyl, docecyl or 3,5-bis(trifluoromethyl)-benzyl; and R$_{21}$ is 3,5,-bis(trifluoromethyl)benzyl;

R$_{1a}$ and R$_{2a}$ are each independently hydrogen or substituted or unsubstituted alkyl, or together form a covalent bond;

R$_3$ and R$_4$ are each independently hydrogen or substituted or unsubstituted alkyl;

R$_{3a}$ and R$_{4a}$ are each independently hydrogen or substituted or unsubstituted alkyl, or together form a covalent bond;

R$_5$ is hydrogen or substituted or unsubstituted alkyl;

R$_6$ and R$_{6a}$ are each independently hydrogen or substituted or unsubstituted alkyl, or together form =O;

R$_7$ is a covalent bond, alkylene, azaalkyl, or azaaraalkyl or =NR$_{20}$ where R$_{20}$ is hydrogen or lower alkyl of 1 through 8 carbon atoms or —CH$_2$-3,5-bis(tri-fluoromethyl)benzyl or —CH$_2$X—R$^1$ or —YR$^1$ where Y is an aryl or heteroaryl group;

R$_8$ and R$_{8a}$ are each independently hydrogen or substituted or unsubstituted alkyl or together form =O;

R$_9$ is a pendant group containing 3 through 6 —CH$_2$CONHphenylCH$_2$CH(N(CH$_2$COOH)$_2$)(CH$_2$N(CH$_2$COOH)(CH$_2$CH$_2$N(CH$_2$COOH)$_2$)) groups or esters thereof or complexes thereof with gadolinium(III)

R$_{10}$ is hydrogen, or substituted or unsubstituted alkyl and;

each of R$_1$-R$_{10}$, when substituted, is substituted with one or more substituents each independently selected from Q, where Q is alkyl, haloalkyl, halo or —COOR$_b$ where R$_b$ is hydrogen, alkyl, alkenyl, alkynyl, cycloalkyl, aryl, heteroaryl, araalkyl, or OR$_c$ where R$_c$ is hydrogen, alkyl, alkenyl, alkynyl, cycloalkyl, or aryl or CONR$_d$R$_e$ where R$_d$ and R$_e$ are each independently hydrogen, alkyl, alkenyl, alkynyl, cycloalkyl, or aryl, or NR$_f$R$_g$ where R$_f$ and R$_g$ are each independently hydrogen, alkyl, alkenyl, alkynyl, cycloalkyl, or aryl, or =NR$_h$ where R$_h$ is hydrogen, alkyl, alkenyl, alkynyl, cycloalkyl, or aryl, or is an amino acid residue;

each Q is independently unsubstituted or is substituted with one or more substituents each independently selected from Q$_1$, where Q$_1$ is alkyl, haloalkyl, halo, or —COOR$_b$ where R$_b$ is hydrogen, alkyl, alkenyl, alkynyl, cycloalkyl, aryl, heteroaryl, araalkyl, or OR$_c$ where R$_c$ is hydrogen, alkyl, alkenyl, alkynyl, cycloalkyl, or aryl or CONR$_d$R$_e$ where R$_d$ and R$_e$ are each independently hydrogen, alkyl, alkenyl, alkynyl, cycloalkyl, or aryl, or NR$_f$R$_g$ where R$_f$ and R$_g$ are each independently hydrogen, alkyl, alkenyl, alkynyl, cycloalkyl, or aryl, or =NR$_h$ where R$_h$ is hydrogen, alkyl, alkenyl, alkynyl, cycloalkyl, or aryl, or is an amino acid residue.

4. The compound of claim 3 where R$_9$ is —CH$_2$CH$_2$CONHC(CH$_2$CH$_2$CONHphenylCH$_2$CH(N(CH$_2$COOH)$_2$)(CH$_2$N(CH$_2$COOH)(CH$_2$CH$_2$N(CH$_2$COOH)$_2$)))$_3$ group or esters thereof or complexes thereof with gadolinium(III).

5. A compound according to claim 3 having the formula:
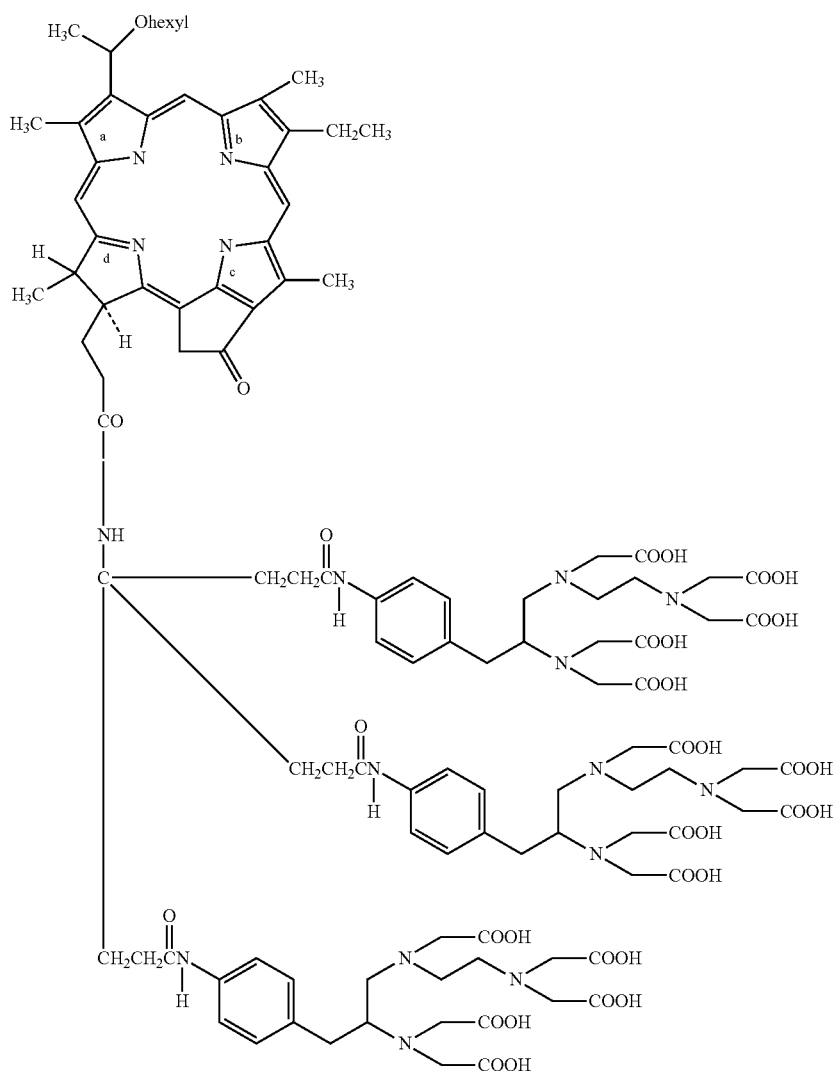
and gadolinium complexes thereof.
6. A compound according to claim 3 having the formula:
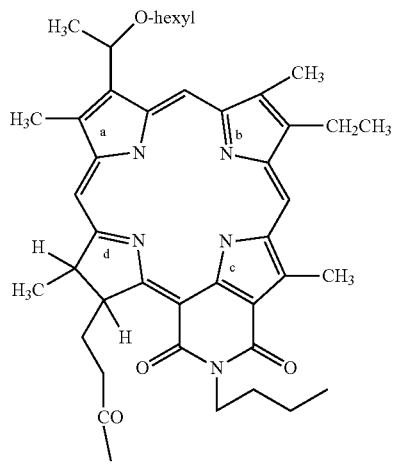

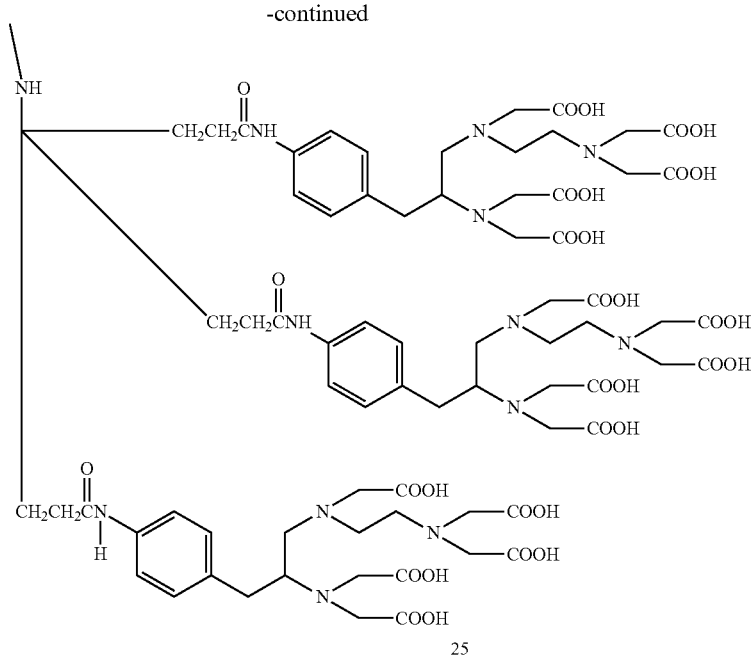
and gadolinium complexes thereof.
7. A compound according to claim 2 having the formula:
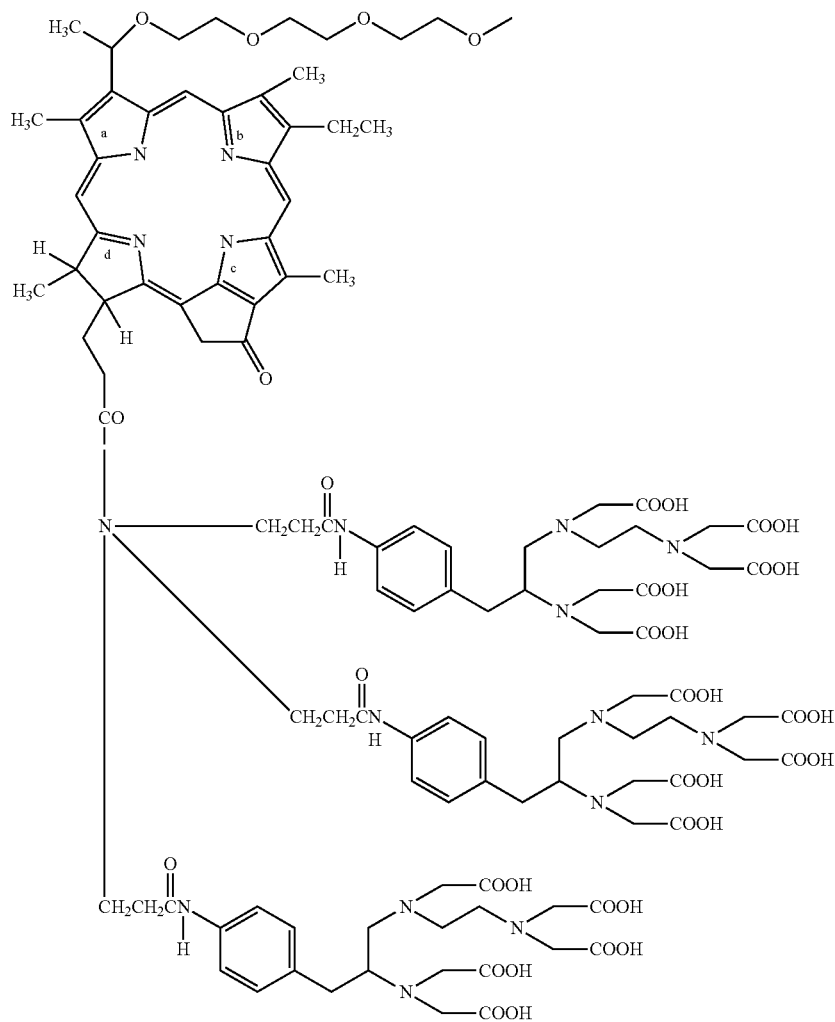

and gadolinium complexes thereof.

8. The compound of claim 3, wherein:
$R_1$ is substituted or unsubstituted alkyl;
$R_2$ is substituted or unsubstituted alkyl, substituted or unsubstituted alkenyl, or —C(O)$R_a$,
where $R_a$ is substituted or unsubstituted alkyl;
$R_{1a}$ and $R_{2a}$ together form a covalent bond;
$R_3$ and $R_4$ are each independently substituted or unsubstituted alkyl;
$R_{3a}$ and $R_{4a}$ are each independently hydrogen, or together form a covalent bond;
$R_5$ is substituted or unsubstituted alkyl;
$R_6$ and $R_{6a}$ together form =O;
$R_7$ is azaalkyl, or azaaralkyl;
$R_8$ and $R_{8a}$ together form =O;
$R_9$ and $R_{10}$ are each independently substituted or unsubstituted alkyl;
each of $R_1$-$R_{10}$, when substituted, is substituted with one or more substituents each independently selected from Q, where Q is halo, haloalkyl, COOR$_b$ where $R_b$ is hydrogen or alkyl, OR$_c$ where $R_c$ is alkyl or aralkyl, NR$_f$R$_g$ where R$_f$ and R$_g$ are each independently hydrogen, alkyl or aralkyl, or =NR$_h$ where R$_h$ is aralkyl;
each Q is independently unsubstituted or is substituted with one or more substituents each independently selected from $Q_1$, where $Q_1$ is halo, or haloalkyl.

9. The compound of claim 3, wherein:
$R_1$ is unsubstituted alkyl;
$R_2$ is substituted or unsubstituted alkyl, unsubstituted alkenyl, or —C(O)$R_a$, where $R_a$ is unsubstituted alkyl;
$R_{1a}$ and $R_{2a}$ together form a covalent bond;
$R_3$ and $R_4$ are each independently unsubstituted alkyl;
$R_{3a}$ and $R_{4a}$ are each independently hydrogen, or together form a covalent bond;
$R_5$ is unsubstituted alkyl;
$R_6$ and $R_{6a}$ together form =O;
$R_7$ is azaalkyl, or azaaralkyl;
$R_8$ and $R_{8a}$ together form =O;
$R_{10}$ is unsubstituted alkyl;
each of $R_1$-$R_{10}$, when substituted, is substituted with one or more substituents each independently selected from Q, where Q is halo, haloalkyl, COOR$_b$ where $R_b$ is hydrogen or alkyl, OR$_c$ where $R_c$ is alkyl or aralkyl, NR$_f$R$_g$ where R$_f$ and R$_g$ are each independently hydrogen, alkyl or aralkyl, or =NR$_h$ where R$_h$ is aralkyl;
each Q is independently unsubstituted or is substituted with one or more substituents each independently selected from $Q_1$, where $Q_1$ is halo, or haloalkyl.

10. The compound of claim 3, wherein:
$R_1$ is methyl;
$R_{1a}$ and $R_{2a}$ together form a covalent bond;
$R_3$ is methyl;
$R_4$ is ethyl;
$R_{3a}$ and $R_{4a}$ are each independently hydrogen, or together form a covalent bond;
$R_5$ is methyl; and
$R_{10}$ is methyl.

11. The compound claim 3, wherein:
$R_2$ is CH=CH$_2$, CH(OR$_{20}$)CH$_3$, C(O)Me, C(=NR$_{21}$)CH$_3$ or CH(NHR$_{21}$)CH$_3$;
where $R_{20}$ is methyl, butyl, heptyl, dodecyl or 3,5-bis(trifluoromethyl)-benzyl; and
$R_{21}$ is 3,5-bis(trifluoromethyl)benzyl.

12. The compound of claim 3, wherein:
$R_7$ is =NR$_{20}$, where $R_{20}$ is methyl, butyl, heptyl, dodecyl or 3,5-bis(trifluoromethyl)-benzyl.

13. A pharmaceutical composition, comprising a compound of claim 1 in a pharmaceutically acceptable carrier.

14. A pharmaceutical composition, comprising a compound of claim 3 in a pharmaceutically acceptable carrier.

15. An article of manufacture, comprising packaging material and a compound of claim 1 contained within the packaging material, and the packaging material includes a label that indicates that the compound is used in a photodynamic therapy treatment for hyperproliferative tissue.

16. An article of manufacture, comprising packaging material and a compound of claim 3 contained within the packaging material, and the packaging material includes a label that indicates that the compound is used in a photodynamic therapy treatment for hyperproliferative tissue.

17. A method for administering a therapy to hyperproliferative tissue, comprising:
(i) administering to a subject the compound of claim 1 that selectively interacts with the hyperproliferative tissue relative to normal tissue, and
(ii) irradiating the hyperproliferative tissue with light of a wavelength to kill or impair hyperproliferative tissue.

18. The method of claim 17, wherein the hyperproliferatve tissue is selected from the group consisting of: a vascular endothelial tissue, a neovasculature tissue, a neovasculature tissue present in an eye, an abnormal vascular wall of a tumor, a solid tumor, a tumor of a head, a tumor of a neck, a tumor of an eye, a tumor of a gastrointestinal tract, a tumor of a liver, a tumor of a breast, a tumor of a prostate, a tumors of a lung, a nonsolid tumor, and malignant cells of one of a hematopoietic tissue and a lymphoid tissue.

19. A method for administering a therapy to a hyperproliferative tissue, comprising:
(i) administering to a subject the compound of claim 3 that selectively interacts with hyperproliferative tissue relative to normal tissue, and
(ii) irradiating the subject with light of a wavelength to kill or impair hyperproliferative tissue.

20. The method of claim 19, wherein the hyperproliferative tissue is selected from the group consisting of: a vascular endothelial tissue, a neovasculature tissue, a neovasculature tissue present in an eye, an abnormal vascular wall of a tumor, a solid tumor, a tumor of a head, a tumor of a neck, a tumor of an eye, a tumor of a gastrointestinal tract, a tumor of a liver, a tumor of a breast, a tumor of a prostate, a tumors of a lung, a nonsolid tumor, and malignant cells of one of a hematopoietic tissue and a lymphoid tissue.

21. The method of claim 17, further comprising the step of allowing time for any of the compound that is not selectively interacted with the hyperproliferative tissue to clear from normal tissue of the subject prior to the step of irradiating.

22. A method of photodynamic therapy for treating hyperproliferative tissue in a subject, comprising:
(i) administering to the subject the compound of claim 1 that selectively interacts with the hyperproliferative tissue relative to normal tissue, and
(ii) irradiating the subject with light of a wavelength to activate the compound, whereby the hyperproliferative tissue is destroyed or impaired.

23. A method of photodynamic therapy for treating hyperproliferative tissue in a subject, comprising:
(i) administering to the subject the compound of claim 3 that selectively interacts with the hyperproliferative tissue relative to normal tissue, and
(ii) irradiating the subject with light of a wavelength to activate the compound, whereby the hyperproliferative tissue is destroyed or impaired.

24. A method for detecting the presence of a hyperproliferative tissue in a subject comprising:
  (i) administering to the subject an effective quantity of the compound of claim 1, said compound being fluorescent and that selectively interacts with the hyperproliferative tissue relative to normal tissue; and
  (ii) visualizing the compound within the patient by fluorescent spectroscopy.

25. A method for detecting the presence of a hyperproliferative tissue in a subject comprising:
  (i) administering to the subject an effective quantity of the compound of claim 3, said compound being fluorescent and that selectively interacts with the hyperproliferative tissue relative to normal tissue; and
  (ii) visualizing the compound within the patient by fluorescent spectroscopy.

26. A method for detecting the presence of a hyperproliferative tissue in a subject comprising:
  (i) administering to the subject an effective quantity of the compound of claim 1, said compound being magnetically resonant and that selectively interacts with the hyperproliferative tissue; and
  (ii) visualizing the compound within the patient by MRI imaging.

27. A method for detecting the presence of a hyperproliferative tissue in a subject comprising:
  (i) administering to the subject an effective quantity of the compound of claim 3, said compound being magnetically resonant and that selectively interacts with the hyperproliferative tissue relative to normal tissue; and
  (ii) visualizing the compound within the patient by MRI imaging.

* * * * *